United States Patent
Scheib et al.

(10) Patent No.: US 11,564,678 B2
(45) Date of Patent: Jan. 31, 2023

(54) FORCE SENSOR THROUGH STRUCTURED LIGHT DEFLECTION

(71) Applicant: Ethicon LLC, Guaynabo, PR (US)

(72) Inventors: Charles J. Scheib, Loveland, OH (US); Joshua D. Young, Flanders, NJ (US)

(73) Assignee: Cilag GmbH International, Zug (CH)

( * ) Notice: Subject to any disclaimer, the term of this patent is extended or adjusted under 35 U.S.C. 154(b) by 110 days.

(21) Appl. No.: 16/128,185

(22) Filed: Sep. 11, 2018

(65) Prior Publication Data
US 2020/0015902 A1    Jan. 16, 2020

Related U.S. Application Data

(60) Provisional application No. 62/698,625, filed on Jul. 16, 2018.

(51) Int. Cl.
*A61B 34/20* (2016.01)
*A61B 1/00* (2006.01)
(Continued)

(52) U.S. Cl.
CPC ...... *A61B 17/0482* (2013.01); *A61B 1/00006* (2013.01); *A61B 1/00013* (2013.01);
(Continued)

(58) Field of Classification Search
CPC . A61B 17/0482; A61B 90/03; A61B 17/0469; A61B 1/00149; A61B 1/051;
(Continued)

(56) References Cited

U.S. PATENT DOCUMENTS 4,753,641 A  6/1988 Vaslow
4,785,180 A  11/1988 Dietrich et al.
(Continued)

FOREIGN PATENT DOCUMENTS

CN  109011149 A  12/2018
DE  102015115903 A1  3/2017
(Continued)

OTHER PUBLICATIONS

Brecht, Hans-Peter et al., "Whole-body three-dimensional optoacoustic tomography system for small animals," Journal of Biomedical Optics, vol. 14, No. 6, 064007-1-064007-7 (2009).
(Continued)

*Primary Examiner* — Joseph M Santos Rodriguez
*Assistant Examiner* — Kaitlyn E Sebastian

(57) ABSTRACT

A surgical visualization system is disclosed. The surgical visualization system includes a control circuit communicatively coupled to a straight line laser source, a structured light emitter, and an image sensor; and a memory communicatively coupled to the control circuit. The memory stores instructions which, when executed, cause the control circuit to control the straight line laser source to project a straight laser line reference; control the structured light source to emit a structured light pattern onto a surface of an element of a surgical device; control the image sensor to detect the projected straight laser line and structured light reflected from the surface of the element of the surgical device; and determine a position of the element of the surgical device relative to the projected straight laser line reference.

21 Claims, 23 Drawing Sheets

(51) Int. Cl.

| | |
|---|---|
| A61B 1/04 | (2006.01) |
| A61B 1/06 | (2006.01) |
| A61B 1/07 | (2006.01) |
| A61B 1/313 | (2006.01) |
| A61B 17/00 | (2006.01) |
| A61B 17/34 | (2006.01) |
| A61B 17/04 | (2006.01) |
| A61B 17/06 | (2006.01) |
| A61B 17/062 | (2006.01) |
| A61B 34/32 | (2016.01) |
| A61B 34/30 | (2016.01) |
| A61B 1/045 | (2006.01) |
| A61B 17/11 | (2006.01) |
| A61B 17/115 | (2006.01) |
| A61B 17/064 | (2006.01) |
| A61B 90/30 | (2016.01) |
| A61B 90/00 | (2016.01) |
| A61B 1/05 | (2006.01) |
| A61B 5/00 | (2006.01) |
| A61B 90/13 | (2016.01) |
| A61B 34/00 | (2016.01) |
| A61B 90/35 | (2016.01) |
| A61B 17/02 | (2006.01) |
| G02F 1/13 | (2006.01) |
| G06T 1/00 | (2006.01) |
| A61B 34/10 | (2016.01) |

(52) U.S. Cl.
CPC ...... *A61B 1/00043* (2013.01); *A61B 1/00045* (2013.01); *A61B 1/00096* (2013.01); *A61B 1/00149* (2013.01); *A61B 1/04* (2013.01); *A61B 1/045* (2013.01); *A61B 1/05* (2013.01); *A61B 1/051* (2013.01); *A61B 1/06* (2013.01); *A61B 1/063* (2013.01); *A61B 1/0607* (2013.01); *A61B 1/0638* (2013.01); *A61B 1/0661* (2013.01); *A61B 1/07* (2013.01); *A61B 1/3132* (2013.01); *A61B 5/0036* (2018.08); *A61B 5/0086* (2013.01); *A61B 5/0095* (2013.01); *A61B 17/00234* (2013.01); *A61B 17/0218* (2013.01); *A61B 17/0469* (2013.01); *A61B 17/0483* (2013.01); *A61B 17/062* (2013.01); *A61B 17/064* (2013.01); *A61B 17/06066* (2013.01); *A61B 17/1114* (2013.01); *A61B 17/1155* (2013.01); *A61B 17/3423* (2013.01); *A61B 34/20* (2016.02); *A61B 34/30* (2016.02); *A61B 34/32* (2016.02); *A61B 34/73* (2016.02); *A61B 90/03* (2016.02); *A61B 90/13* (2016.02); *A61B 90/30* (2016.02); *A61B 90/35* (2016.02); *A61B 90/36* (2016.02); *A61B 90/361* (2016.02); *A61B 90/37* (2016.02); *G02F 1/1326* (2013.01); *G06T 1/0007* (2013.01); *A61B 1/00009* (2013.01); *A61B 1/0676* (2013.01); *A61B 34/25* (2016.02); *A61B 2017/00061* (2013.01); *A61B 2017/00119* (2013.01); *A61B 2017/00367* (2013.01); *A61B 2017/00477* (2013.01); *A61B 2017/00876* (2013.01); *A61B 2034/105* (2016.02); *A61B 2034/107* (2016.02); *A61B 2034/2051* (2016.02); *A61B 2034/2055* (2016.02); *A61B 2034/2057* (2016.02); *A61B 2034/2063* (2016.02); *A61B 2034/2065* (2016.02); *A61B 2034/301* (2016.02); *A61B 2034/302* (2016.02); *A61B 2090/061* (2016.02); *A61B 2090/064* (2016.02); *A61B 2090/306* (2016.02); *A61B 2090/367* (2016.02); *A61B 2090/373* (2016.02); *A61B 2090/374* (2016.02); *A61B 2090/378* (2016.02); *A61B 2090/3762* (2016.02); *A61B 2505/05* (2013.01); *A61B 2560/0462* (2013.01); *A61B 2576/00* (2013.01)

(58) Field of Classification Search
CPC ....... A61B 34/73; A61B 90/35; A61B 90/361; A61B 5/0095; A61B 17/0218; A61B 1/04; A61B 90/37; A61B 5/0036; A61B 90/13; A61B 1/00043; A61B 1/00096; A61B 1/00006; A61B 1/00045; A61B 1/0661; A61B 5/0086; A61B 90/30; A61B 90/36; A61B 1/05; A61B 1/06; A61B 17/064; A61B 17/1114; A61B 17/1155; A61B 34/30; A61B 1/045; A61B 1/0607; A61B 1/063; A61B 1/0638; A61B 1/07; A61B 1/3132; A61B 17/00234; A61B 17/3423; A61B 17/0483; A61B 17/06066; A61B 17/062; A61B 34/32; A61B 34/20; A61B 2017/00477; A61B 2017/00876; A61B 2090/064; A61B 2034/105; A61B 2505/05; A61B 2576/00; A61B 2034/2051; A61B 2034/2063; A61B 2034/2065; A61B 2090/374; A61B 2090/3762; A61B 2090/378; A61B 2034/107; A61B 1/0676; A61B 2090/061; A61B 2034/301; A61B 1/00009; A61B 2090/306; A61B 2034/302; A61B 2090/367; A61B 2090/373; A61B 2017/00119; A61B 2034/2057; A61B 2017/00061; A61B 2017/00367; A61B 2560/0462; A61B 2034/2055; A61B 5/7425; A61B 5/0064; A61B 2090/3937; A61B 5/0077; A61B 2017/00017; A61B 2017/00057; A61B 2090/304; A61B 2090/365; A61B 1/00087; A61B 1/00126; A61B 1/00154; A61B 1/018; A61B 1/053; A61B 5/0071; A61B 1/0016; A61B 1/0005; A61B 1/043; A61B 5/7267; A61B 2017/00154; A61B 2017/00809; A61B 2017/00818; A61B 2017/2927; A61B 2034/256; A61B 2090/066; A61B 2090/0811; A61B 2090/364; A61B 2090/371; A61B 2090/08021; A61B 2090/0807; A61B 5/0075; A61B 5/0084; A61B 5/1072; A61B 5/1076; A61B 5/1079; A61B 5/6844; A61B 5/6886; A61B 17/29; G01J 2003/104; G01J 2003/106; G01J 2003/2813; G01J 3/0229; G01J 3/027; G01J 3/10; G01J 3/2803; G01J 3/00; G01J 3/0278; G01J 3/2823; G01S 7/4865; G01S 17/10; G01S 17/894; G01S 17/89; G01S 17/48; G01S 17/36; G01N 2021/4797; G01N 21/4795; G01N 2021/3129; G01B 11/25; G01B 11/2513
See application file for complete search history.

(56) References Cited

U.S. PATENT DOCUMENTS

| 4,986,262 A | 1/1991 | Saito |
|---|---|---|
| 5,460,182 A | 10/1995 | Goodman et al. |
| 5,609,562 A | 3/1997 | Kaali |
| 6,350,233 B1 | 2/2002 | Lubowski |
| 6,386,758 B2 | 5/2002 | Loser |
| 6,632,183 B2 | 10/2003 | Bowman et al. |

(56) References Cited

U.S. PATENT DOCUMENTS

| | | |
|---|---|---|
| 6,804,012 B2 | 10/2004 | Gombert |
| 6,869,430 B2 | 3/2005 | Balbierz et al. |
| 6,951,535 B2 | 10/2005 | Ghodoussi et al. |
| 7,314,048 B2 | 1/2008 | Couture et al. |
| 7,477,931 B2 | 1/2009 | Hoyt |
| 7,516,675 B2 | 4/2009 | Kurtz et al. |
| 7,726,171 B2 | 6/2010 | Langlotz et al. |
| 7,740,623 B2 | 6/2010 | Nayak et al. |
| 7,766,210 B2 | 8/2010 | Shelton, IV et al. |
| 7,770,775 B2 | 8/2010 | Shelton, IV et al. |
| 7,798,385 B2 | 9/2010 | Boyden et al. |
| 7,810,691 B2 | 10/2010 | Boyden et al. |
| 7,901,353 B2 | 3/2011 | Vayser et al. |
| 7,905,840 B2 | 3/2011 | Pimenta et al. |
| 7,975,894 B2 | 7/2011 | Boyden et al. |
| 8,041,089 B2 | 10/2011 | Drumm et al. |
| 8,063,883 B2 | 11/2011 | Senft et al. |
| 8,073,528 B2 | 12/2011 | Zhao et al. |
| 8,079,950 B2 | 12/2011 | Stern et al. |
| 8,142,450 B2 | 3/2012 | Harris et al. |
| 8,161,977 B2 | 4/2012 | Shelton, IV et al. |
| 8,224,484 B2 | 7/2012 | Swarup et al. |
| 8,231,639 B2 | 7/2012 | Bolduc et al. |
| 8,523,043 B2 | 9/2013 | Ullrich et al. |
| 8,632,468 B2 | 1/2014 | Glossop et al. |
| 8,652,148 B2 | 2/2014 | Zuhars |
| 8,706,211 B2 | 4/2014 | Dacey, Jr. et al. |
| 8,755,576 B2 | 6/2014 | Taerum |
| 8,763,879 B2 | 7/2014 | Shelton, IV et al. |
| 8,820,603 B2 | 9/2014 | Shelton, IV et al. |
| 8,840,616 B2 | 9/2014 | Wilkinson et al. |
| 8,932,208 B2 | 1/2015 | Kendale et al. |
| 8,934,003 B2 | 1/2015 | Popovic et al. |
| 8,992,558 B2 | 3/2015 | Stone et al. |
| 9,005,118 B2 | 4/2015 | Selover et al. |
| 9,044,230 B2 | 6/2015 | Morgan et al. |
| 9,064,173 B2 | 6/2015 | Redden |
| 9,072,501 B2 | 7/2015 | Menchaca et al. |
| 9,072,535 B2 | 7/2015 | Shelton, IV et al. |
| 9,119,670 B2 | 9/2015 | Yang et al. |
| 9,141,868 B2 | 9/2015 | Xu et al. |
| 9,161,817 B2 | 10/2015 | Olson et al. |
| 9,161,820 B2 | 10/2015 | Mark et al. |
| 9,179,822 B2 | 11/2015 | Kitamura et al. |
| 9,241,693 B2 | 1/2016 | Taylor et al. |
| 9,254,103 B2 | 2/2016 | Krishnaswamy et al. |
| 9,259,290 B2 | 2/2016 | Jenkins et al. |
| 9,265,587 B2 | 2/2016 | Vancamberg et al. |
| 9,274,047 B2 | 3/2016 | Velten et al. |
| 9,282,878 B2 | 3/2016 | Grey et al. |
| 9,295,773 B2 | 3/2016 | Prosl et al. |
| 9,326,770 B2 | 5/2016 | Shelton, IV et al. |
| 9,345,389 B2 | 5/2016 | Nie et al. |
| 9,402,726 B2 | 8/2016 | Linderman et al. |
| 9,480,534 B2 | 11/2016 | Bowling et al. |
| 9,561,019 B2 | 2/2017 | Mihailescu et al. |
| 9,561,082 B2 | 2/2017 | Yen et al. |
| 9,597,054 B2 | 3/2017 | Kudavelly et al. |
| 9,649,109 B2 | 5/2017 | Ranucci et al. |
| 9,720,076 B2 | 8/2017 | Guo et al. |
| 9,730,690 B2 | 8/2017 | Shanley et al. |
| 9,788,851 B2 | 10/2017 | Dannaher et al. |
| 9,801,685 B2 | 10/2017 | Nguyen et al. |
| 9,855,317 B2 | 1/2018 | Bright |
| 9,857,167 B2 | 1/2018 | Jovanovski et al. |
| 9,883,857 B2 | 2/2018 | Shluzas et al. |
| 9,901,409 B2 | 2/2018 | Yang et al. |
| 9,918,640 B2 | 3/2018 | Ntziachristos et al. |
| 9,987,019 B2 | 6/2018 | Sato |
| 10,010,326 B2 | 7/2018 | Sato |
| 10,022,199 B2 | 7/2018 | Gassner et al. |
| 10,045,763 B2 | 8/2018 | Sato |
| 10,068,173 B2 | 9/2018 | Vayser et al. |
| 10,070,929 B2 | 9/2018 | Tanji |
| 10,085,611 B2 | 10/2018 | Yabe et al. |
| 10,123,706 B2 | 11/2018 | Elbaz et al. |
| 10,136,959 B2 | 11/2018 | Mintz et al. |
| 10,143,470 B2 | 12/2018 | Sato |
| 10,170,205 B2 | 1/2019 | Curd et al. |
| 10,194,981 B2 | 2/2019 | Baibas et al. |
| 10,194,990 B2 | 2/2019 | Amanatullah et al. |
| 10,219,738 B2 | 3/2019 | Monty et al. |
| 10,255,723 B2 | 4/2019 | Thomas et al. |
| 10,314,463 B2 | 6/2019 | Agrawal et al. |
| 10,357,253 B2 | 7/2019 | Sato |
| 10,390,835 B2 | 8/2019 | Williams |
| 10,433,911 B2 | 10/2019 | Wang et al. |
| 10,470,763 B2 | 11/2019 | Yates et al. |
| 10,506,991 B2 | 12/2019 | Govari |
| 10,510,149 B2 | 12/2019 | Cutu et al. |
| 10,512,518 B2 | 12/2019 | Vayser et al. |
| 10,531,074 B2 | 1/2020 | Wilson et al. |
| 10,546,423 B2 | 1/2020 | Jones et al. |
| 10,548,679 B2 | 2/2020 | Carlson et al. |
| 10,561,465 B2 | 2/2020 | Scholl et al. |
| 10,576,246 B2 | 3/2020 | Fischell et al. |
| 10,588,699 B2 | 3/2020 | Richmond et al. |
| 10,666,928 B2 | 5/2020 | Liu |
| 10,687,797 B2 | 6/2020 | Stone et al. |
| 10,695,166 B2 | 6/2020 | Willis et al. |
| 10,702,186 B2 | 7/2020 | Amies et al. |
| 10,704,093 B2 | 7/2020 | Deng et al. |
| 10,743,868 B2 | 8/2020 | Shelton, IV et al. |
| 10,792,034 B2 | 10/2020 | Scheib et al. |
| 10,806,518 B2 | 10/2020 | Amanatullah |
| 10,813,700 B2 | 10/2020 | Amanatullah |
| 10,861,197 B2 | 12/2020 | Kobayashi |
| 10,866,783 B2 | 12/2020 | Atarot et al. |
| 10,881,458 B2 | 1/2021 | Fischell et al. |
| 10,925,465 B2 | 2/2021 | Tully et al. |
| 10,973,519 B2 | 4/2021 | Weir et al. |
| 11,006,100 B1 | 5/2021 | Douglas |
| 11,020,016 B2 | 6/2021 | Wallace et al. |
| 11,058,501 B2 | 7/2021 | Tokarchuk et al. |
| 11,100,631 B2 | 8/2021 | Yates et al. |
| 11,109,866 B2 | 9/2021 | Shelton, IV et al. |
| 11,219,501 B2 | 1/2022 | Shelton, IV et al. |
| 2001/0012327 A1 | 8/2001 | Loser |
| 2003/0069591 A1 | 4/2003 | Carson et al. |
| 2004/0082842 A1 | 4/2004 | Lumba et al. |
| 2004/0106916 A1 | 6/2004 | Quaid et al. |
| 2004/0147926 A1 | 7/2004 | Iversen |
| 2004/0176751 A1 | 9/2004 | Weitzner et al. |
| 2004/0230199 A1 | 11/2004 | Jansen et al. |
| 2005/0113846 A1 | 5/2005 | Carson |
| 2005/0124975 A1 | 6/2005 | Law |
| 2005/0167621 A1 | 8/2005 | Zeng et al. |
| 2005/0177181 A1 | 8/2005 | Kagan et al. |
| 2005/0279354 A1 | 12/2005 | Deutsch et al. |
| 2006/0013454 A1 | 1/2006 | Flewelling et al. |
| 2006/0079841 A1 | 4/2006 | Duff et al. |
| 2006/0206007 A1 | 9/2006 | Bala |
| 2006/0224045 A1 | 10/2006 | Whipple et al. |
| 2006/0293557 A1 | 12/2006 | Chuanggui et al. |
| 2007/0014784 A1 | 1/2007 | Nayak et al. |
| 2007/0019781 A1 | 1/2007 | Haras |
| 2007/0040906 A1 | 2/2007 | Iketani |
| 2007/0093748 A1 | 4/2007 | Nayak et al. |
| 2007/0100210 A1 | 5/2007 | Selover et al. |
| 2007/0123912 A1 | 5/2007 | Carson |
| 2007/0156021 A1 | 7/2007 | Morse et al. |
| 2007/0172472 A1 | 7/2007 | Nayak |
| 2007/0175955 A1 | 8/2007 | Shelton et al. |
| 2007/0239149 A1 | 10/2007 | Lieponis |
| 2007/0265495 A1 | 11/2007 | Vayser |
| 2008/0001919 A1 | 1/2008 | Pascucci |
| 2008/0004633 A1 | 1/2008 | Arata et al. |
| 2008/0077158 A1 | 3/2008 | Haider et al. |
| 2008/0144906 A1 | 6/2008 | Allred et al. |
| 2008/0151233 A1 | 6/2008 | Blanke et al. |
| 2008/0194930 A1 | 8/2008 | Harris et al. |
| 2008/0228104 A1 | 9/2008 | Uber et al. |
| 2008/0269596 A1 | 10/2008 | Revie et al. |
| 2008/0319491 A1 | 12/2008 | Schoenefeld |

(56) References Cited

U.S. PATENT DOCUMENTS

| | | | |
|---|---|---|---|
| 2009/0000627 A1 | 1/2009 | Quaid et al. | |
| 2009/0123111 A1* | 5/2009 | Udd | A61B 5/06 385/13 |
| 2009/0234223 A1 | 9/2009 | Onoda et al. | |
| 2010/0030231 A1 | 2/2010 | Revie et al. | |
| 2010/0081875 A1 | 4/2010 | Fowler et al. | |
| 2010/0087755 A1 | 4/2010 | Boezaart | |
| 2010/0137882 A1 | 6/2010 | Quaid, III | |
| 2010/0152539 A1 | 6/2010 | Ghabrial et al. | |
| 2010/0280493 A1 | 11/2010 | Nayak | |
| 2011/0014181 A1 | 1/2011 | Thornton | |
| 2011/0071531 A1 | 3/2011 | Carson | |
| 2011/0082369 A1 | 4/2011 | Mohr et al. | |
| 2011/0201881 A1* | 8/2011 | Emch | A61B 17/320036 600/108 |
| 2011/0257611 A1 | 10/2011 | Locke et al. | |
| 2011/0257661 A1 | 10/2011 | Choi et al. | |
| 2011/0306985 A1 | 12/2011 | Inoue et al. | |
| 2012/0004894 A1 | 1/2012 | Butler et al. | |
| 2012/0046668 A1 | 2/2012 | Gantes | |
| 2012/0143341 A1 | 6/2012 | Zipnick | |
| 2012/0165837 A1 | 6/2012 | Belman et al. | |
| 2012/0265022 A1 | 10/2012 | Menn | |
| 2012/0300051 A1 | 11/2012 | Daigo et al. | |
| 2013/0035583 A1 | 2/2013 | Park et al. | |
| 2013/0100250 A1 | 4/2013 | Raskar et al. | |
| 2013/0172902 A1 | 7/2013 | Lightcap et al. | |
| 2013/0211244 A1 | 8/2013 | Nathaniel | |
| 2013/0274596 A1 | 10/2013 | Azizian et al. | |
| 2013/0274673 A1 | 10/2013 | Fischell et al. | |
| 2013/0274674 A1 | 10/2013 | Fischell et al. | |
| 2013/0296712 A1 | 11/2013 | Durvasula | |
| 2014/0005685 A1 | 1/2014 | Modrow et al. | |
| 2014/0024945 A1 | 1/2014 | Mung et al. | |
| 2014/0035762 A1 | 2/2014 | Shelton, IV et al. | |
| 2014/0039520 A1 | 2/2014 | Haider et al. | |
| 2014/0114180 A1 | 4/2014 | Jain | |
| 2014/0163359 A1 | 6/2014 | Sholev et al. | |
| 2014/0163664 A1 | 6/2014 | Goldsmith | |
| 2014/0171793 A1 | 6/2014 | Lin et al. | |
| 2014/0175150 A1 | 6/2014 | Shelton, IV et al. | |
| 2014/0179997 A1 | 6/2014 | Grunberg et al. | |
| 2014/0336461 A1* | 11/2014 | Reiter | A61B 1/06 600/111 |
| 2014/0378763 A1 | 12/2014 | Rot et al. | |
| 2014/0378843 A1 | 12/2014 | Valdes et al. | |
| 2015/0018999 A1 | 1/2015 | Lee et al. | |
| 2015/0025548 A1 | 1/2015 | Franklin et al. | |
| 2015/0032140 A1 | 1/2015 | Khouri | |
| 2015/0051460 A1 | 2/2015 | Saxena et al. | |
| 2015/0066107 A1 | 3/2015 | Richter et al. | |
| 2015/0133909 A1 | 5/2015 | van der Weide et al. | |
| 2015/0145966 A1 | 5/2015 | Krieger et al. | |
| 2015/0223903 A1 | 8/2015 | Bell et al. | |
| 2015/0238276 A1 | 8/2015 | Atarot et al. | |
| 2015/0245878 A1 | 9/2015 | Jaramaz et al. | |
| 2015/0297177 A1 | 10/2015 | Boctor et al. | |
| 2015/0305650 A1 | 10/2015 | Hunter et al. | |
| 2015/0366628 A1 | 12/2015 | Ingmanson | |
| 2016/0000516 A1 | 1/2016 | Cheng et al. | |
| 2016/0007827 A1 | 1/2016 | Frimer et al. | |
| 2016/0014328 A1 | 1/2016 | Rokutanda | |
| 2016/0022146 A1 | 1/2016 | Piron et al. | |
| 2016/0038004 A1 | 2/2016 | Tanaka | |
| 2016/0086380 A1 | 3/2016 | Vayser et al. | |
| 2016/0183841 A1 | 6/2016 | Duindam et al. | |
| 2016/0206204 A1 | 7/2016 | Matsuda et al. | |
| 2016/0228090 A1 | 8/2016 | Boctor et al. | |
| 2016/0235304 A1 | 8/2016 | Tzoumas et al. | |
| 2016/0256101 A1 | 9/2016 | Aharon et al. | |
| 2016/0331467 A1 | 11/2016 | Slamin et al. | |
| 2016/0346034 A1 | 12/2016 | Arya et al. | |
| 2016/0354166 A1 | 12/2016 | Popovic et al. | |
| 2017/0007350 A1 | 1/2017 | Popovic et al. | |
| 2017/0020613 A1 | 1/2017 | Kang et al. | |
| 2017/0055819 A1 | 3/2017 | Hansen et al. | |
| 2017/0059408 A1 | 3/2017 | Korner et al. | |
| 2017/0071475 A1 | 3/2017 | Irisawa | |
| 2017/0079530 A1 | 3/2017 | DiMaio et al. | |
| 2017/0165008 A1 | 6/2017 | Finley | |
| 2017/0172382 A1 | 6/2017 | Nir et al. | |
| 2017/0172662 A1 | 6/2017 | Panescu et al. | |
| 2017/0189006 A1 | 7/2017 | Shluzas et al. | |
| 2017/0197028 A1 | 7/2017 | Goldsmith | |
| 2017/0202624 A1 | 7/2017 | Atarot et al. | |
| 2017/0209050 A1 | 7/2017 | Fengler et al. | |
| 2017/0238962 A1 | 8/2017 | Hansen et al. | |
| 2017/0251900 A1 | 9/2017 | Hansen et al. | |
| 2017/0258526 A1 | 9/2017 | Lang | |
| 2017/0265943 A1 | 9/2017 | Sela et al. | |
| 2017/0296213 A1 | 10/2017 | Swensgard et al. | |
| 2017/0304007 A1 | 10/2017 | Piron et al. | |
| 2017/0312032 A1 | 11/2017 | Amanatullah et al. | |
| 2017/0366773 A1 | 12/2017 | Kiraly et al. | |
| 2017/0367580 A1 | 12/2017 | DiMaio et al. | |
| 2018/0014777 A1 | 1/2018 | Amir et al. | |
| 2018/0014851 A1 | 1/2018 | Hansen et al. | |
| 2018/0214016 A1 | 8/2018 | Thommen et al. | |
| 2018/0247153 A1 | 8/2018 | Ganapati et al. | |
| 2018/0271603 A1 | 9/2018 | Nir et al. | |
| 2018/0310829 A1* | 11/2018 | Frangioni | A61B 5/0071 |
| 2018/0333210 A1 | 11/2018 | Nijkamp et al. | |
| 2018/0343381 A1 | 11/2018 | Kobayashi et al. | |
| 2018/0344140 A1 | 12/2018 | Aizenfeld | |
| 2018/0368883 A1 | 12/2018 | Rossa et al. | |
| 2019/0000478 A1 | 1/2019 | Messerly et al. | |
| 2019/0008579 A1* | 1/2019 | Begg | A61B 18/1445 |
| 2019/0022418 A1 | 1/2019 | Fishman | |
| 2019/0046276 A1 | 2/2019 | Inglese et al. | |
| 2019/0053691 A1 | 2/2019 | Hansen et al. | |
| 2019/0053872 A1 | 2/2019 | Meglan | |
| 2019/0069824 A1 | 3/2019 | Darty et al. | |
| 2019/0076186 A1 | 3/2019 | Fischell et al. | |
| 2019/0076187 A1 | 3/2019 | Fischell et al. | |
| 2019/0099070 A1 | 4/2019 | Mark et al. | |
| 2019/0099226 A1 | 4/2019 | Hallen | |
| 2019/0104919 A1 | 4/2019 | Shelton, IV et al. | |
| 2019/0110924 A1 | 4/2019 | Moreno et al. | |
| 2019/0117319 A1 | 4/2019 | Cima et al. | |
| 2019/0142524 A1 | 5/2019 | Hladio et al. | |
| 2019/0175272 A1 | 6/2019 | Khan et al. | |
| 2019/0180865 A1 | 6/2019 | Kashima et al. | |
| 2019/0192145 A1 | 6/2019 | Shelton, IV et al. | |
| 2019/0192150 A1 | 6/2019 | Widenhouse et al. | |
| 2019/0192151 A1 | 6/2019 | Shelton, IV et al. | |
| 2019/0200905 A1 | 7/2019 | Shelton, IV et al. | |
| 2019/0200906 A1 | 7/2019 | Shelton, IV et al. | |
| 2019/0200981 A1 | 7/2019 | Harris et al. | |
| 2019/0201045 A1 | 7/2019 | Yates et al. | |
| 2019/0201046 A1 | 7/2019 | Shelton, IV et al. | |
| 2019/0201047 A1 | 7/2019 | Yates et al. | |
| 2019/0201102 A1 | 7/2019 | Shelton, IV et al. | |
| 2019/0201111 A1 | 7/2019 | Shelton, IV et al. | |
| 2019/0201120 A1 | 7/2019 | Shelton, IV et al. | |
| 2019/0201136 A1 | 7/2019 | Shelton, IV et al. | |
| 2019/0201137 A1 | 7/2019 | Shelton, IV et al. | |
| 2019/0201142 A1 | 7/2019 | Shelton, IV et al. | |
| 2019/0201594 A1 | 7/2019 | Shelton, IV et al. | |
| 2019/0205567 A1 | 7/2019 | Shelton, IV et al. | |
| 2019/0206562 A1 | 7/2019 | Shelton, IV et al. | |
| 2019/0206563 A1 | 7/2019 | Shelton, IV et al. | |
| 2019/0206564 A1 | 7/2019 | Shelton, IV et al. | |
| 2019/0206569 A1 | 7/2019 | Shelton, IV et al. | |
| 2019/0208641 A1 | 7/2019 | Yates et al. | |
| 2019/0247050 A1 | 8/2019 | Goldsmith | |
| 2019/0269476 A1 | 9/2019 | Bowling et al. | |
| 2019/0293554 A1 | 9/2019 | Nakao et al. | |
| 2019/0307524 A1 | 10/2019 | Popovic | |
| 2019/0311542 A1 | 10/2019 | Douglas et al. | |
| 2019/0320117 A1 | 10/2019 | Wu et al. | |
| 2019/0320878 A1 | 10/2019 | Duindam et al. | |
| 2019/0321118 A1 | 10/2019 | Genova et al. | |
| 2019/0388157 A1 | 12/2019 | Shameli et al. | |
| 2020/0008879 A1 | 1/2020 | Popovic et al. | |

(56) References Cited

U.S. PATENT DOCUMENTS

| | | |
|---|---|---|
| 2020/0015668 A1 | 1/2020 | Scheib |
| 2020/0015806 A1 | 1/2020 | Scheib et al. |
| 2020/0015897 A1 | 1/2020 | Scheib et al. |
| 2020/0015898 A1 | 1/2020 | Scheib et al. |
| 2020/0015899 A1 | 1/2020 | Scheib et al. |
| 2020/0015900 A1 | 1/2020 | Scheib et al. |
| 2020/0015901 A1 | 1/2020 | Scheib et al. |
| 2020/0015903 A1 | 1/2020 | Scheib et al. |
| 2020/0015904 A1 | 1/2020 | Scheib et al. |
| 2020/0015906 A1 | 1/2020 | Scheib et al. |
| 2020/0015907 A1 | 1/2020 | Scheib |
| 2020/0015914 A1 | 1/2020 | Scheib et al. |
| 2020/0015923 A1 | 1/2020 | Scheib et al. |
| 2020/0015924 A1 | 1/2020 | Scheib et al. |
| 2020/0015925 A1 | 1/2020 | Scheib |
| 2020/0018844 A1 | 1/2020 | Fridman et al. |
| 2020/0037858 A1 | 2/2020 | Pedreira de Cerqueira Filho |
| 2020/0038112 A1 | 2/2020 | Amanatullah et al. |
| 2020/0060725 A1 | 2/2020 | Sato |
| 2020/0121245 A1 | 4/2020 | Barclay et al. |
| 2020/0281662 A1 | 9/2020 | Cong et al. |
| 2020/0289205 A1 | 9/2020 | Scheib et al. |
| 2020/0289216 A1 | 9/2020 | Denlinger et al. |
| 2020/0289217 A1 | 9/2020 | Denlinger et al. |
| 2020/0289219 A1 | 9/2020 | Denlinger et al. |
| 2020/0289220 A1 | 9/2020 | Denlinger et al. |
| 2020/0289221 A1 | 9/2020 | Denlinger et al. |
| 2020/0289222 A1 | 9/2020 | Denlinger et al. |
| 2020/0289223 A1 | 9/2020 | Denlinger et al. |
| 2020/0289228 A1 | 9/2020 | Denlinger et al. |
| 2020/0289229 A1 | 9/2020 | Denlinger et al. |
| 2020/0289230 A1 | 9/2020 | Denlinger et al. |
| 2020/0291476 A1 | 9/2020 | Deng et al. |
| 2020/0315721 A1 | 10/2020 | Rabindran et al. |
| 2020/0367972 A1 | 11/2020 | Zhang et al. |
| 2020/0397266 A1 | 12/2020 | Hufford |
| 2020/0405395 A1 | 12/2020 | Gullotti et al. |
| 2021/0068908 A1 | 3/2021 | Thienphrapa et al. |
| 2021/0137634 A1 | 5/2021 | Lang |
| 2021/0196098 A1 | 7/2021 | Shelton, IV et al. |
| 2021/0196108 A1 | 7/2021 | Shelton, IV |
| 2021/0196109 A1 | 7/2021 | Shelton, IV et al. |
| 2021/0196381 A1 | 7/2021 | Eckert et al. |
| 2021/0196382 A1 | 7/2021 | Mumaw et al. |
| 2021/0196383 A1 | 7/2021 | Shelton, IV et al. |
| 2021/0196384 A1 | 7/2021 | Shelton, IV et al. |
| 2021/0196385 A1 | 7/2021 | Shelton, IV et al. |
| 2021/0196386 A1 | 7/2021 | Shelton, IV et al. |
| 2021/0196423 A1 | 7/2021 | Shelton, IV et al. |
| 2021/0196425 A1 | 7/2021 | Shelton, IV et al. |
| 2021/0199557 A1 | 7/2021 | Shelton, IV et al. |
| 2021/0205019 A1 | 7/2021 | Shelton, IV et al. |
| 2021/0212792 A1 | 7/2021 | Shelton, IV et al. |
| 2021/0212794 A1 | 7/2021 | Shelton, IV et al. |
| 2021/0259660 A1 | 8/2021 | Bharat et al. |
| 2021/0259789 A1 | 8/2021 | Wright et al. |
| 2021/0275251 A1 | 9/2021 | Shelton, IV et al. |
| 2021/0275252 A1 | 9/2021 | Shelton, IV et al. |
| 2021/0282861 A1 | 9/2021 | Eckert et al. |
| 2021/0307835 A1 | 10/2021 | Shelton, IV et al. |
| 2021/0307865 A1 | 10/2021 | Shelton, IV et al. |
| 2021/0307866 A1 | 10/2021 | Shelton, IV et al. |
| 2021/0307867 A1 | 10/2021 | Shelton, IV et al. |
| 2021/0307868 A1 | 10/2021 | Shelton, IV et al. |
| 2021/0307869 A1 | 10/2021 | Shelton, IV et al. |
| 2021/0307870 A1 | 10/2021 | Shelton, IV et al. |
| 2022/0000559 A1 | 1/2022 | Leonard et al. |
| 2022/0000565 A1 | 1/2022 | Gururaj et al. |
| 2022/0047259 A1 | 2/2022 | Prior et al. |
| 2022/0133412 A1 | 5/2022 | Tolkowsky et al. |

FOREIGN PATENT DOCUMENTS

| | | |
|---|---|---|
| EP | 2754383 A2 | 7/2014 |
| JP | 2006280591 A | 10/2006 |
| JP | 4106991 B2 | 6/2008 |
| KR | 20120068597 A | 6/2012 |
| WO | WO-2008033133 A2 | 3/2008 |
| WO | WO-2013093391 A1 | 6/2013 |
| WO | WO-2013163391 A1 | 10/2013 |
| WO | WO-2015135058 A1 | 9/2015 |
| WO | WO-2018200767 A1 | 11/2018 |
| WO | WO-2019130085 A1 | 7/2019 |
| WO | WO-2020116991 A1 | 6/2020 |

OTHER PUBLICATIONS

Ge, Jiawei et al., "Landmark-Guided Deformable Image Registration for Supervised Autonomous Robotic Tumor Resection," Advances in Intelligent Data Analysis XIX, LNCS, Springer International Publishing, pp. 320-328, Oct. 10, 2019.

Kurata et al. "Time-of-flight Near-infrared Spectroscopy for Non-destructive Measurement of Internal Quality in Grapefruit," J. Amer. Soc. Hort. Sci. 138(3): 225-228, 2013.

Thyroid Fine Needle Aspiration (FNA) Biopsy, retrieved from www.fairview.org/patient-education/90246 on Feb. 4, 2020. 3 pages.

Open Technique for Low Anterior Resection, retrieved from https://abdominalkey.com/open-technique-for-low-anterior-resection/ on Feb. 4, 2020. 6 pages.

Sukumar et al., "Robotic Partial Nephrectomy Using Robotic Bulldog Clamps," JSLS: Journal of the Society of Laparoendoscopic Surgeons, 15(4), pp. 520-526, 2011.

X12C4 Robotic Drop-In, retrieved from https://bkultrasound.com/transducers/x12c4-robotic-drop-in on Feb. 13, 2020. 2 pages.

"ATM-MPLS Networking Version 2.0, af-aic-0178.001" ATM Standard, The ATM Forum Technical Committee, published Aug. 2003.

IEEE Std 802.3-2012 (Revision of IEEE Std 802.3-2008, published Dec. 28, 2012.

Lacy, Antonio, "Main Steps to Perform a Sleeve Gastrectomy," retrieved from https://aischannel.com/society/main-steps-to-perform-a-sleeve-gastrectomy/ on Feb. 14, 2020. pp. 1-7, Jun. 11, 2015.

Elhajj, et al., "Sleeve Gastrectomy Surgical Assistive Instrument for Accurate Remnant Stomach Volume," ASME, J. Med. Devices, vol. 4, pp. 1-10, Jun. 2010.

* cited by examiner

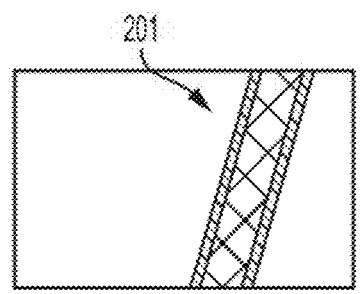 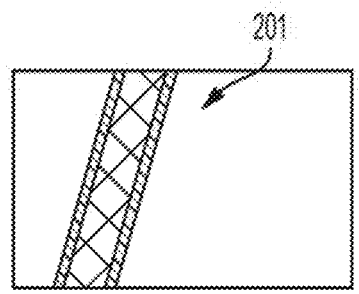
FIG. 7A    FIG. 7B
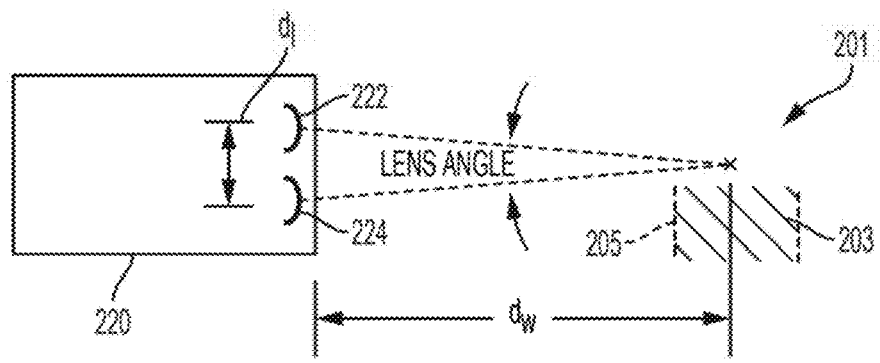
FIG. 8

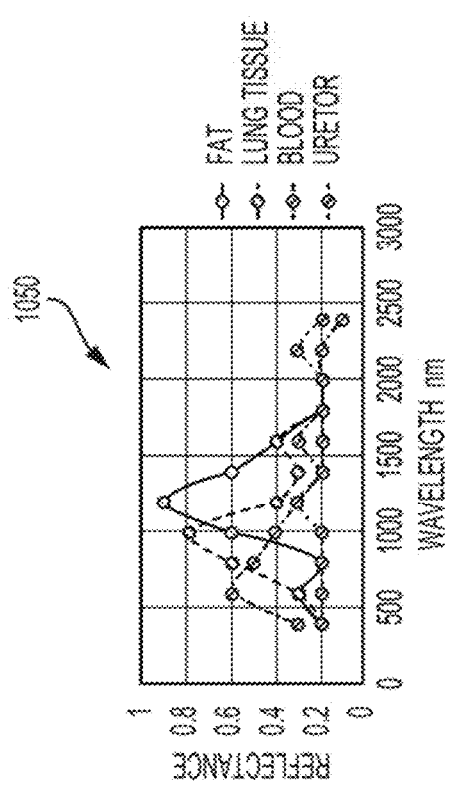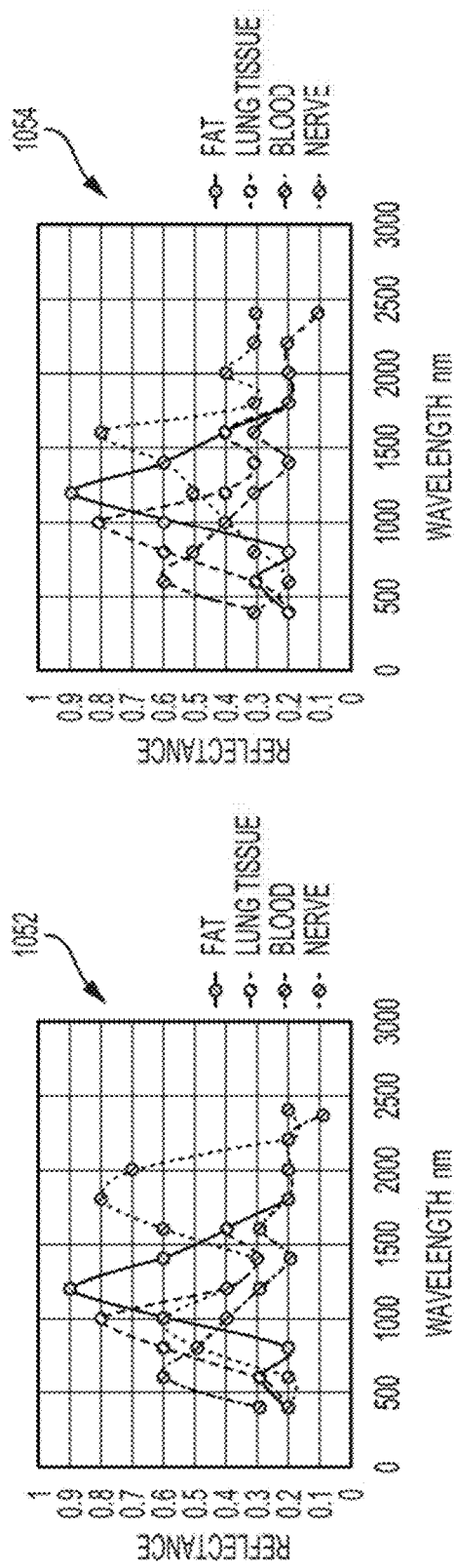
FIG. 16
FIG. 17
FIG. 18

FORCE SENSOR THROUGH STRUCTURED LIGHT DEFLECTION

CROSS-REFERENCE TO RELATED APPLICATION

This application claims the benefit of priority under 35 U.S.C. § 119(e) to U.S. Provisional Patent Application Ser. No. 62/698,625, titled DIGITAL SURGERY IMAGING/VISUALIZATION SYSTEM, filed Jul. 16, 2018, the disclosure of which is herein incorporated by reference in its entirety.

BACKGROUND

Surgical systems often incorporate an imaging system, which can allow the clinician(s) to view the surgical site and/or one or more portions thereof on one or more displays such as a monitor, for example. The display(s) can be local and/or remote to a surgical theater. An imaging system can include a scope with a camera that views the surgical site and transmits the view to a display that is viewable by a clinician. Scopes include, but are not limited to, arthroscopes, angioscopes, bronchoscopes, choledochoscopes, colonoscopes, cytoscopes, duodenoscopes, enteroscopes, esophagogastro-duodenoscopes (gastroscopes), endoscopes, laryngoscopes, nasopharyngo-neproscopes, sigmoidoscopes, thoracoscopes, ureteroscopes, and exoscopes. Imaging systems can be limited by the information that they are able to recognize and/or convey to the clinician(s). For example, certain concealed structures, physical contours, and/or dimensions within a three-dimensional space may be unrecognizable intraoperatively by certain imaging systems. Additionally, certain imaging systems may be incapable of communicating and/or conveying certain information to the clinician(s) intraoperatively.

SUMMARY

In one aspect the present disclosure provides a surgical visualization system. The surgical visualization system comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of an element of a surgical device; control the image sensor to detect the projected straight laser line and structured light reflected from the surface of the element of the surgical device; and determine a position of the element of the surgical device relative to the projected straight laser line reference.

In another aspect, the present disclosure provides a surgical visualization system comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of distal end of a shaft of a surgical device; control the image sensor to detect the projected straight laser line and structured light reflected from the surface of the distal end of the shaft of the surgical device; and determine a distance "d" from the projected straight laser line reference to the distal end of the shaft of the surgical device.

In yet another aspect, the present disclosure provides a surgical visualization system comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of distal end of a first and second jaw of a surgical device; control the image sensor to detect the projected straight laser line and structured light reflected from the surface of the distal end of the shaft of the surgical device; and determine a first distance "$d_1$" from the projected straight laser line reference to the of the distal end of the first jaw; and determine a second distance "$d_2$" from the projected straight laser line reference to the of the distal end of the second jaw.

FIGURES

The novel features of the various aspects are set forth with particularity in the appended claims. The described aspects, however, both as to organization and methods of operation, may be best understood by reference to the following description, taken in conjunction with the accompanying drawings in which:

FIGS. 7A and 7B are views of the critical structure taken by the three-dimensional camera of FIG. 6, in which FIG. 7A is a view from a left-side lens of the three-dimensional camera and FIG. 7B is a view from a right-side lens of the three-dimensional camera, according to at least one aspect of the present disclosure.

FIG. 8 is a schematic of the surgical visualization system of FIG. 6, in which a camera-to-critical structure distance $d_w$ from the three-dimensional camera to the critical structure can be determined, according to at least one aspect of the present disclosure.

Figure 15C:
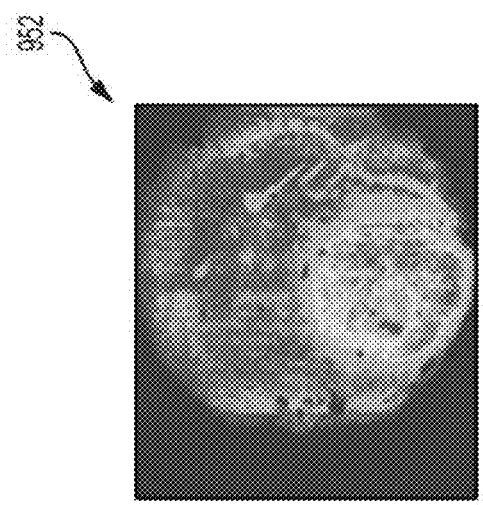
Figure 15B:
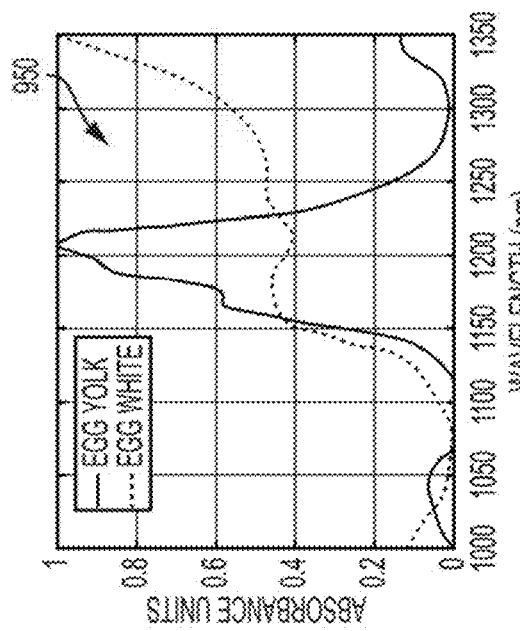
Figure 15A:
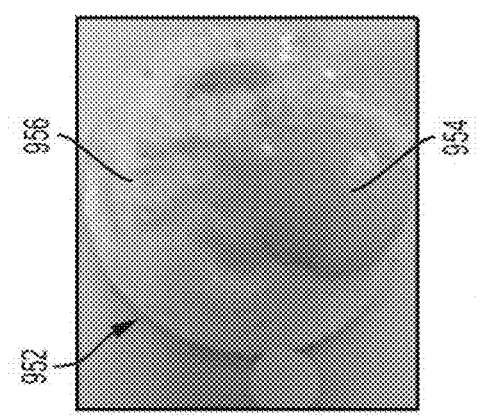

FIGS. 15A-15C show an example of a hyperspectral visualization system for imaging a fried egg, wherein FIG. 15A is a photograph of the fried egg, FIG. 15B is a graphical representation of hyperspectral signatures for an egg yolk portion and an egg white portion of the fried egg, and FIG. 15C is a hyperspectral image (shown in black-and-white) of the fried egg, in which an augmented image differentiates between the egg yolk portion and the egg white portion based on hyperspectral signature data, according to at least one aspect of the present disclosure.

FIGS. 16-18 illustrate illustrative hyperspectral identifying signatures to differentiate anatomy from obscurants, wherein FIG. 16 is a graphical representation of a ureter signature versus obscurants, FIG. 17 is a graphical representation of an artery signature versus obscurants, and FIG. 18 is a graphical representation of a nerve signature versus obscurants, according to at least one aspect of the present disclosure.

Figure 19:
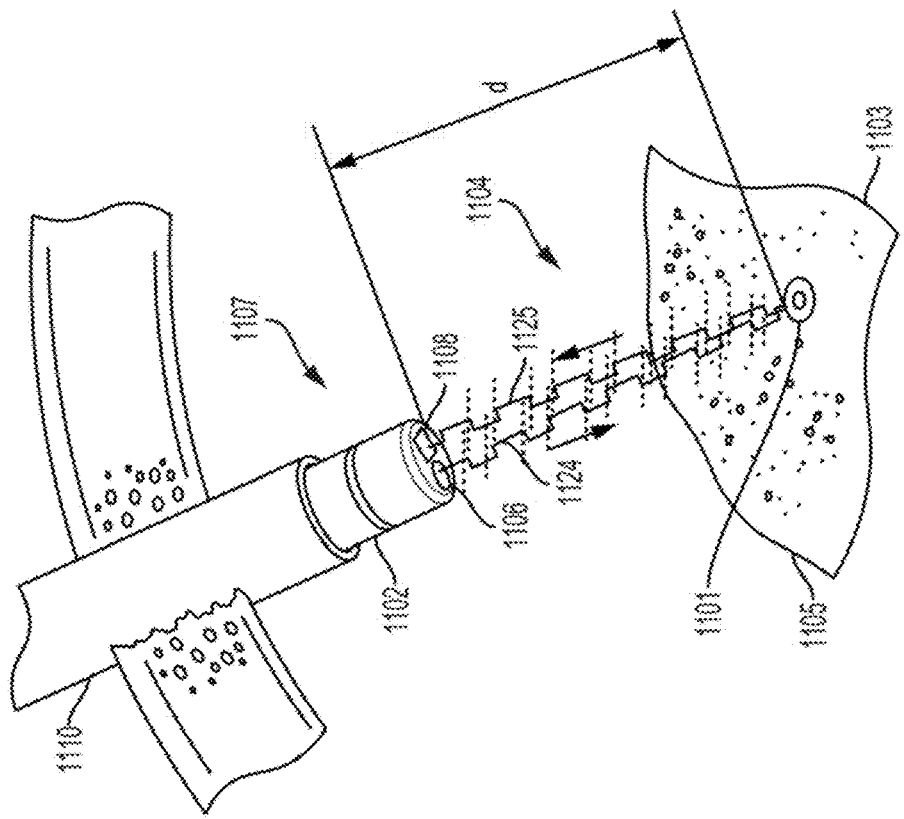

FIG. 19 is a schematic of a near infrared (NIR) time-of-flight measurement system configured to sense distance to a critical anatomical structure, the time-of-flight measurement system including a transmitter (emitter) and a receiver (sensor) positioned on a common device, according to at least one aspect of the present disclosure.

Figure 20:
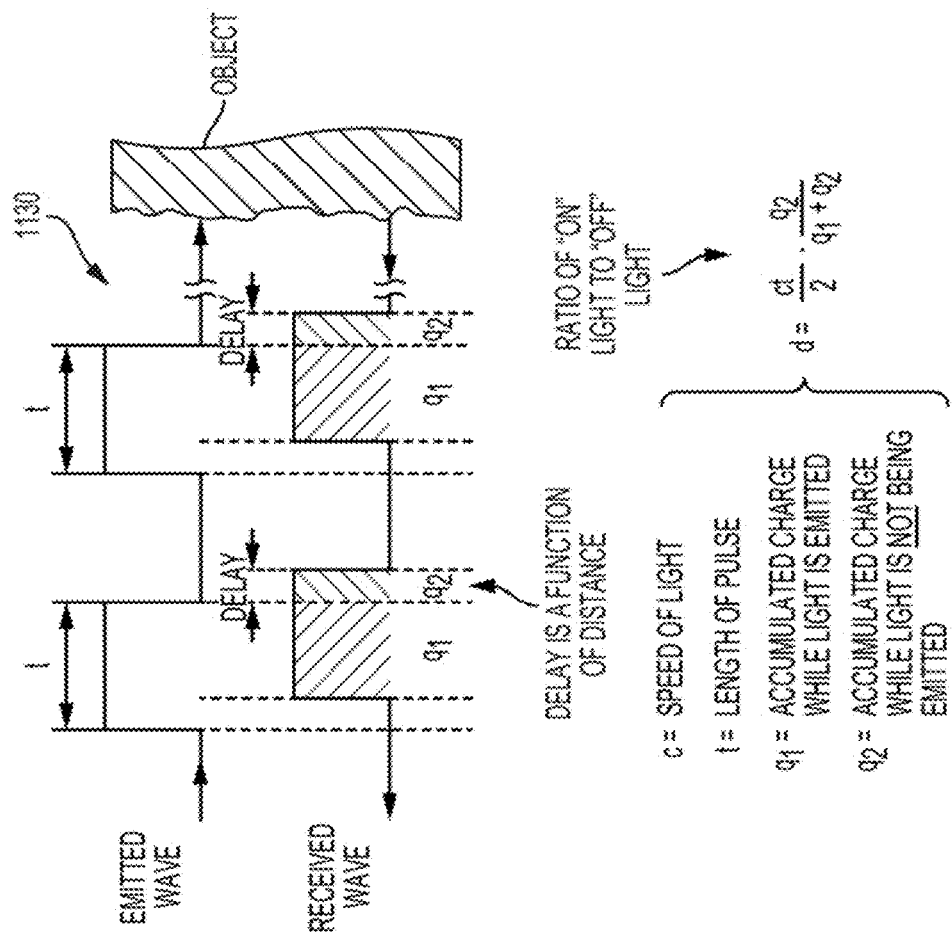

FIG. 20 is a schematic of an emitted wave, a received wave, and a delay between the emitted wave and the received wave of the NIR time-of-flight measurement system of FIG. 19, according to at least one aspect of the present disclosure.

Figure 21:
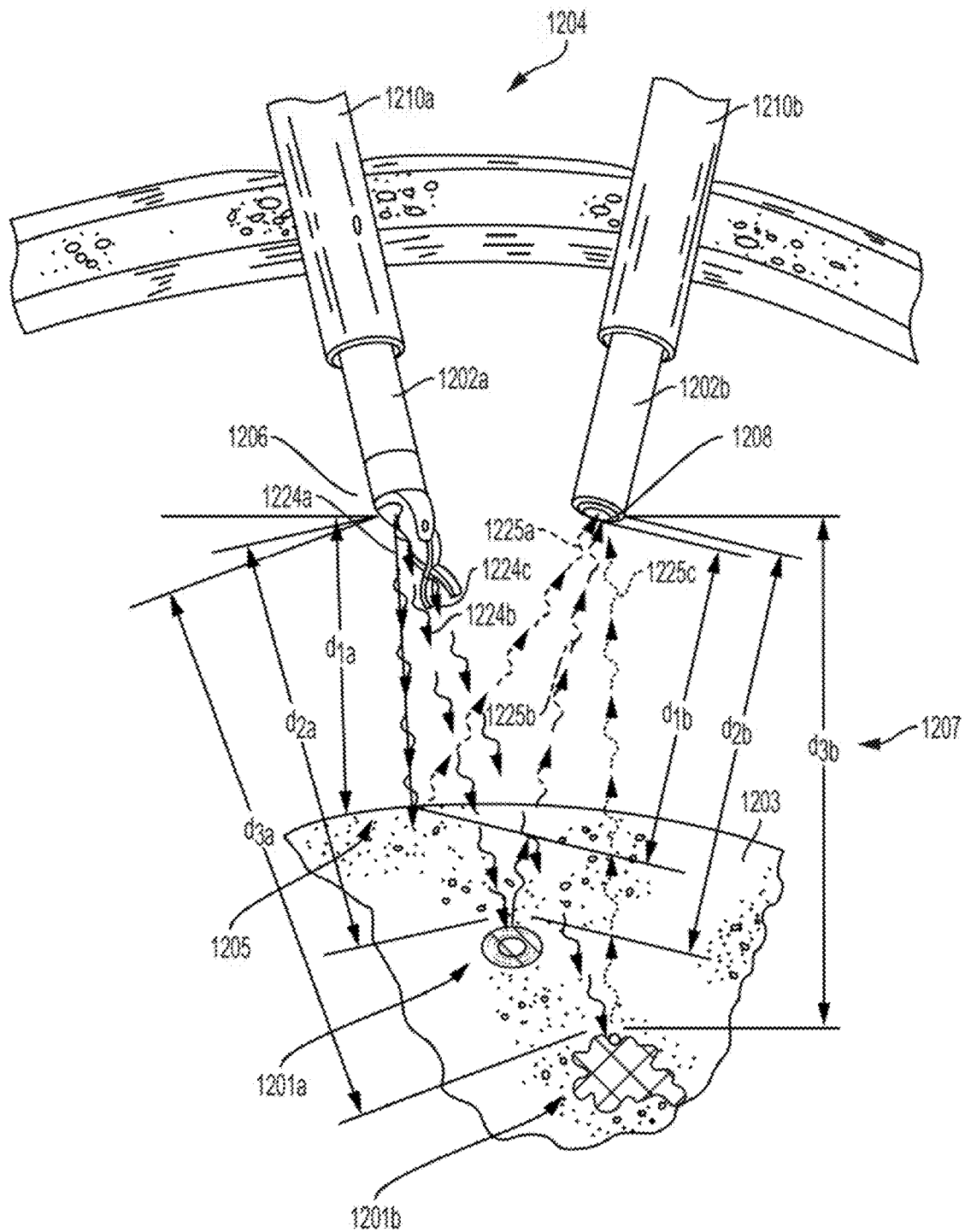

FIG. 21 illustrates a NIR time-of-flight measurement system configured to sense a distance to different structures, the time-of-flight measurement system including a transmitter (emitter) and a receiver (sensor) on separate devices, according to one aspect of the present disclosure.

Figure 22:
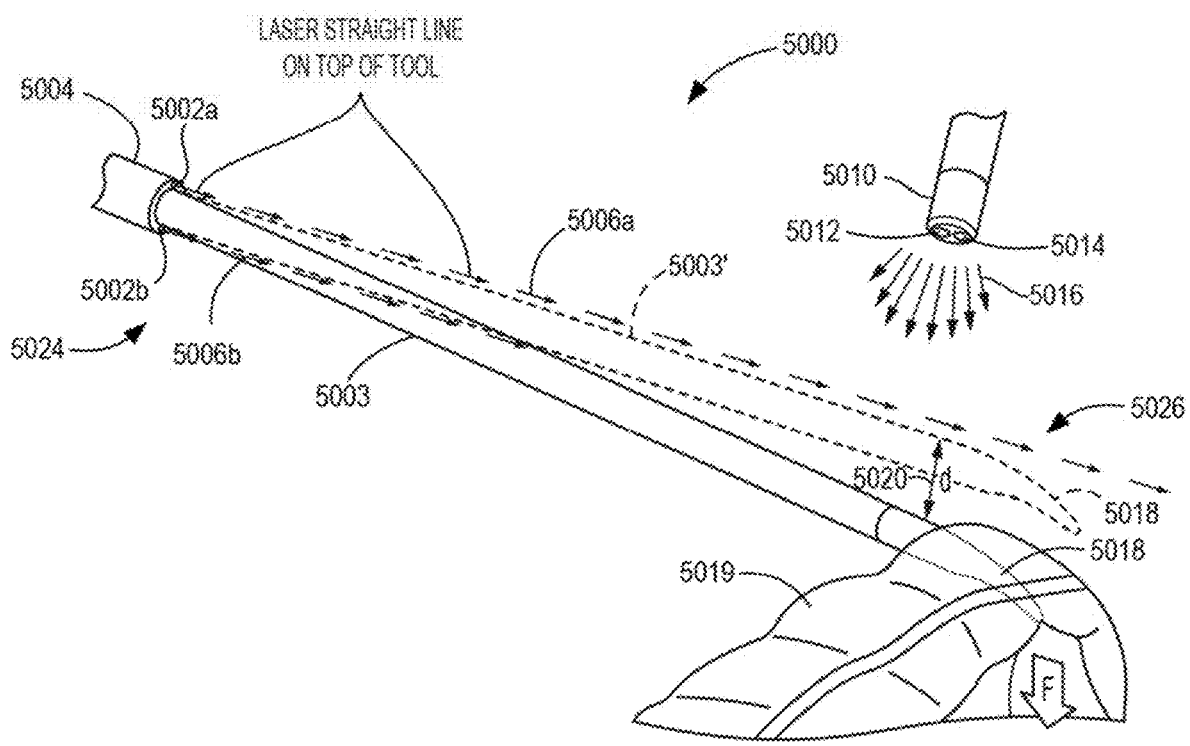
Figure 23:
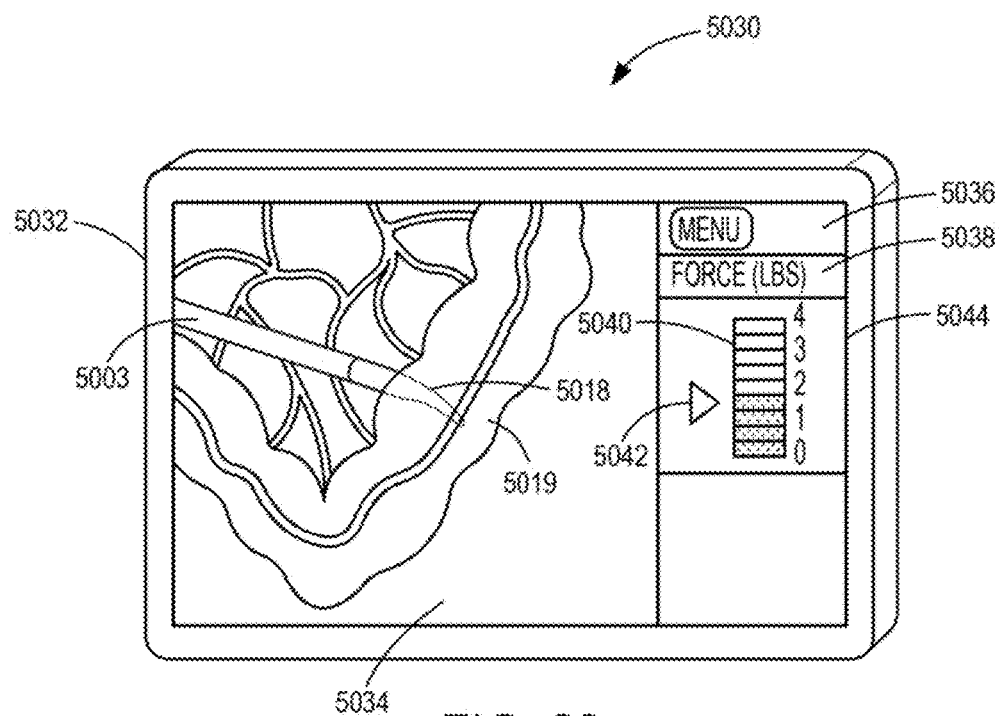
Figure 24:
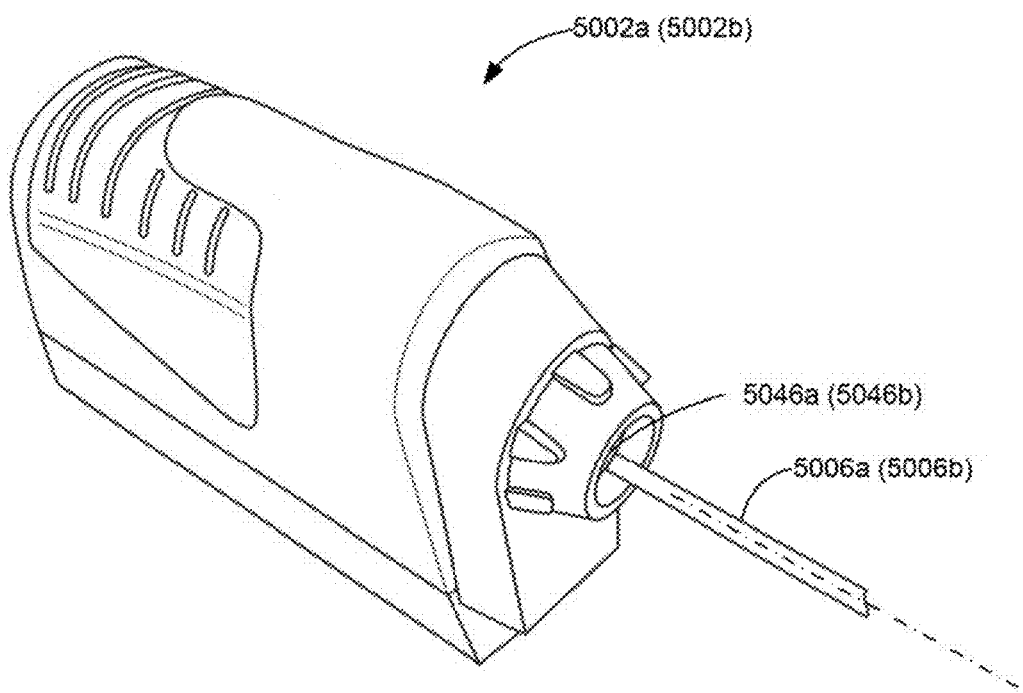

FIGS. 22-24 illustrate a force sensor through structured light deflection detection, according to at least one aspect of the present disclosure, where FIG. 22 illustrates a force sensor system through structured light deflection detection, according to at least one aspect of the present disclosure;

FIG. 23 is a video monitor displaying the surgical scene and the measured force, according to at least one aspect of the present disclosure; and FIG. 24 illustrates a reference straight line laser transmitter.

Figure 25:
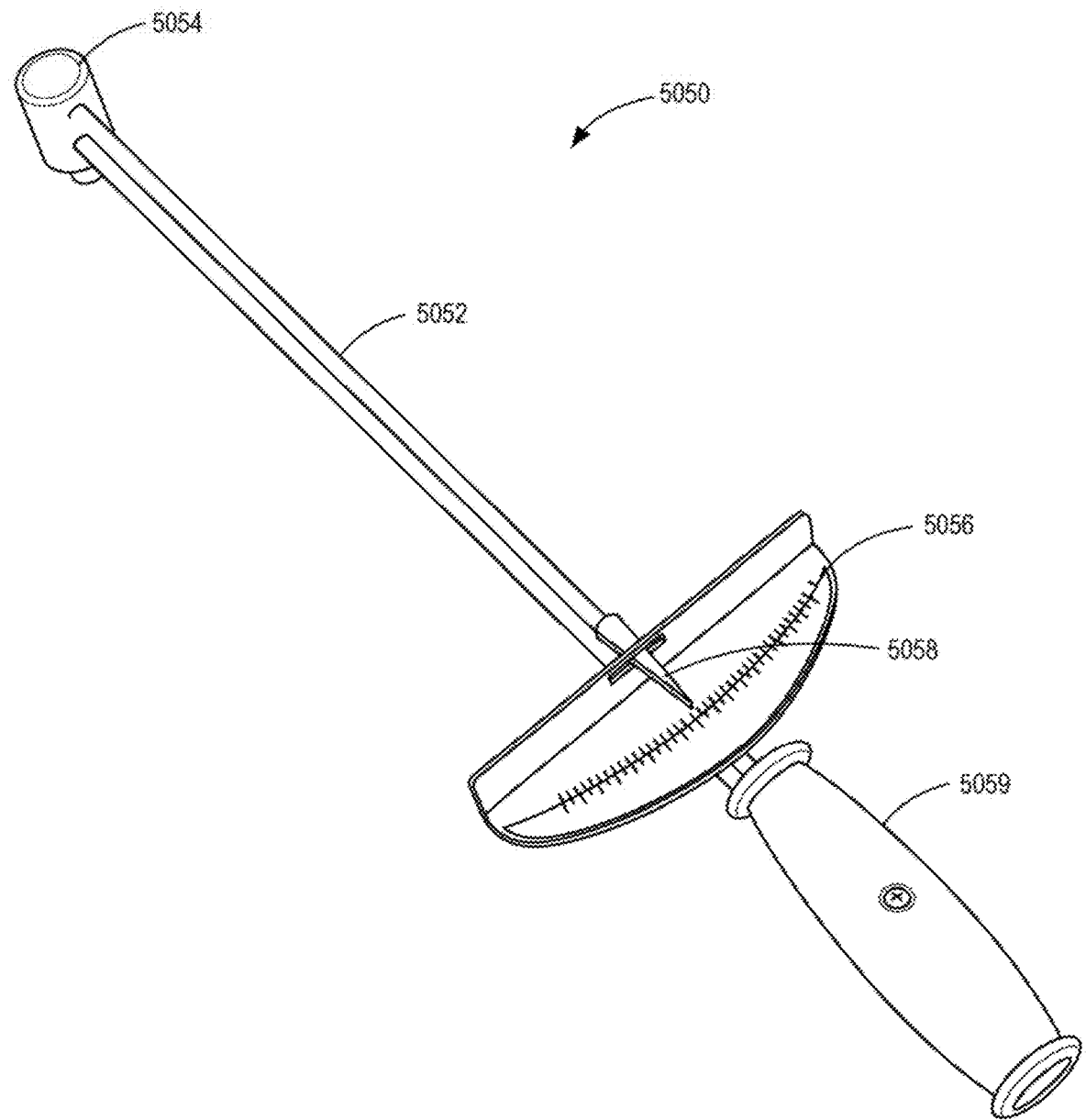

FIG. 25 illustrates a conventional deflection beam-style torque wrench.

Figure 26:
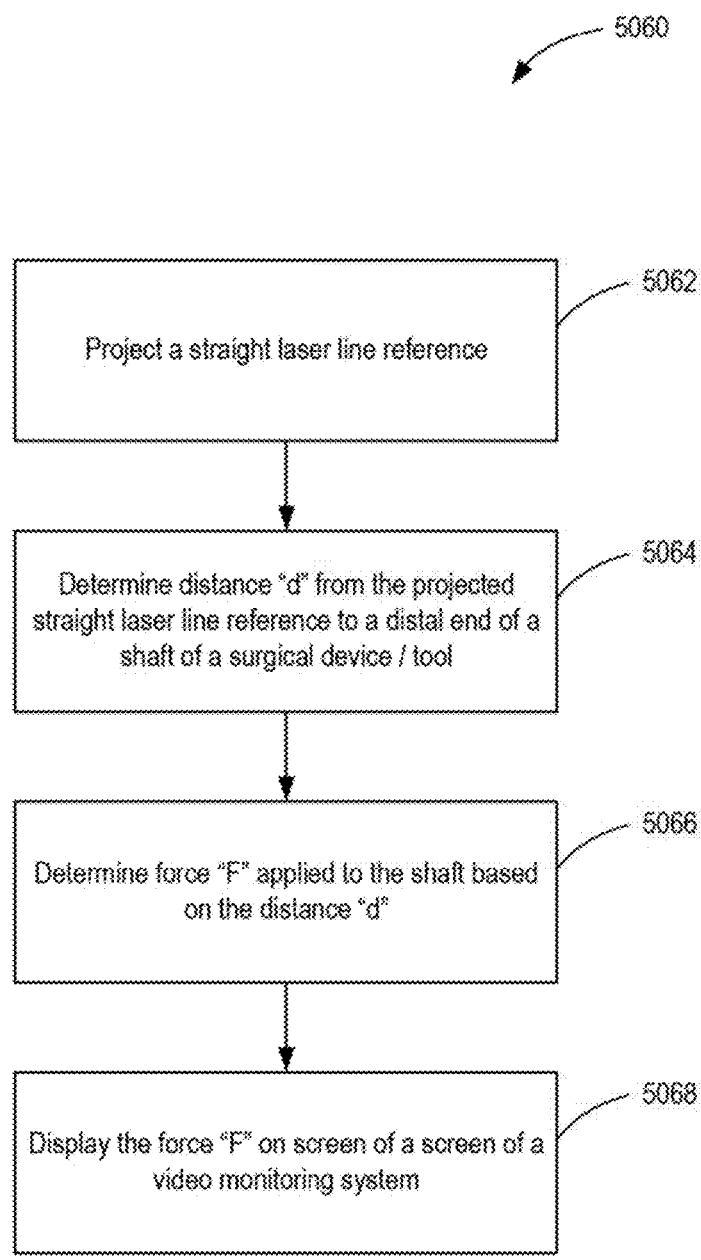

FIG. 26 illustrates a logic flow diagram of a process depicting a control program or a logic configuration to determine a force applied to a surgical instrument or tool using force sensor through structured light deflection detection, in accordance with at least one aspect of the present disclosure.

Figure 27A:
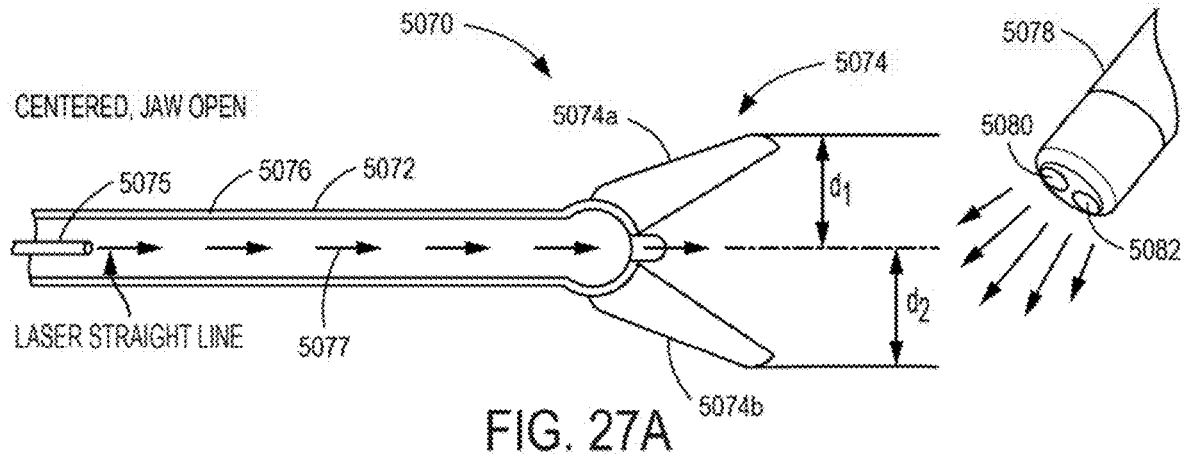
Figure 27B:
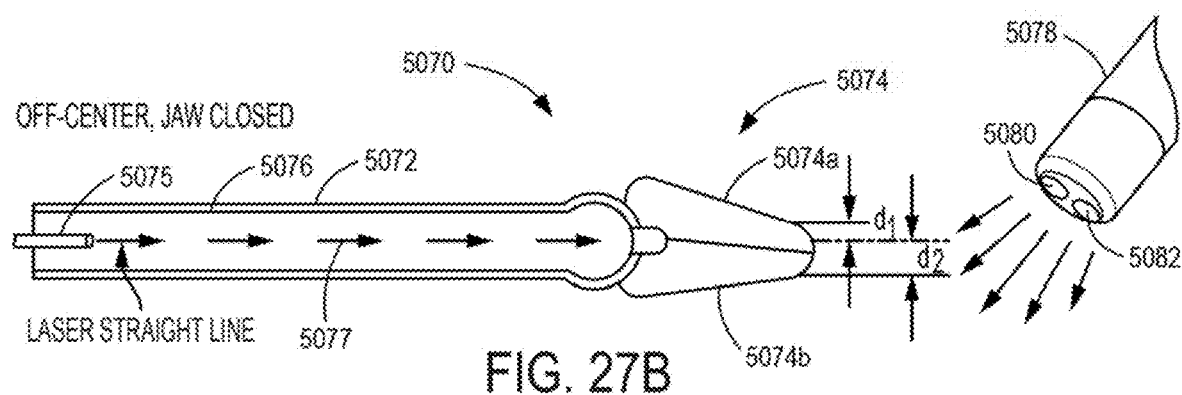
Figure 27C:
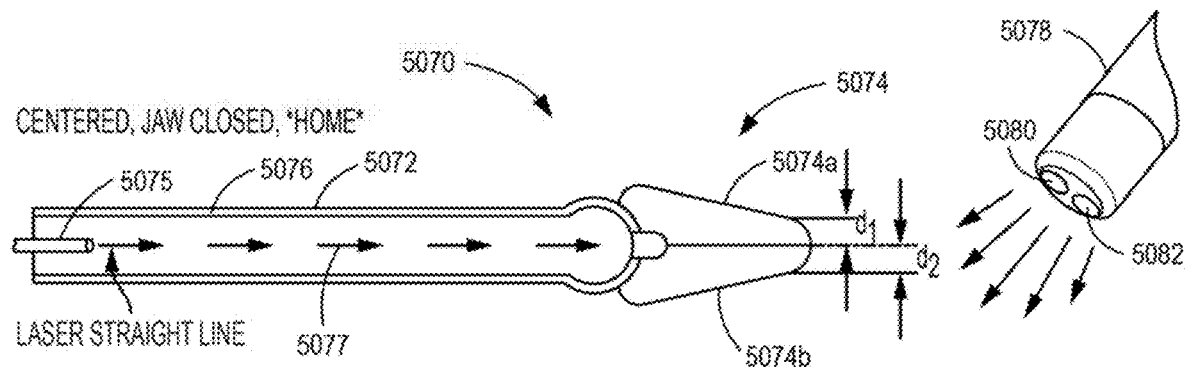

FIGS. 27A-27C illustrate jaw centering and homing indication system through structured light, according to at least one aspect of the present disclosure, where FIG. 27A illustrates a surgical device/tool with a centered jaw in the open position, according to at least one aspect of the present disclosure;

FIG. 27B illustrates a surgical device/tool with an off-center jaw in the closed position, according to at least one aspect of the present disclosure; and FIG. 27C illustrates a surgical device/tool with a centered jaw in the closed position, according to at least one aspect of the present disclosure.

Figure 28:
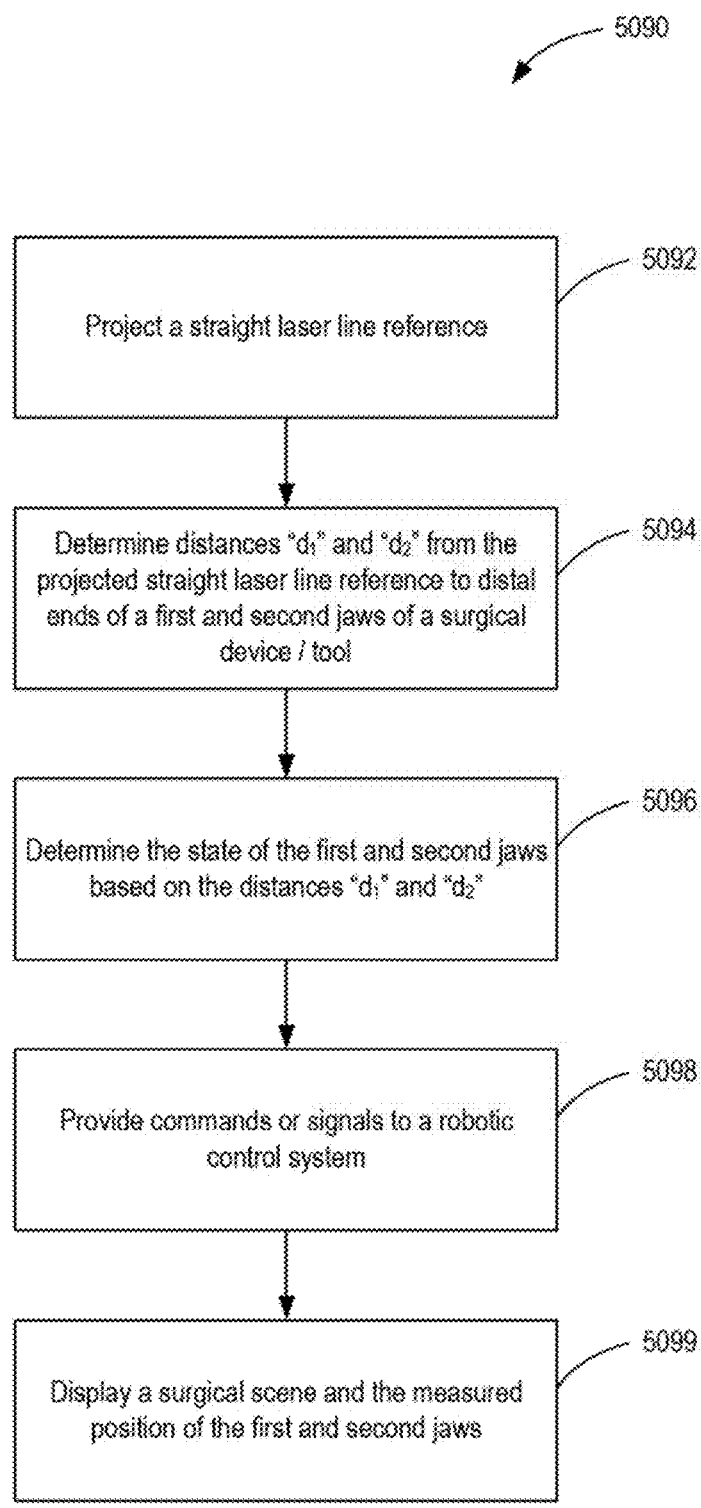

FIG. 28 illustrates a logic flow diagram of a process depicting a control program or a logic configuration to determine a jaw centering and homing indication of the surgical instrument or tool through structured light, in accordance with at least one aspect of the present disclosure.

Figure 29:
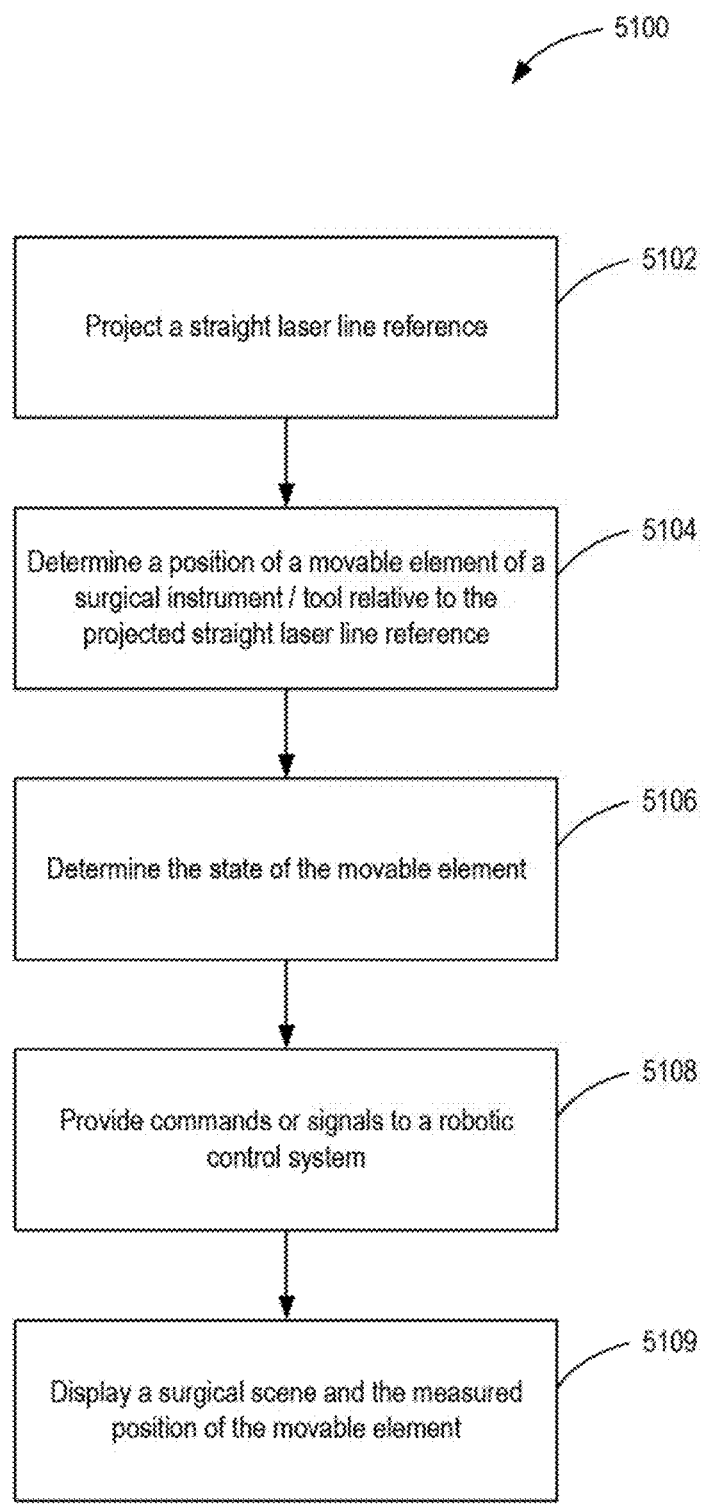

FIG. 29 illustrates a logic flow diagram of a process depicting a control program or a logic configuration to determine a position of a movable element of a surgical instrument or tool through structured light, in accordance with at least one aspect of the present disclosure.

DESCRIPTION

Applicant of the present application also owns the following U.S. Patent Applications, filed on September 11, 2018, each of which is herein incorporated by reference in its entirety:

U.S. patent application Ser. No. 16/128,179, titled SURGICAL VISUALIZATION PLATFORM, now U.S. Patent Application Publication No. 2020/0015923;

U.S. Patent Application Ser. No. 16/128,191, titled SURGICAL VISUALIZATION CONTROLS, now U.S. Patent Application Publication No. 2020/0015904;

U.S. Patent Application Ser. No. 16/128,180, titled CONTROLLING AN EMITTER ASSEMBLY PULSE SEQUENCE, now U.S. Patent Application Publication No. 2020/0015900;

U.S. Patent Application Ser. No. 16/128,198, titled COMBINATION EMITTER AND CAMERA ASSEMBLY, now U.S. Patent Application Publication No. 2020/0015668;

U.S. Patent Application Ser. No. 16/128,207, titled SINGULAR EMR SOURCE WITH DUAL OUTPUT EMITTER ASSEMBLY, now U.S. Patent Application Publication No. 2020/0015925;

U.S. Patent Application Ser. No. 16/128,176, titled SURGICAL VISUALIZATION WITH PROXIMITY TRACKING FEATURES, now U.S. Patent Application Publication No. 2020/0015899;

U.S. Patent Application Ser. No. 16/128,187, titled SURGICAL VISUALIZATION OF MULTIPLE TARGETS, now U.S. Patent Application Publication No. 2020/0015903;

U.S. Patent Application Ser. No. 16/128,192, titled VISUALIZATION OF SURGICAL DEVICES, now U.S. Patent Application Publication No. 2020/0015905;

U.S. Patent Application Ser. No. 16/128,163, titled OPERATIVE COMMUNICATION OF LIGHT, now U.S. Patent Application Publication No. 2020/0015897;

U.S. Patent Application Ser. No. 16/128,197, titled ROBOTIC LIGHT PROJECTION TOOLS, now U.S. Patent Application Publication No. 2020/0015924;

U.S. Patent Application Ser. No. 16/128,164, titled SURGICAL VISUALIZATION FEEDBACK SYSTEM, now U.S. Patent Application Publication No. 2020/0015898;

U.S. Patent Application Ser. No. 16/128,193, titled SURGICAL VISUALIZATION AND MONITORING, now U.S. Patent Application Publication No. 2020/0015906;

U.S. Patent Application Ser. No. 16/128,195, titled INTEGRATION OF IMAGING DATA, now U.S. Patent Application Publication No. 2020/0015907;

U.S. Patent Application Ser. No. 16/128,170, titled ROBOTICALLY-ASSISTED SURGICAL SUTURING SYSTEMS, now U.S. Patent Application Publication No. 2020/0015806;

U.S. Patent Application Ser. No. 16/128,183, titled SAFETY LOGIC FOR SURGICAL SUTURING SYSTEMS, now U.S. Patent Application Publication No. 2020/0015901;

U.S. Patent Application Ser. No. 16/128,172, titled ROBOTIC SYSTEM WITH SEPARATE PHOTOACOUSTIC RECEIVER, now U.S. Patent Application Publication No. 2020/0015914.

Applicant of the present application also owns U.S. Pat. No. 9,072,535, titled SURGICAL STAPLING INSTRUMENTS WITH ROTATABLE STAPLE DEPLOYMENT ARRANGEMENTS, issued Jul. 7, 2015, which is incorporated by reference herein in its entirety.

Applicant of the present application also owns U.S. Provisional Patent Application No. 62/611,339, titled ROBOT ASSISTED SURGICAL PLATFORM, filed Dec. 28, 2017, which is incorporated by reference herein in its entirety.

Applicant of the present application also owns the following U.S. Patent Applications, filed on Mar. 29, 2018, each of which is herein incorporated by reference in its entirety:

U.S. patent application Ser. No. 15/940,627, titled DRIVE ARRANGEMENTS FOR ROBOT-ASSISTED SURGICAL PLATFORMS;

U.S. patent application Ser. No. 15/940,676, titled AUTOMATIC TOOL ADJUSTMENTS FOR ROBOT-ASSISTED SURGICAL PLATFORMS;

U.S. patent application Ser. No. 15/940,711, titled SENSING ARRANGEMENTS FOR ROBOT-ASSISTED SURGICAL PLATFORMS; and U.S. patent application Ser. No. 15/940,722, titled CHARACTERIZATION OF TISSUE IRREGULARITIES THROUGH THE USE OF MONO-CHROMATIC LIGHT REFRACTIVITY, filed Mar. 29, 2018, which is incorporated by reference herein in its entirety.

Before explaining various aspects of a surgical visualization platform in detail, it should be noted that the illustrative examples are not limited in application or use to the details of construction and arrangement of parts illustrated in the accompanying drawings and description. The illustrative examples may be implemented or incorporated in other aspects, variations, and modifications, and may be practiced or carried out in various ways. Further, unless otherwise indicated, the terms and expressions employed herein have been chosen for the purpose of describing the illustrative examples for the convenience of the reader and are not for the purpose of limitation thereof. Also, it will be appreciated that one or more of the following-described aspects, expressions of aspects, and/or examples, can be combined with any one or more of the other following-described aspects, expressions of aspects, and/or examples.

The present disclosure is directed to a surgical visualization platform that leverages "digital surgery" to obtain additional information about a patient's anatomy and/or a surgical procedure. The surgical visualization platform is further configured to convey data and/or information to one or more clinicians in a helpful manner. For example, various aspects of the present disclosure provide improved visualization of the patient's anatomy and/or the surgical procedure.

"Digital surgery" can embrace robotic systems, advanced imaging, advanced instrumentation, artificial intelligence, machine learning, data analytics for performance tracking and benchmarking, connectivity both inside and outside of the operating room (OR), and more. Although various surgical visualization platforms described herein can be used in combination with a robotic surgical system, surgical visualization platforms are not limited to use with a robotic surgical system. In certain instances, advanced surgical visualization can occur without robotics and/or with limited and/or optional robotic assistance. Similarly, digital surgery can occur without robotics and/or with limited and/or optional robotic assistance.

In certain instances, a surgical system that incorporates a surgical visualization platform may enable smart dissection in order to identify and avoid critical structures. Critical structures include anatomical structures such as a ureter, an artery such as a superior mesenteric artery, a vein such as a portal vein, a nerve such as a phrenic nerve, and/or a tumor, among other anatomical structures. In other instances, a critical structure can be a foreign structure in the anatomical field, such as a surgical device, surgical fastener, clip, tack, bougie, band, and/or plate, for example. Critical structures can be determined on a patient-by-patient and/or a procedure-by-procedure basis. Example critical structures are further described herein. Smart dissection technology may provide improved intraoperative guidance for dissection and/or can enable smarter decisions with critical anatomy detection and avoidance technology, for example.

A surgical system incorporating a surgical visualization platform may also enable smart anastomosis technologies that provide more consistent anastomoses at optimal location(s) with improved workflow. Cancer localization technologies may also be improved with the various surgical visualization platforms and procedures described herein. For example, cancer localization technologies can identify and track a cancer location, orientation, and its margins. In certain instances, the cancer localizations technologies may compensate for movement of a tool, a patient, and/or the patient's anatomy during a surgical procedure in order to provide guidance back to the point of interest for the clinician.

In certain aspects of the present disclosure, a surgical visualization platform may provide improved tissue characterization and/or lymph node diagnostics and mapping. For example, tissue characterization technologies may characterize tissue type and health without the need for physical haptics, especially when dissecting and/or placing stapling devices within the tissue. Certain tissue characterization technologies described herein may be utilized without ionizing radiation and/or contrast agents. With respect to lymph node diagnostics and mapping, a surgical visualization platform may preoperatively locate, map, and ideally diagnose the lymph system and/or lymph nodes involved in cancerous diagnosis and staging, for example.

These and other related topics are described herein and/or in the aforementioned contemporaneously-filed U.S. Patent Applications, which are incorporated by reference herein in their respective entireties.

During a surgical procedure, the information available to the clinician via the "naked eye" and/or an imaging system may provide an incomplete view of the surgical site. For example, certain structures, such as structures embedded or buried within an organ, can be at least partially concealed or hidden from view. Additionally, certain dimensions and/or relative distances can be difficult to ascertain with existing sensor systems and/or difficult for the "naked eye" to perceive. Moreover, certain structures can move preoperatively (e.g. before a surgical procedure but after a preoperative scan) and/or intraoperatively. In such instances, the clinician can be unable to accurately determine the location of a critical structure intraoperatively.

When the position of a critical structure is uncertain and/or when the proximity between the critical structure and a surgical tool is unknown, a clinician's decision-making process can be inhibited. For example, a clinician may avoid certain areas in order to avoid inadvertent dissection of a critical structure; however, the avoided area may be unnecessarily large and/or at least partially misplaced. Due to uncertainty and/or overly/excessive exercises in caution, the clinician may not access certain desired regions. For example, excess caution may cause a clinician to leave a portion of a tumor and/or other undesirable tissue in an effort to avoid a critical structure even if the critical structure is not in the particular area and/or would not be negatively impacted by the clinician working in that particular area. In certain instances, surgical results can be improved with increased knowledge and/or certainty, which can allow a surgeon to be more accurate and, in certain instances, less conservative/more aggressive with respect to particular anatomical areas.

In various aspects, the present disclosure provides a surgical visualization system for intraoperative identification and avoidance of critical structures. In one aspect, the present disclosure provides a surgical visualization system that enables enhanced intraoperative decision making and improved surgical outcomes. In various aspects, the disclosed surgical visualization system provides advanced visualization capabilities beyond what a clinician sees with the "naked eye" and/or beyond what an imaging system can recognize and/or convey to the clinician. The various surgical visualization systems can augment and enhance what a clinician is able to know prior to tissue treatment (e.g. dissection) and, thus, may improve outcomes in various instances.

For example, a visualization system can include a first light emitter configured to emit a plurality of spectral waves, a second light emitter configured to emit a light pattern, and one or more receivers, or sensors, configured to detect visible light, molecular responses to the spectral waves (spectral imaging), and/or the light pattern. The surgical visualization system can also include an imaging system and a control circuit in signal communication with the receiver(s) and the imaging system. Based on output from the receiver(s), the control circuit can determine a geometric surface map, i.e. three-dimensional surface topography, of the visible surfaces at the surgical site and one or more distances with respect to the surgical site. In certain instances, the control circuit can determine one more distances to an at least partially concealed structure. Moreover, the imaging system can convey the geometric surface map and the one or more distances to a clinician. In such instances, an augmented view of the surgical site provided to the clinician can provide a representation of the concealed structure within the relevant context of the surgical site. For example, the imaging system can virtually augment the concealed structure on the geometric surface map of the concealing and/or obstructing tissue similar to a line drawn on the ground to indicate a utility line below the surface. Additionally or alternatively, the imaging system can convey the proximity of one or more surgical tools to the visible and obstructing tissue and/or to the at least partially concealed structure and/or the depth of the concealed structure below the visible surface of the obstructing tissue. For example, the visualization system can determine a distance with respect to the augmented line on the surface of the visible tissue and convey the distance to the imaging system.

In various aspects of the present disclosure, a surgical visualization system is disclosed for intraoperative identification and avoidance of critical structures. Such a surgical visualization system can provide valuable information to a clinician during a surgical procedure. As a result, the clinician can confidently maintain momentum throughout the surgical procedure knowing that the surgical visualization system is tracking a critical structure such as a ureter, specific nerves, and/or critical blood vessels, for example, which may be approached during dissection, for example. In one aspect, the surgical visualization system can provide an indication to the clinician in sufficient time for the clinician to pause and/or slow down the surgical procedure and evaluate the proximity to the critical structure to prevent inadvertent damage thereto. The surgical visualization system can provide an ideal, optimized, and/or customizable amount of information to the clinician to allow the clinician to move confidently and/or quickly through tissue while avoiding inadvertent damage to healthy tissue and/or critical structure(s) and, thus, to minimize the risk of harm resulting from the surgical procedure.

Figure 1:
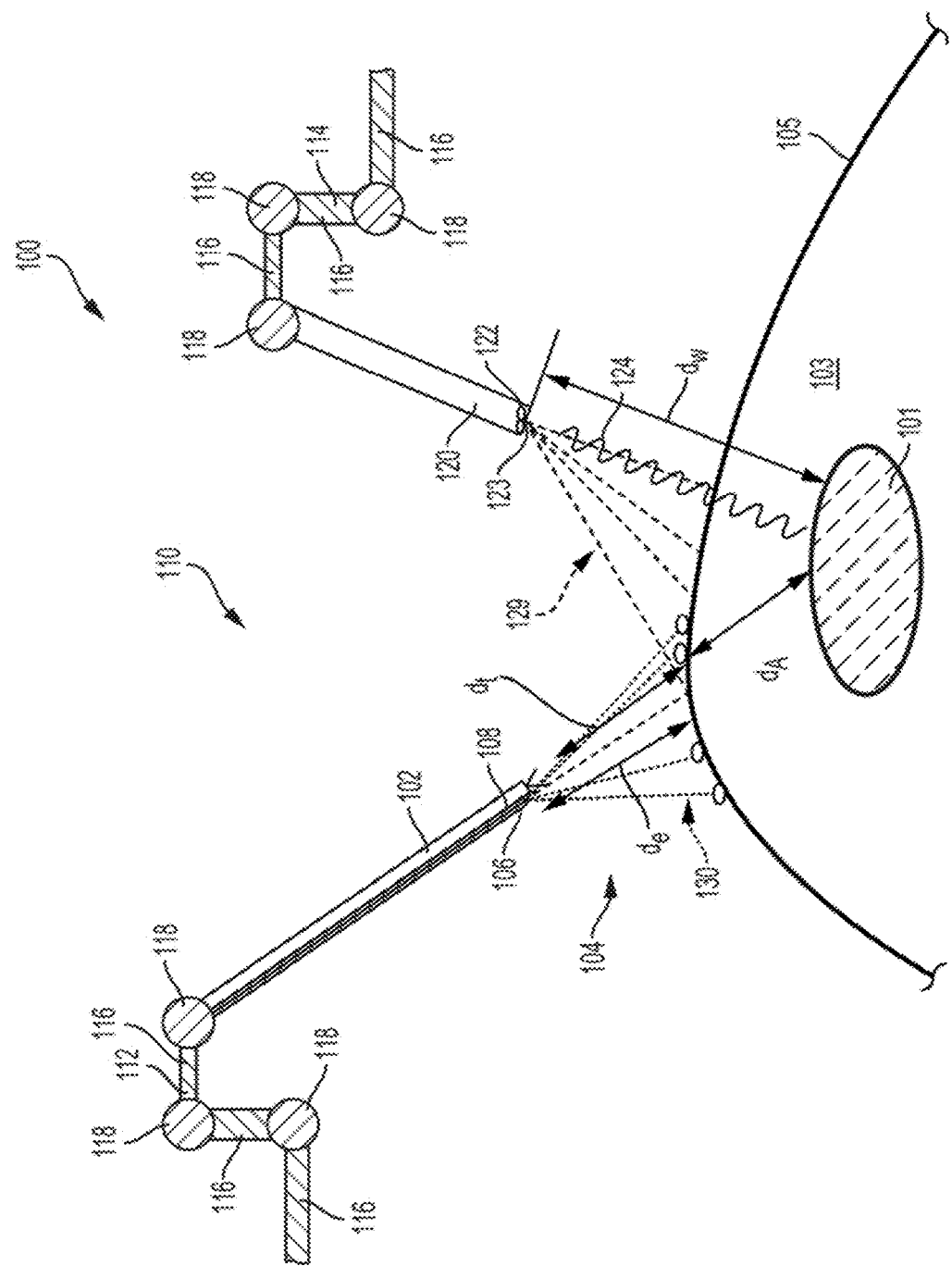
FIG. 1 is a schematic of a surgical visualization system including an imaging device and a surgical device, the surgical visualization system configured to identify a critical structure below a tissue surface, according to at least one aspect of the present disclosure.

FIG. 1 is a schematic of a surgical visualization system 100 according to at least one aspect of the present disclosure. The surgical visualization system 100 can create a visual representation of a critical structure 101 within an anatomical field. The surgical visualization system 100 can be used for clinical analysis and/or medical intervention, for example. In certain instances, the surgical visualization system 100 can be used intraoperatively to provide real-time, or near real-time, information to the clinician regarding proximity data, dimensions, and/or distances during a surgical procedure. The surgical visualization system 100 is configured for intraoperative identification of critical structure(s) and/or to facilitate the avoidance of the critical structure(s) 101 by a surgical device. For example, by identifying the critical structure 101, a clinician can avoid maneuvering a surgical device around the critical structure 101 and/or a region in a predefined proximity of the critical structure 101 during a surgical procedure. The clinician can avoid dissection of and/or near a vein, artery, nerve, and/or vessel, for example, identified as the critical structure 101, for example. In various instances, the critical structure 101 can be determined on a patient-by-patient and/or a procedure-by-procedure basis.

The surgical visualization system 100 incorporates tissue identification and geometric surface mapping in combination with a distance sensor system 104. In combination, these features of the surgical visualization system 100 can determine a position of a critical structure 101 within the anatomical field and/or the proximity of a surgical device 102 to the surface 105 of the visible tissue and/or to the critical structure 101. Moreover, the surgical visualization system 100 includes an imaging system that includes an imaging device 120, such as a camera, for example, configured to provide real-time views of the surgical site. In various instances, the imaging device 120 is a spectral camera (e.g. a hyperspectral camera, multispectral camera, or selective spectral camera), which is configured to detect reflected spectral waveforms and generate a spectral cube of images based on the molecular response to the different wavelengths. Views from the imaging device 120 can be provided to a clinician and, in various aspects of the present disclosure, can be augmented with additional information based on the tissue identification, landscape mapping, and the distance sensor system 104. In such instances, the surgical visualization system 100 includes a plurality of subsystems—an imaging subsystem, a surface mapping subsystem, a tissue identification subsystem, and/or a distance determining subsystem. These subsystems can cooperate to intraoperatively provide advanced data synthesis and integrated information to the clinician(s).

The imaging device can include a camera or imaging sensor that is configured to detect visible light, spectral light waves (visible or invisible), and a structured light pattern (visible or invisible), for example. In various aspects of the present disclosure, the imaging system can include an imaging device such as an endoscope, for example. Additionally or alternatively, the imaging system can include an imaging device such as an arthroscope, angioscope, bronchoscope, choledochoscope, colonoscope, cytoscope, duodenoscope, enteroscope, esophagogastro-duodenoscope (gastroscope), laryngoscope, nasopharyngo-neproscope, sigmoidoscope, thoracoscope, ureteroscope, or exoscope, for example. In other instances, such as in open surgery applications, the imaging system may not include a scope.

In various aspects of the present disclosure, the tissue identification subsystem can be achieved with a spectral imaging system. The spectral imaging system can rely on hyperspectral imaging, multispectral imaging, or selective spectral imaging, for example. Hyperspectral imaging of tissue is further described in U.S. Pat. No. 9,274,047, titled SYSTEM AND METHOD FOR GROSS ANATOMIC PATHOLOGY USING HYPERSPECTRAL IMAGING, issued Mar. 1, 2016, which is incorporated by reference herein in its entirety.

In various aspect of the present disclosure, the surface mapping subsystem can be achieved with a light pattern system, as further described herein. The use of a light pattern (or structured light) for surface mapping is known. Known surface mapping techniques can be utilized in the surgical visualization systems described herein.

Structured light is the process of projecting a known pattern (often a grid or horizontal bars) on to a surface. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, disclose a surgical system comprising a light source and a projector for projecting a light pattern. U.S. Patent Application Publication No. 2017/0055819, titled SET COMPRISING A SURGICAL INSTRUMENT, published Mar. 2, 2017, and U.S. Patent Application Publication No. 2017/0251900, titled DEPICTION SYSTEM, published Sep. 7, 2017, are incorporated by reference herein in their respective entireties.

In various aspects of the present disclosure, the distance determining system can be incorporated into the surface mapping system. For example, structured light can be utilized to generate a three-dimensional virtual model of the visible surface and determine various distances with respect to the visible surface. Additionally or alternatively, the distance determining system can rely on time-of-flight measurements to determine one or more distances to the identified tissue (or other structures) at the surgical site.

Figure 2:
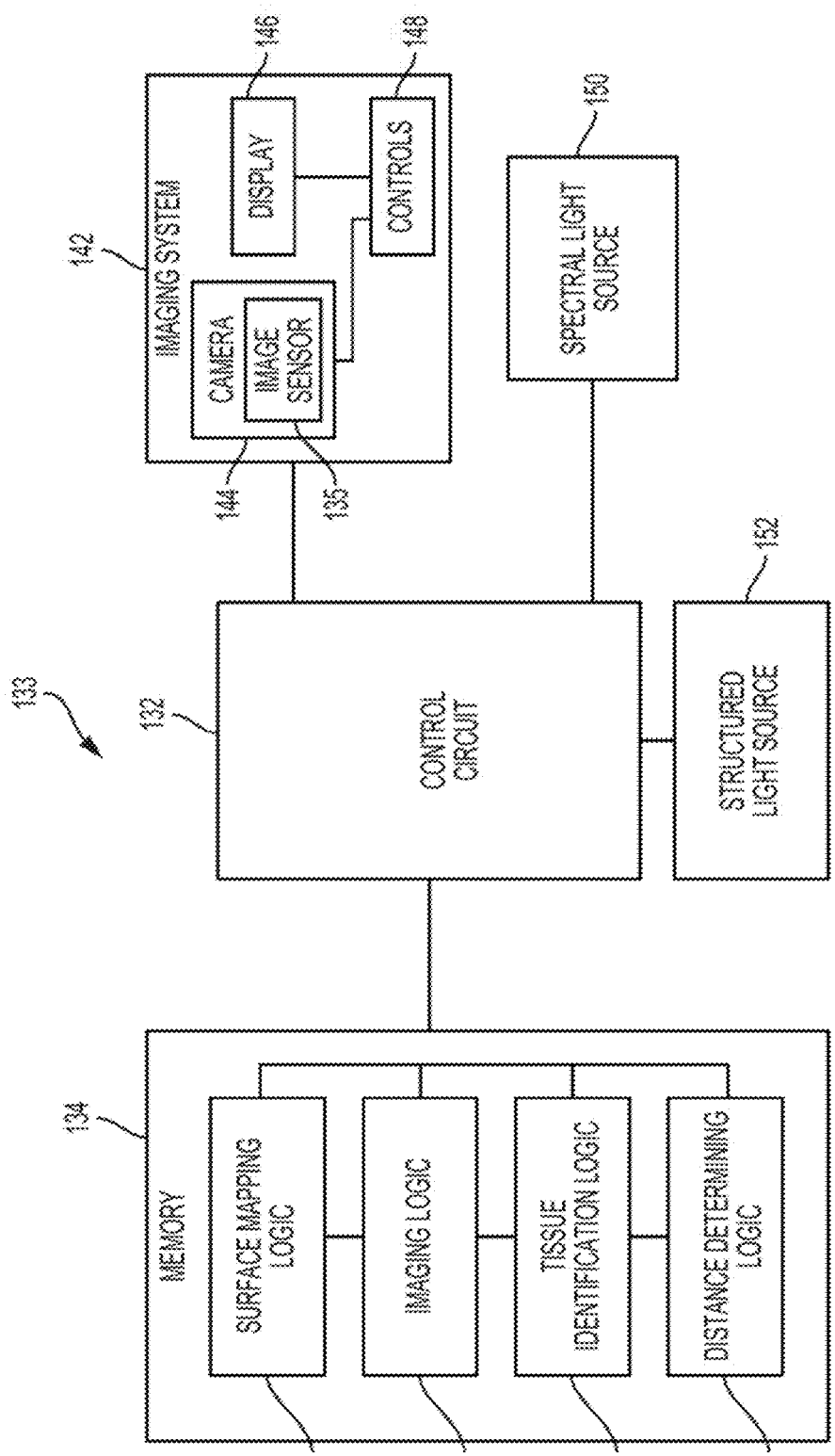
FIG. 2 is a schematic of a control system for a surgical visualization system, according to at least one aspect of the present disclosure.

FIG. 2 is a schematic diagram of a control system 133, which can be utilized with the surgical visualization system 100. The control system 133 includes a control circuit 132 in signal communication with a memory 134. The memory 134 stores instructions executable by the control circuit 132 to determine and/or recognize critical structures (e.g. the critical structure 101 in FIG. 1), determine and/or compute one or more distances and/or three-dimensional digital representations, and to communicate certain information to one or more clinicians. For example, the memory 134 stores surface mapping logic 136, imaging logic 138, tissue identification logic 140, or distance determining logic 141 or any combinations of the logic 136, 138, 140, and 141. The control system 133 also includes an imaging system 142 having one or more cameras 144 (like the imaging device 120 in FIG. 1), one or more displays 146, or one or more controls 148 or any combinations of these elements. The camera 144 can include one or more image sensors 135 to receive signals from various light sources emitting light at various visible and invisible spectra (e.g. visible light, spectral imagers, three-dimensional lens, among others). The display 146 can include one or more screens or monitors for depicting real, virtual, and/or virtually-augmented images and/or information to one or more clinicians.

In various aspects, the heart of the camera 144 is the image sensor 135. Generally, modern image sensors 135 are solid-state electronic devices containing up to millions of discrete photodetector sites called pixels. The image sensor 135 technology falls into one of two categories: Charge-Coupled Device (CCD) and Complementary Metal Oxide Semiconductor (CMOS) imagers and more recently, short-wave infrared (SWIR) is an emerging technology in imaging. Another type of image sensor 135 employs a hybrid CCD/CMOS architecture (sold under the name "sCMOS") and consists of CMOS readout integrated circuits (ROICs) that are bump bonded to a CCD imaging substrate. CCD and CMOS image sensors 135 are sensitive to wavelengths from approximately 350-1050 nm, although the range is usually given from 400-1000 nm. CMOS sensors are, in general, more sensitive to IR wavelengths than CCD sensors. Solid state image sensors 135 are based on the photoelectric effect and, as a result, cannot distinguish between colors. Accordingly, there are two types of color CCD cameras: single chip and three-chip. Single chip color CCD cameras offer a common, low-cost imaging solution and use a mosaic (e.g. Bayer) optical filter to separate incoming light into a series of colors and employ an interpolation algorithm to resolve full color images. Each color is, then, directed to a different set of pixels. Three-chip color CCD cameras provide higher resolution by employing a prism to direct each section of the incident spectrum to a different chip. More accurate color reproduction is possible, as each point in space of the object has separate RGB intensity values, rather than using an algorithm to determine the color. Three-chip cameras offer extremely high resolutions.

The control system 133 also includes a spectral light source 150 and a structured light source 152. In certain instances, a single source can be pulsed to emit wavelengths of light in the spectral light source 150 range and wavelengths of light in the structured light source 152 range. Alternatively, a single light source can be pulsed to provide light in the invisible spectrum (e.g. infrared spectral light) and wavelengths of light on the visible spectrum. The spectral light source 150 can be a hyperspectral light source, a multispectral light source, and/or a selective spectral light source, for example. In various instances, the tissue identification logic 140 can identify critical structure(s) via data from the spectral light source 150 received by the image sensor 135 portion of the camera 144. The surface mapping logic 136 can determine the surface contours of the visible tissue based on reflected structured light. With time-of-flight measurements, the distance determining logic 141 can determine one or more distance(s) to the visible tissue and/or the critical structure 101. One or more outputs from the surface mapping logic 136, the tissue identification logic 140, and the distance determining logic 141, can be provided to the imaging logic 138, and combined, blended, and/or overlaid to be conveyed to a clinician via the display 146 of the imaging system 142.

Figure 2A:
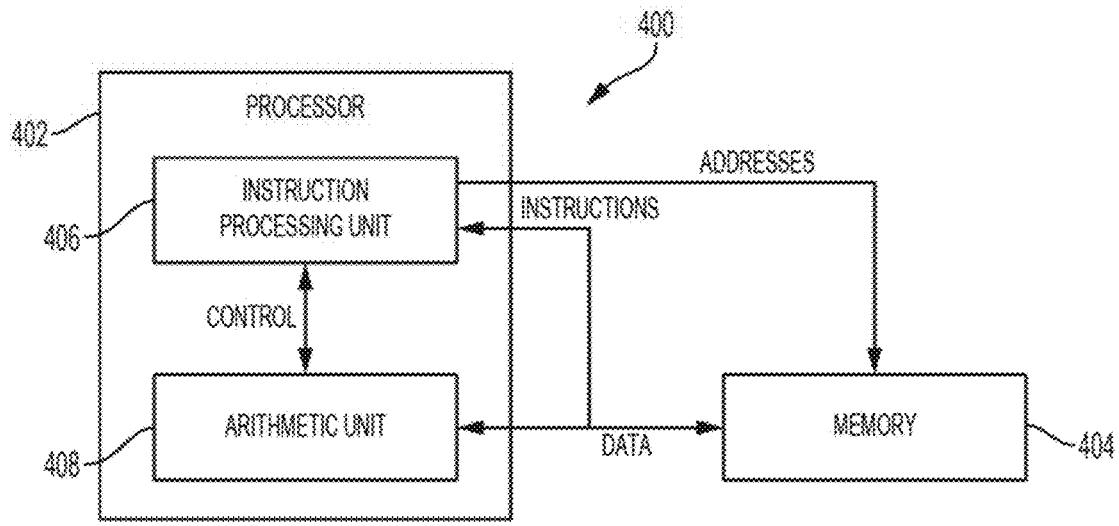
FIG. 2A illustrates a control circuit configured to control aspects of a surgical visualization system, according to at least one aspect of the present disclosure.
Figure 2B:
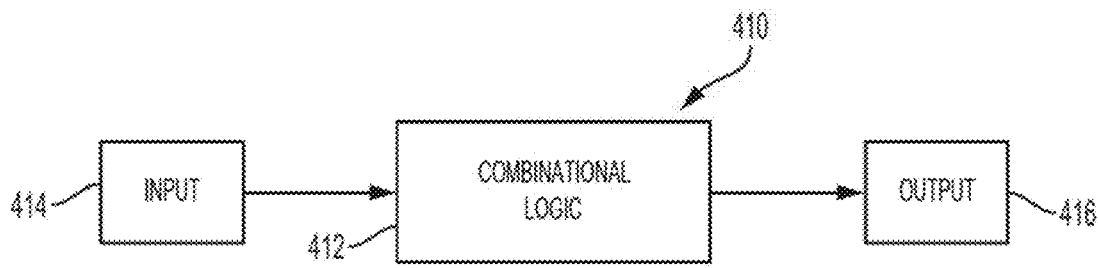
FIG. 2B illustrates a combinational logic circuit configured to control aspects of a surgical visualization system, according to at least one aspect of the present disclosure.
Figure 2C:
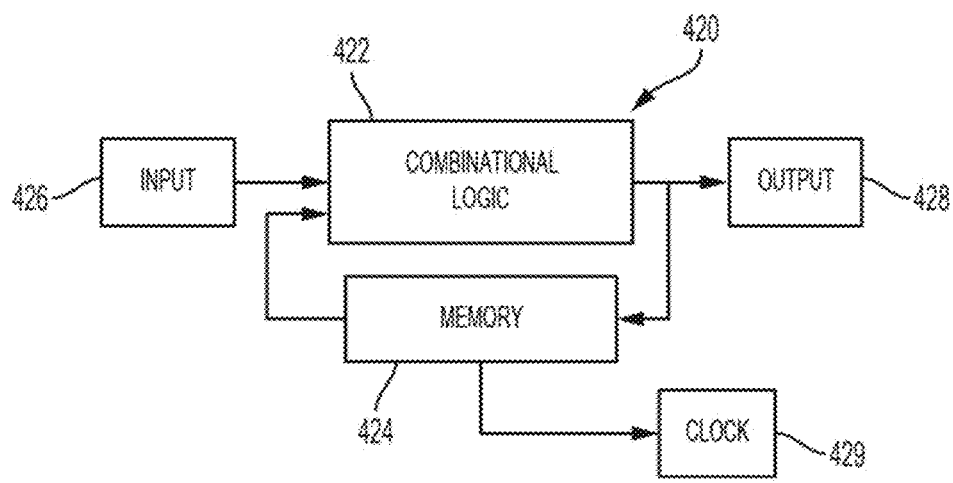
FIG. 2C illustrates a sequential logic circuit configured to control aspects of a surgical visualization system, according to at least one aspect of the present disclosure.

The description now turns briefly to FIGS. 2A-2C to describe various aspects of the control circuit 132 for controlling various aspects of the surgical visualization system 100. Turning to FIG. 2A, there is illustrated a control circuit 400 configured to control aspects of the surgical visualization system 100, according to at least one aspect of this disclosure. The control circuit 400 can be configured to implement various processes described herein. The control circuit 400 may comprise a microcontroller comprising one or more processors 402 (e.g., microprocessor, microcontroller) coupled to at least one memory circuit 404. The memory circuit 404 stores machine-executable instructions that, when executed by the processor 402, cause the processor 402 to execute machine instructions to implement various processes described herein. The processor 402 may be any one of a number of single-core or multicore processors known in the art. The memory circuit 404 may comprise volatile and non-volatile storage media. The processor 402 may include an instruction processing unit 406 and an arithmetic unit 408. The instruction processing unit may be configured to receive instructions from the memory circuit 404 of this disclosure.

FIG. 2B illustrates a combinational logic circuit 410 configured to control aspects of the surgical visualization system 100, according to at least one aspect of this disclosure. The combinational logic circuit 410 can be configured to implement various processes described herein. The combinational logic circuit 410 may comprise a finite state machine comprising a combinational logic 412 configured to receive data associated with the surgical instrument or tool at an input 414, process the data by the combinational logic 412, and provide an output 416.

FIG. 2C illustrates a sequential logic circuit 420 configured to control aspects of the surgical visualization system 100, according to at least one aspect of this disclosure. The sequential logic circuit 420 or the combinational logic 422 can be configured to implement various processes described herein. The sequential logic circuit 420 may comprise a finite state machine. The sequential logic circuit 420 may comprise a combinational logic 422, at least one memory circuit 424, and a clock 429, for example. The at least one memory circuit 424 can store a current state of the finite state machine. In certain instances, the sequential logic circuit 420 may be synchronous or asynchronous. The combinational logic 422 is configured to receive data associated with a surgical device or system from an input 426, process the data by the combinational logic 422, and provide an output 428. In other aspects, the circuit may comprise a combination of a processor (e.g., processor 402 in FIG. 2A) and a finite state machine to implement various processes herein. In other aspects, the finite state machine may comprise a combination of a combinational logic circuit (e.g., combinational logic circuit 410, FIG. 2B) and the sequential logic circuit 420.

Referring again to the surgical visualization system 100 in FIG. 1, the critical structure 101 can be an anatomical structure of interest. For example, the critical structure 101 can be a ureter, an artery such as a superior mesenteric artery, a vein such as a portal vein, a nerve such as a phrenic nerve, and/or a tumor, among other anatomical structures. In other instances, the critical structure 101 can be a foreign structure in the anatomical field, such as a surgical device, surgical fastener, clip, tack, bougie, band, and/or plate, for example. Example critical structures are further described herein and in the aforementioned contemporaneously-filed U.S. Patent Applications, including U.S. patent application Ser. No. 16/128,192, titled VISUALIZATION OF SURGICAL DEVICES, now U.S. Patent Application Publication No. 2020/0015905, for example, which are incorporated by reference herein in their respective entireties.

In one aspect, the critical structure 101 may be embedded in tissue 103. Stated differently, the critical structure 101 may be positioned below the surface 105 of the tissue 103. In such instances, the tissue 103 conceals the critical structure 101 from the clinician's view. The critical structure 101 is also obscured from the view of the imaging device 120 by the tissue 103. The tissue 103 can be fat, connective tissue, adhesions, and/or organs, for example. In other instances, the critical structure 101 can be partially obscured from view.

FIG. 1 also depicts the surgical device 102. The surgical device 102 includes an end effector having opposing jaws extending from the distal end of the shaft of the surgical device 102. The surgical device 102 can be any suitable surgical device such as, for example, a dissector, a stapler, a grasper, a clip applier, and/or an energy device including mono-polar probes, bi-polar probes, ablation probes, and/or an ultrasonic end effector. Additionally or alternatively, the surgical device 102 can include another imaging or diagnostic modality, such as an ultrasound device, for example. In one aspect of the present disclosure, the surgical visualization system 100 can be configured to achieve identification of one or more critical structures 101 and the proximity of the surgical device 102 to the critical structure(s) 101.

The imaging device 120 of the surgical visualization system 100 is configured to detect light at various wavelengths, such as, for example, visible light, spectral light waves (visible or invisible), and a structured light pattern (visible or invisible). The imaging device 120 may include a plurality of lenses, sensors, and/or receivers for detecting the different signals. For example, the imaging device 120 can be a hyperspectral, multispectral, or selective spectral camera, as further described herein. The imaging device 120 can also include a waveform sensor 122 (such as a spectral image sensor, detector, and/or three-dimensional camera lens). For example, the imaging device 120 can include a right-side lens and a left-side lens used together to record two two-dimensional images at the same time and, thus, generate a three-dimensional image of the surgical site, render a three-dimensional image of the surgical site, and/or determine one or more distances at the surgical site. Additionally or alternatively, the imaging device 120 can be configured to receive images indicative of the topography of the visible tissue and the identification and position of hidden critical structures, as further described herein. For example, the field of view of the imaging device 120 can overlap with a pattern of light (structured light) on the surface 105 of the tissue, as shown in FIG. 1.

In one aspect, the surgical visualization system 100 may be incorporated into a robotic system 110. For example, the robotic system 110 may include a first robotic arm 112 and a second robotic arm 114. The robotic arms 112, 114 include rigid structural members 116 and joints 118, which can include servomotor controls. The first robotic arm 112 is configured to maneuver the surgical device 102, and the second robotic arm 114 is configured to maneuver the imaging device 120. A robotic control unit can be configured to issue control motions to the robotic arms 112, 114, which can affect the surgical device 102 and the imaging device 120, for example.

The surgical visualization system 100 also includes an emitter 106, which is configured to emit a pattern of light, such as stripes, grid lines, and/or dots, to enable the determination of the topography or landscape of the surface 105. For example, projected light arrays 130 can be used for three-dimensional scanning and registration on the surface 105. The projected light arrays 130 can be emitted from the emitter 106 located on the surgical device 102 and/or one of the robotic arms 112, 114 and/or the imaging device 120, for example. In one aspect, the projected light array 130 is employed to determine the shape defined by the surface 105 of the tissue 103 and/or the motion of the surface 105 intraoperatively. The imaging device 120 is configured to detect the projected light arrays 130 reflected from the surface 105 to determine the topography of the surface 105 and various distances with respect to the surface 105.

In one aspect, the imaging device 120 also may include an optical waveform emitter 123 that is configured to emit electromagnetic radiation 124 (NIR photons) that can penetrate the surface 105 of the tissue 103 and reach the critical structure 101. The imaging device 120 and the optical waveform emitter 123 thereon can be positionable by the robotic arm 114. A corresponding waveform sensor 122 (an image sensor, spectrometer, or vibrational sensor, for example) on the imaging device 120 is configured to detect the effect of the electromagnetic radiation received by the waveform sensor 122. The wavelengths of the electromagnetic radiation 124 emitted by the optical waveform emitter 123 can be configured to enable the identification of the type of anatomical and/or physical structure, such as the critical structure 101. The identification of the critical structure 101 can be accomplished through spectral analysis, photo-acoustics, and/or ultrasound, for example. In one aspect, the wavelengths of the electromagnetic radiation 124 may be variable. The waveform sensor 122 and optical waveform emitter 123 may be inclusive of a multispectral imaging system and/or a selective spectral imaging system, for example. In other instances, the waveform sensor 122 and optical waveform emitter 123 may be inclusive of a photoacoustic imaging system, for example. In other instances, the optical waveform emitter 123 can be positioned on a separate surgical device from the imaging device 120.

The surgical visualization system 100 also may include the distance sensor system 104 configured to determine one or more distances at the surgical site. In one aspect, the time-of-flight distance sensor system 104 may be a time-of-flight distance sensor system that includes an emitter, such as the emitter 106, and a receiver 108, which can be positioned on the surgical device 102. In other instances, the time-of-flight emitter can be separate from the structured light emitter. In one general aspect, the emitter 106 portion of the time-of-flight distance sensor system 104 may include a very tiny laser source and the receiver 108 portion of the time-of-flight distance sensor system 104 may include a matching sensor. The time-of-flight distance sensor system 104 can detect the "time of flight," or how long the laser light emitted by the emitter 106 has taken to bounce back to the sensor portion of the receiver 108. Use of a very narrow light source in the emitter 106 enables the distance sensor system 104 to determining the distance to the surface 105 of the tissue 103 directly in front of the distance sensor system 104. Referring still to FIG. 1, $d_e$ is the emitter-to-tissue distance from the emitter 106 to the surface 105 of the tissue 103 and $d_t$ is the device-to-tissue distance from the distal end of the surgical device 102 to the surface 105 of the tissue. The distance sensor system 104 can be employed to determine the emitter-to-tissue distance $d_e$. The device-to-tissue distance $d_t$ is obtainable from the known position of the emitter 106 on the shaft of the surgical device 102 relative to the distal end of the surgical device 102. In other words, when the distance between the emitter 106 and the distal end of the surgical device 102 is known, the device-to-tissue distance $d_t$ can be determined from the emitter-to-tissue distance $d_e$. In certain instances, the shaft of the surgical device 102 can include one or more articulation joints, and can be articulatable with respect to the emitter 106 and the jaws. The articulation configuration can include a multi-joint vertebrae-like structure, for example. In certain instances, a three-dimensional camera can be utilized to triangulate one or more distances to the surface 105.

In various instances, the receiver 108 for the time-of-flight distance sensor system 104 can be mounted on a separate surgical device instead of the surgical device 102. For example, the receiver 108 can be mounted on a cannula or trocar through which the surgical device 102 extends to reach the surgical site. In still other instances, the receiver 108 for the time-of-flight distance sensor system 104 can be mounted on a separate robotically-controlled arm (e.g. the robotic arm 114), on a movable arm that is operated by another robot, and/or to an operating room (OR) table or fixture. In certain instances, the imaging device 120 includes the time-of-flight receiver 108 to determine the distance from the emitter 106 to the surface 105 of the tissue 103 using a line between the emitter 106 on the surgical device 102 and the imaging device 120. For example, the distance $d_e$ can be triangulated based on known positions of the emitter 106 (on the surgical device 102) and the receiver 108 (on the imaging device 120) of the time-of-flight distance sensor system 104. The three-dimensional position of the receiver 108 can be known and/or registered to the robot coordinate plane intraoperatively.

In certain instances, the position of the emitter 106 of the time-of-flight distance sensor system 104 can be controlled by the first robotic arm 112 and the position of the receiver 108 of the time-of-flight distance sensor system 104 can be controlled by the second robotic arm 114. In other instances, the surgical visualization system 100 can be utilized apart from a robotic system. In such instances, the distance sensor system 104 can be independent of the robotic system.

In certain instances, one or more of the robotic arms 112, 114 may be separate from a main robotic system used in the surgical procedure. At least one of the robotic arms 112, 114 can be positioned and registered to a particular coordinate system without a servomotor control. For example, a closed-loop control system and/or a plurality of sensors for the robotic arms 110 can control and/or register the position of the robotic arm(s) 112, 114 relative to the particular coordinate system. Similarly, the position of the surgical device 102 and the imaging device 120 can be registered relative to a particular coordinate system.

Figure 3:
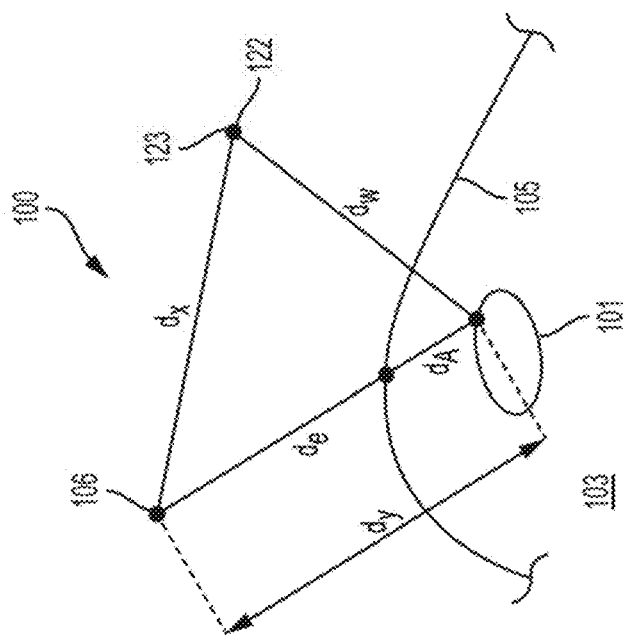
FIG. 3 is a schematic depicting triangularization between the surgical device, the imaging device, and the critical structure of FIG. 1 to determine a depth $d_A$ of the critical structure below the tissue surface, according to at least one aspect of the present disclosure.

Referring still to FIG. 1, $d_w$ is the camera-to-critical structure distance from the optical waveform emitter 123 located on the imaging device 120 to the surface of the critical structure 101, and $d_A$ is the depth of the critical structure 101 below the surface 105 of the tissue 103 (i.e., the distance between the portion of the surface 105 closest to the surgical device 102 and the critical structure 101). In various aspects, the time-of-flight of the optical waveforms emitted from the optical waveform emitter 123 located on the imaging device 120 can be configured to determine the camera-to-critical structure distance $d_w$. The use of spectral imaging in combination with time-of-flight sensors is further described herein. Moreover, referring now to FIG. 3, in various aspects of the present disclosure, the depth $d_A$ of the critical structure 101 relative to the surface 105 of the tissue 103 can be determined by triangulating from the distance $d_w$ and known positions of the emitter 106 on the surgical device 102 and the optical waveform emitter 123 on the imaging device 120 (and, thus, the known distance $d_x$ therebetween) to determine the distance $d_y$, which is the sum of the distances $d_e$ and $d_A$.

Additionally or alternatively, time-of-flight from the optical waveform emitter 123 can be configured to determine the distance from the optical waveform emitter 123 to the surface 105 of the tissue 103. For example, a first waveform (or range of waveforms) can be utilized to determine the camera-to-critical structure distance $d_w$ and a second waveform (or range of waveforms) can be utilized to determine the distance to the surface 105 of the tissue 103. In such instances, the different waveforms can be utilized to determine the depth of the critical structure 101 below the surface 105 of the tissue 103.

Additionally or alternatively, in certain instances, the distance $d_A$ can be determined from an ultrasound, a registered magnetic resonance imaging (MRI) or computerized tomography (CT) scan. In still other instances, the distance $d_A$ can be determined with spectral imaging because the detection signal received by the imaging device can vary based on the type of material. For example, fat can decrease the detection signal in a first way, or a first amount, and collagen can decrease the detection signal in a different, second way, or a second amount.

Figure 4:
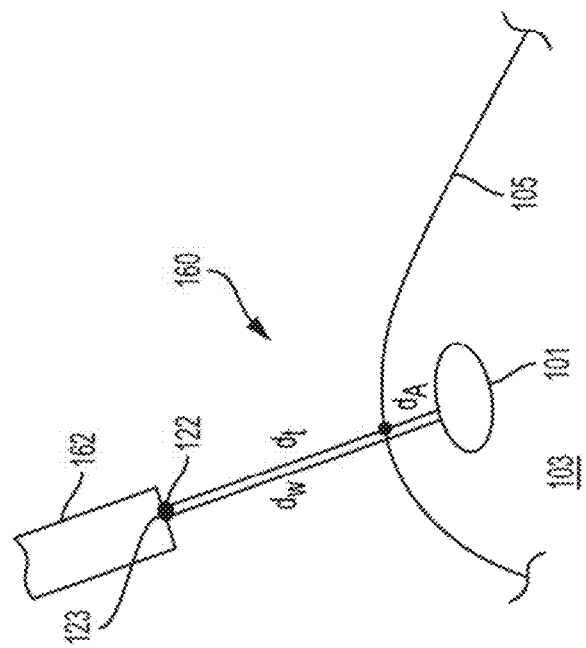
FIG. 4 is a schematic of a surgical visualization system configured to identify a critical structure below a tissue surface, wherein the surgical visualization system includes a pulsed light source for determining a depth $d_A$ of the critical structure below the tissue surface, according to at least one aspect of the present disclosure.

Referring now to a surgical visualization system 160 in FIG. 4, in which a surgical device 162 includes the optical waveform emitter 123 and the waveform sensor 122 that is configured to detect the reflected waveforms. The optical waveform emitter 123 can be configured to emit waveforms for determining the distances $d_t$ and $d_w$ from a common device, such as the surgical device 162, as further described herein. In such instances, the distance $d_A$ from the surface 105 of the tissue 103 to the surface of the critical structure 101 can be determined as follows:

$$d_A = d_w - d_t.$$

As disclosed herein, various information regarding visible tissue, embedded critical structures, and surgical devices can be determined by utilizing a combination approach that incorporates one or more time-of-flight distance sensors, spectral imaging, and/or structured light arrays in combination with an image sensor configured to detect the spectral wavelengths and the structured light arrays. Moreover, the image sensor can be configured to receive visible light and, thus, provide images of the surgical site to an imaging system. Logic or algorithms are employed to discern the information received from the time-of-flight sensors, spectral wavelengths, structured light, and visible light and render three-dimensional images of the surface tissue and underlying anatomical structures. In various instances, the imaging device 120 can include multiple image sensors.

Figure 6:
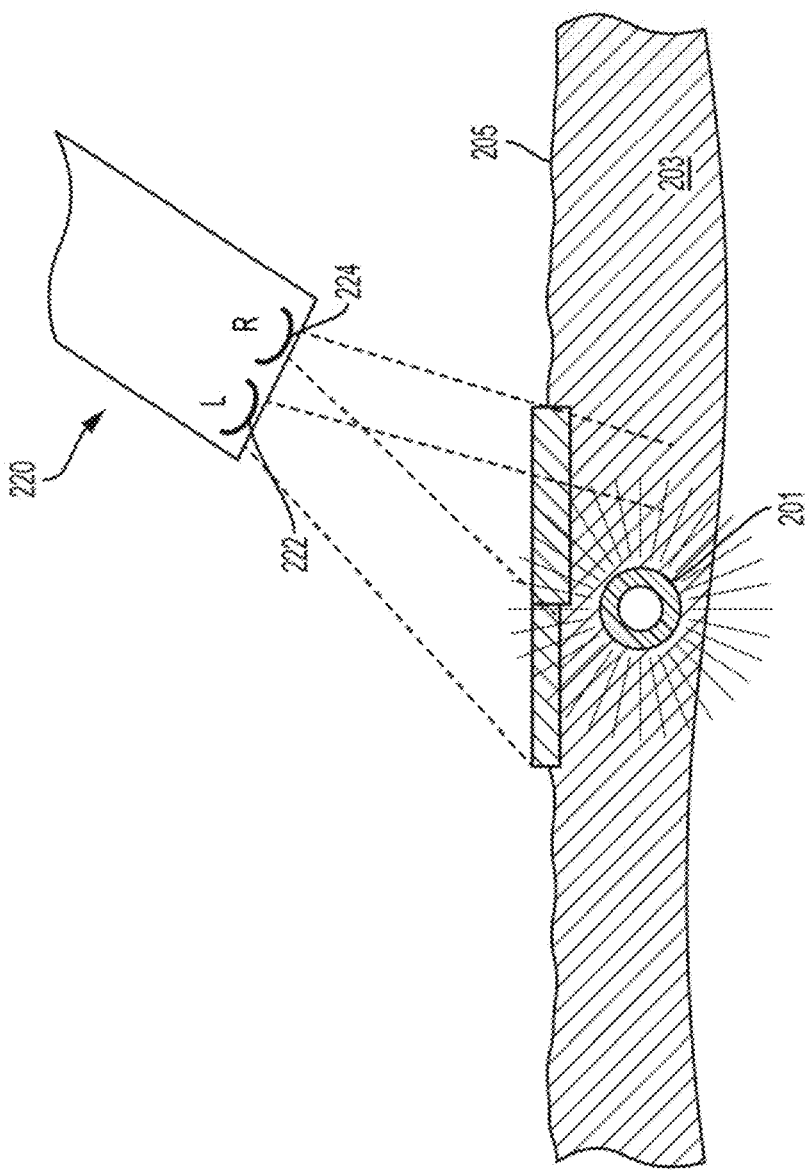
FIG. 6 is a schematic of a surgical visualization system including a three-dimensional camera, wherein the surgical visualization system is configured to identify a critical structure that is embedded within tissue, according to at least one aspect of the present disclosure.

The camera-to-critical structure distance $d_w$ can also be detected in one or more alternative ways. In one aspect, a fluoroscopy visualization technology, such as fluorescent indosciedine green (ICG), for example, can be utilized to illuminate a critical structure 201, as shown in FIGS. 6-8. A camera 220 can include two optical waveforms sensors 222, 224, which take simultaneous left-side and right-side images of the critical structure 201 (FIGS. 7A and 7B). In such instances, the camera 220 can depict a glow of the critical structure 201 below the surface 205 of the tissue 203, and the distance $d_w$ can be determined by the known distance between the sensors 222 and 224. In certain instances, distances can be determined more accurately by utilizing more than one camera or by moving a camera between multiple locations. In certain aspects, one camera can be controlled by a first robotic arm and a second camera by another robotic arm. In such a robotic system, one camera can be a follower camera on a follower arm, for example. The follower arm, and camera thereon, can be programmed to track the other camera and to maintain a particular distance and/or lens angle, for example.

Figure 9:
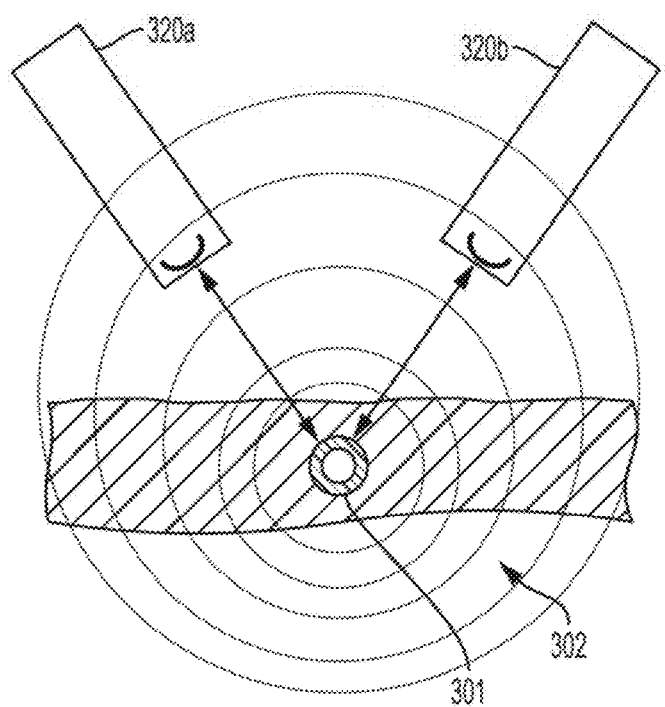
FIG. 9 is a schematic of a surgical visualization system utilizing two cameras to determine the position of an embedded critical structure, according to at least one aspect of the present disclosure.

In still other aspects, the surgical visualization system 100 may employ two separate waveform receivers (i.e. cameras/image sensors) to determine $d_w$. Referring now to FIG. 9, if a critical structure 301 or the contents thereof (e.g. a vessel or the contents of the vessel) can emit a signal 302, such as with fluoroscopy, then the actual location can be triangulated from two separate cameras 320a, 320b at known locations.

Figure 10B:
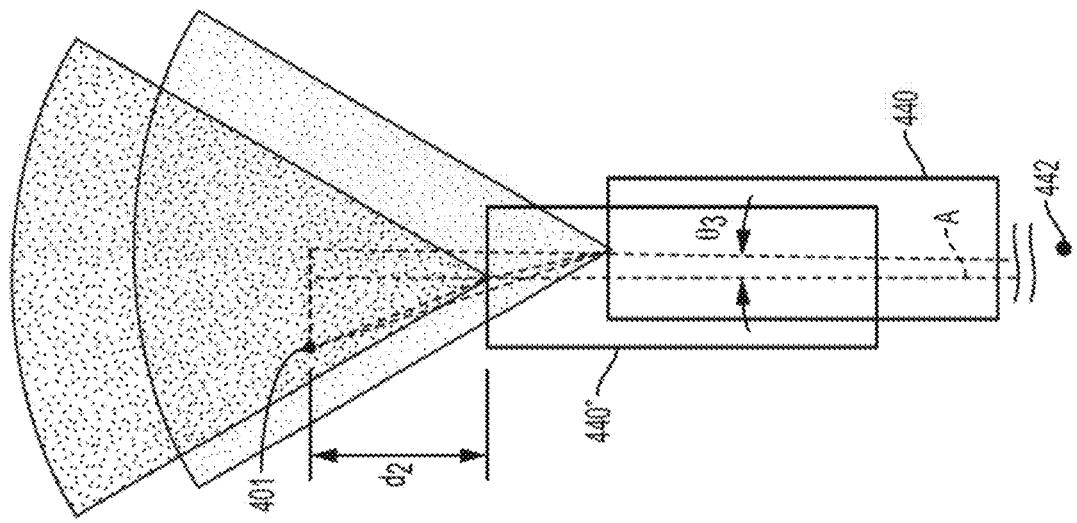
FIG. 10B is a schematic of the surgical visualization system of FIG. 10A, in which the camera is moved axially and rotationally between a plurality of known positions to determine a position of the embedded critical structure, according to at least one aspect of the present disclosure.
Figure 10A:
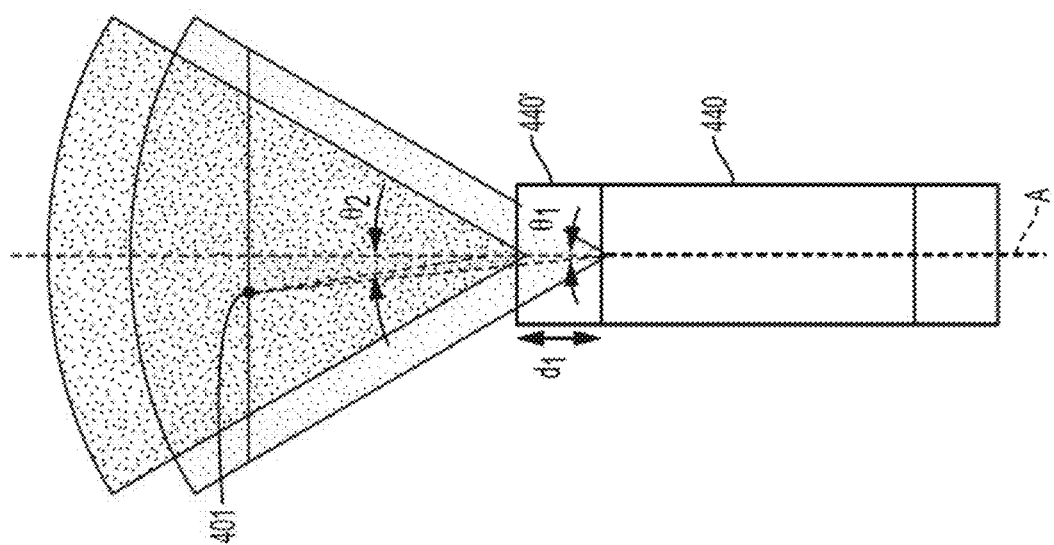
FIG. 10A is a schematic of a surgical visualization system utilizing a camera that is moved axially between a plurality of known positions to determine a position of an embedded critical structure, according to at least one aspect of the present disclosure.

In another aspect, referring now to FIGS. 10A and 10B, a surgical visualization system may employ a dithering or moving camera 440 to determine the distance $d_w$. The camera 440 is robotically-controlled such that the three-dimensional coordinates of the camera 440 at the different positions are known. In various instances, the camera 440 can pivot at a cannula or patient interface. For example, if a critical structure 401 or the contents thereof (e.g. a vessel or the contents of the vessel) can emit a signal, such as with fluoroscopy, for example, then the actual location can be triangulated from the camera 440 moved rapidly between two or more known locations. In FIG. 10A, the camera 440 is moved axially along an axis A. More specifically, the camera 440 translates a distance $d_1$ closer to the critical structure 401 along the axis A to the location indicated as a location 440', such as by moving in and out on a robotic arm. As the camera 440 moves the distance $d_1$ and the size of view change with respect to the critical structure 401, the distance to the critical structure 401 can be calculated. For example, a 4.28 mm axial translation (the distance $d_1$) can correspond to an angle $\theta_1$ of 6.28 degrees and an angle $\theta_2$ of 8.19 degrees. Additionally or alternatively, the camera 440 can rotate or sweep along an arc between different positions. Referring now to FIG. 10B, the camera 440 is moved axially along the axis A and is rotated an angle $\theta_3$ about the axis A. A pivot point 442 for rotation of the camera 440 is positioned at the cannula/patient interface. In FIG. 10B, the camera 440 is translated and rotated to a location 440″. As the camera 440 moves and the edge of view changes with respect to the critical structure 401, the distance to the critical structure 401 can be calculated. In FIG. 10B, a distance $d_2$ can be 9.01 mm, for example, and the angle $\theta_3$ can be 0.9 degrees, for example.

Figure 5:
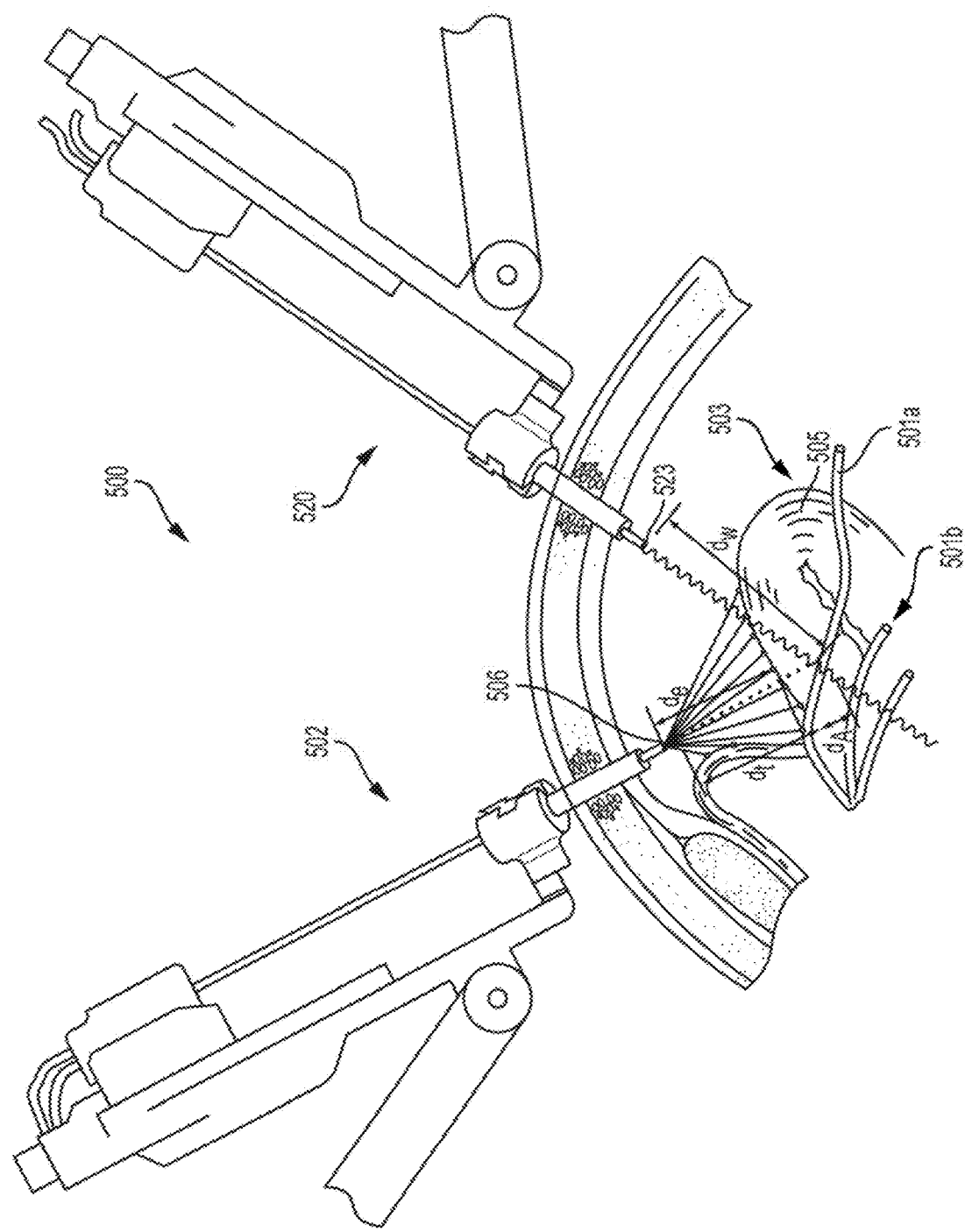
FIG. 5 is a schematic of a surgical visualization system including an imaging device and a surgical device, the surgical visualization system configured to identify a critical structure below a tissue surface, according to at least one aspect of the present disclosure.

FIG. 5 depicts a surgical visualization system 500, which is similar to the surgical visualization system 100 in many respects. In various instances, the surgical visualization system 500 can be a further exemplification of the surgical visualization system 100. Similar to the surgical visualization system 100, the surgical visualization system 500 includes a surgical device 502 and an imaging device 520. The imaging device 520 includes a spectral light emitter 523, which is configured to emit spectral light in a plurality of wavelengths to obtain a spectral image of hidden structures, for example. The imaging device 520 can also include a three-dimensional camera and associated electronic processing circuits in various instances. The surgical visualization system 500 is shown being utilized intraoperatively to identify and facilitate avoidance of certain critical structures, such as a ureter 501a and vessels 501b in an organ 503 (the uterus in this example), that are not visible on the surface.

The surgical visualization system 500 is configured to determine an emitter-to-tissue distance $d_e$ from an emitter 506 on the surgical device 502 to a surface 505 of the uterus 503 via structured light. The surgical visualization system 500 is configured to extrapolate a device-to-tissue distance $d_t$ from the surgical device 502 to the surface 505 of the uterus 503 based on the emitter-to-tissue distance $d_e$. The surgical visualization system 500 is also configured to determine a tissue-to-ureter distance $d_A$ from the ureter 501a to the surface 505 and a camera-to ureter distance $d_w$ from the imaging device 520 to the ureter 501a. As described herein with respect to FIG. 1, for example, the surgical visualization system 500 can determine the distance $d_w$ with spectral imaging and time-of-flight sensors, for example. In various instances, the surgical visualization system 500 can determine (e.g. triangulate) the tissue-to-ureter distance $d_A$ (or depth) based on other distances and/or the surface mapping logic described herein.

Figure 11:
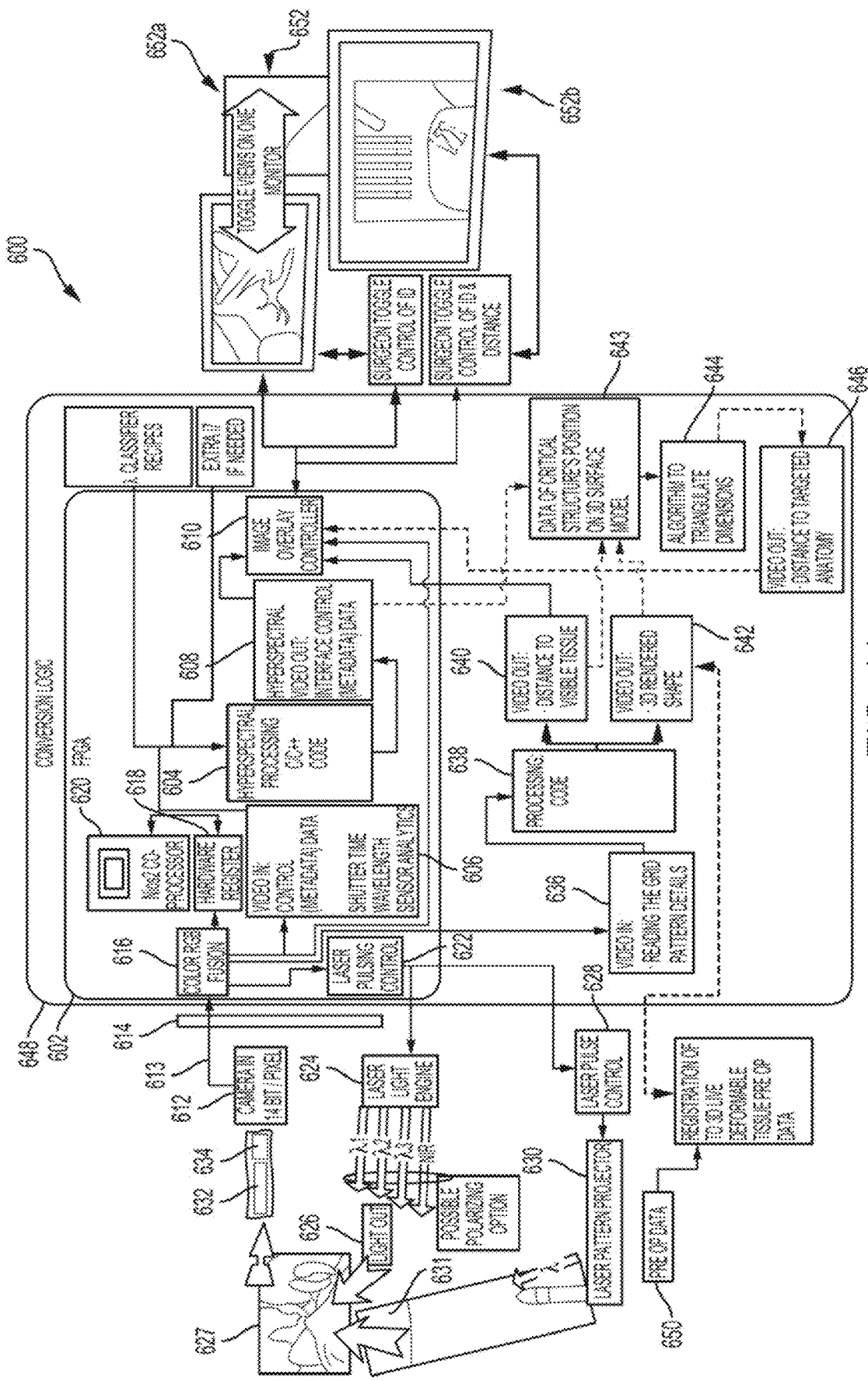
FIG. 11 is a schematic of a control system for a surgical visualization system, according to at least one aspect of the present disclosure.

Referring now to FIG. 11, where a schematic of a control system 600 for a surgical visualization system, such as the surgical visualization system 100, for example, is depicted. The control system 600 is a conversion system that integrates spectral signature tissue identification and structured light tissue positioning to identify critical structures, especially when those structures are obscured by other tissue, such as fat, connective tissue, blood, and/or other organs, for example. Such technology could also be useful for detecting tissue variability, such as differentiating tumors and/or non-healthy tissue from healthy tissue within an organ.

The control system 600 is configured for implementing a hyperspectral imaging and visualization system in which a molecular response is utilized to detect and identify anatomy in a surgical field of view. The control system 600 includes a conversion logic circuit 648 to convert tissue data to surgeon usable information. For example, the variable reflectance based on wavelengths with respect to obscuring material can be utilized to identify the critical structure in the anatomy. Moreover, the control system 600 combines the identified spectral signature and the structural light data in an image. For example, the control system 600 can be employed to create of three-dimensional data set for surgical use in a system with augmentation image overlays. Techniques can be employed both intraoperatively and preoperatively using additional visual information. In various instances, the control system 600 is configured to provide warnings to a clinician when in the proximity of one or more critical structures. Various algorithms can be employed to guide robotic automation and semi-automated approaches based on the surgical procedure and proximity to the critical structure(s).

A projected array of lights is employed to determine tissue shape and motion intraoperatively. Alternatively, flash Lidar may be utilized for surface mapping of the tissue.

The control system 600 is configured to detect the critical structure(s) and provide an image overlay of the critical structure and measure the distance to the surface of the visible tissue and the distance to the embedded/buried critical structure(s). In other instances, the control system 600 can measure the distance to the surface of the visible tissue or detect the critical structure(s) and provide an image overlay of the critical structure. p The control system 600 includes a spectral control circuit 602. The spectral control circuit 602 can be a field programmable gate array (FPGA) or another suitable circuit configuration as described herein in connection with FIGS. 2A-2C, for example. The spectral control circuit 602 includes a processor 604 to receive video input signals from a video input processor 606. The processor 604 can be configured for hyperspectral processing and can utilize C/C++ code, for example. The video input processor 606 receives video-in of control (metadata) data such as shutter time, wave length, and sensor analytics, for example. The processor 604 is configured to process the video input signal from the video input processor 606 and provide a video output signal to a video output processor 608, which includes a hyperspectral video-out of interface control (metadata) data, for example. The video output processor 608 provides the video output signal to an image overlay controller 610.

The video input processor 606 is coupled to a camera 612 at the patient side via a patient isolation circuit 614. As previously discussed, the camera 612 includes a solid state image sensor 634. The patient isolation circuit can include a plurality of transformers so that the patient is isolated from other circuits in the system. The camera 612 receives intraoperative images through optics 632 and the image sensor 634. The image sensor 634 can include a CMOS image sensor, for example, or may include any of the image sensor technologies discussed herein in connection with FIG. 2, for example. In one aspect, the camera 612 outputs images in 14 bit/pixel signals. It will be appreciated that higher or lower pixel resolutions may be employed without departing from the scope of the present disclosure. The isolated camera output signal 613 is provided to a color RGB fusion circuit 616, which employs a hardware register 618 and a Nios2 co-processor 620 to process the camera output signal 613. A color RGB fusion output signal is provided to the video input processor 606 and a laser pulsing control circuit 622.

The laser pulsing control circuit 622 controls a laser light engine 624. The laser light engine 624 outputs light in a plurality of wavelengths ($\lambda_1, \lambda_2, \lambda_3 \ldots \lambda_n$) including near infrared (NIR). The laser light engine 624 can operate in a plurality of modes. In one aspect, the laser light engine 624 can operate in two modes, for example. In a first mode, e.g.

a normal operating mode, the laser light engine 624 outputs an illuminating signal. In a second mode, e.g. an identification mode, the laser light engine 624 outputs RGBG and NIR light. In various instances, the laser light engine 624 can operate in a polarizing mode.

Light output 626 from the laser light engine 624 illuminates targeted anatomy in an intraoperative surgical site 627. The laser pulsing control circuit 622 also controls a laser pulse controller 628 for a laser pattern projector 630 that projects a laser light pattern 631, such as a grid or pattern of lines and/or dots, at a predetermined wavelength ($\lambda_2$) on the operative tissue or organ at the surgical site 627. The camera 612 receives the patterned light as well as the reflected light output through the camera optics 632. The image sensor 634 converts the received light into a digital signal.

The color RGB fusion circuit 616 also outputs signals to the image overlay controller 610 and a video input module 636 for reading the laser light pattern 631 projected onto the targeted anatomy at the surgical site 627 by the laser pattern projector 630. A processing module 638 processes the laser light pattern 631 and outputs a first video output signal 640 representative of the distance to the visible tissue at the surgical site 627. The data is provided to the image overlay controller 610. The processing module 638 also outputs a second video signal 642 representative of a three-dimensional rendered shape of the tissue or organ of the targeted anatomy at the surgical site.

The first and second video output signals 640, 642 include data representative of the position of the critical structure on a three-dimensional surface model, which is provided to an integration module 643. In combination with data from the video out processor 608 of the spectral control circuit 602, the integration module 643 can determine the distance $d_A$ (FIG. 1) to a buried critical structure (e.g. via triangularization algorithms 644), and the distance $d_A$ can be provided to the image overlay controller 610 via a video out processor 646. The foregoing conversion logic can encompass the conversion logic circuit 648 intermediate video monitors 652 and the camera 624/laser pattern projector 630 positioned at the surgical site 627.

Preoperative data 650 from a CT or MRI scan can be employed to register or align certain three-dimensional deformable tissue in various instances. Such preoperative data 650 can be provided to the integration module 643 and ultimately to the image overlay controller 610 so that such information can be overlaid with the views from the camera 612 and provided to the video monitors 652. Registration of preoperative data is further described herein and in the aforementioned contemporaneously-filed U.S. Patent Applications, including U.S. patent application Ser. No. 16/128, 195, titled INTEGRATION OF IMAGING DATA, now U.S. Patent Application Publication No. 2020/0015907, for example, which are incorporated by reference herein in their respective entireties.

The video monitors 652 can output the integrated/augmented views from the image overlay controller 610. A clinician can select and/or toggle between different views on one or more monitors. On a first monitor 652a, the clinician can toggle between (A) a view in which a three-dimensional rendering of the visible tissue is depicted and (B) an augmented view in which one or more hidden critical structures are depicted over the three-dimensional rendering of the visible tissue. On a second monitor 652b, the clinician can toggle on distance measurements to one or more hidden critical structures and/or the surface of visible tissue, for example.

The control system 600 and/or various control circuits thereof can be incorporated into various surgical visualization systems disclosed herein.

Figure 12:
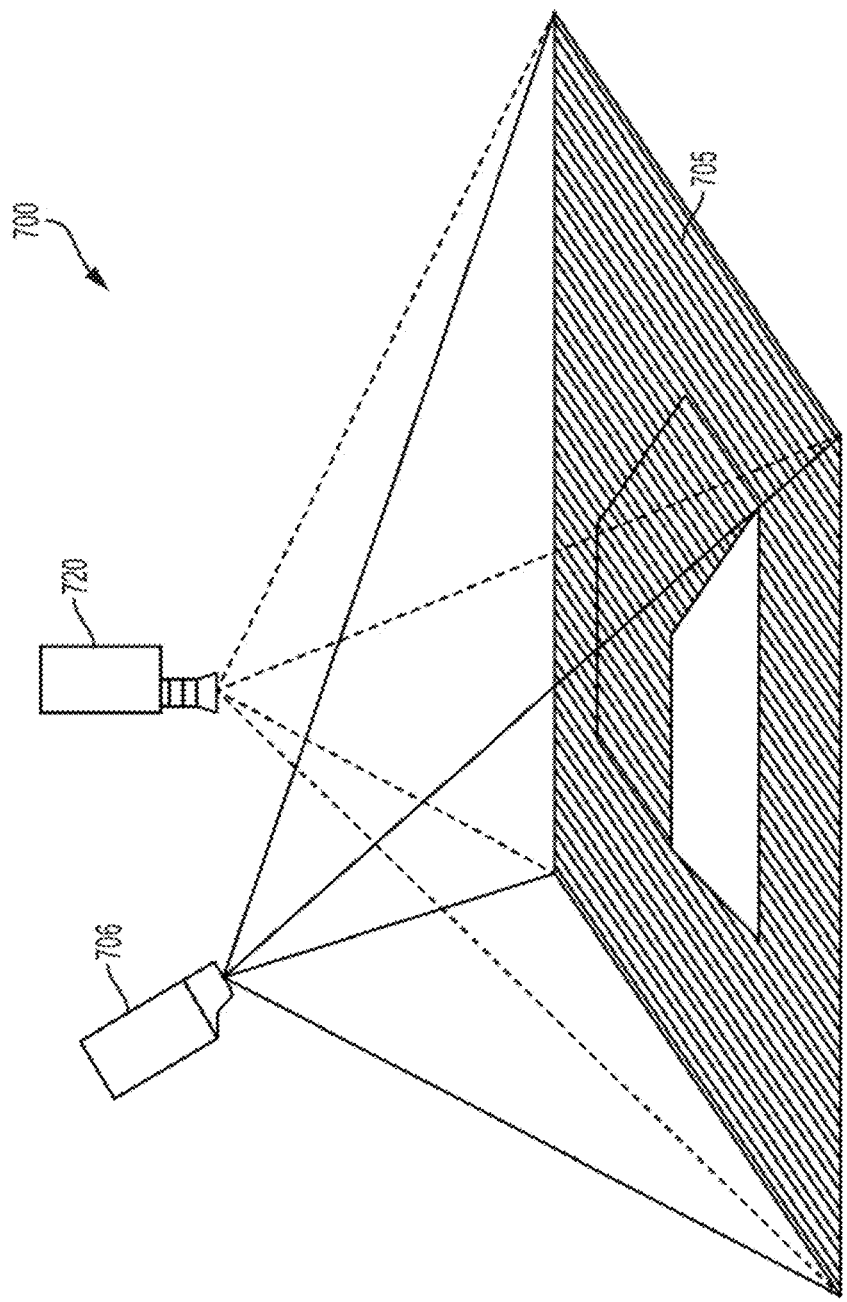
FIG. 12 is a schematic of a structured light source for a surgical visualization system, according to at least one aspect of the present disclosure.

FIG. 12 illustrates a structured (or patterned) light system 700, according to at least one aspect of the present disclosure. As described herein, structured light in the form of stripes or lines, for example, can be projected from a light source and/or projector 706 onto the surface 705 of targeted anatomy to identify the shape and contours of the surface 705. A camera 720, which can be similar in various respects to the imaging device 120 (FIG. 1), for example, can be configured to detect the projected pattern of light on the surface 705. The way that the projected pattern deforms upon striking the surface 705 allows vision systems to calculate the depth and surface information of the targeted anatomy.

In certain instances, invisible (or imperceptible) structured light can be utilized, in which the structured light is used without interfering with other computer vision tasks for which the projected pattern may be confusing. For example, infrared light or extremely fast frame rates of visible light that alternate between two exact opposite patterns can be utilized to prevent interference.

Figure 13:
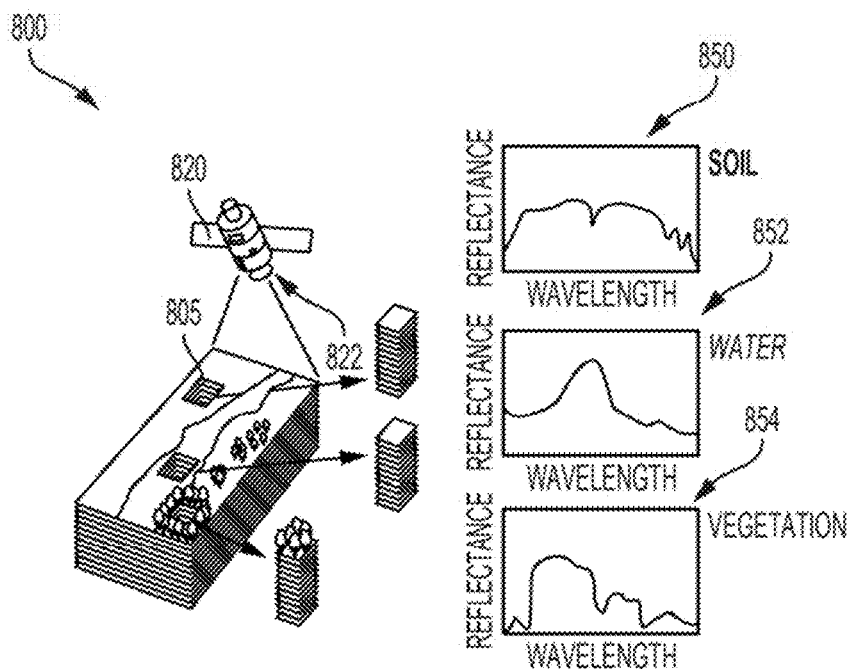
FIG. 13 is a schematic of a hyperspectral visualization system for imaging terrestrial features or objects, according to at least one aspect of the present disclosure.

Referring now to FIG. 13, by way example to illustrate the concept of hyperspectral imaging, a terrestrial hyperspectral imaging system 800 is shown. The terrestrial hyperspectral imaging system 800 is configured to image terrestrial features or objects, such as soil, water, and/or vegetation, for example. The terrestrial hyperspectral imaging system 700 includes a space-borne hyperspectral sensor 822 on a spacecraft 820 to conduct hyperspectral imaging of a portion of the Earth's surface 805. The spectral dimension includes several layers. Each pixel of the images contains a sampled spectrum that is used to identify the materials present in the pixel by their reflectance. The data can be converted to graphical representations 850, 852, 854 of reflectance as a function of wavelength for soil, water, and vegetation, respectively, for example.

Figure 14:
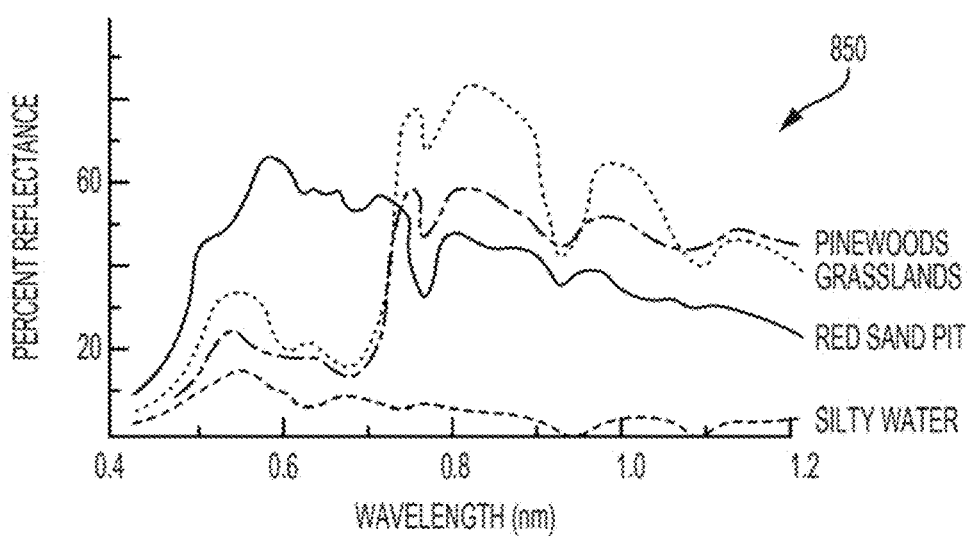
FIG. 14 is a graphical representation of hyperspectral signatures for various terrestrial features or objects, according to at least one aspect of the present disclosure.

Also by way example to illustrate the concept of hyperspectral imaging, FIG. 14 is a graphical representation 850 of hyperspectral signatures for various terrestrial features or objects, according to at least one aspect of the present disclosure. Percent reflectance is shown along the vertical axis and wavelength (nm) is shown along the horizontal axis. As shown, each object—pinewoods, grasslands, red sand pit, and silty water—has a unique hyperspectral signature that can be used to identify the object.

The hyperspectral imaging concepts described in connection with FIGS. 13 and 14 may be employed for different materials that have different wavelengths and bands of absorption, according to at least one aspect of the present disclosure. The following table illustrates the wavelengths and bands of absorption for various materials. A first range of wavelengths between 400 nm and 700 nm represents the visible light spectrum. A second range of wavelengths between 700 nm and 1400 nm represents the near infrared (NIR) spectrum. A third range of wavelengths between 1400 nm and 3000 nm represents a shortwave infrared (SWIR) spectrum. A first band centered at 1250 nm represents iron absorption and leaf moisture content. A second band between 1500 nm and 1750 nm represents plastics, fiberglass, and petroleum. A third band between 200 nm and 2400 nm represents mineral ID.

TABLE 1 specifies wavelengths and bands of absorption for various materials.

TABLE 1

| Wavelength (nm) | Region | Band(s) | Material |
|---|---|---|---|
| 400-700 | Visible | | |
| 700-1400 | NIR | | |
| 1400-3000 | SWIR | 1 - centered at 1250 | Iron adsorption |
| | | | Leaf moisture content |
| | | 2 - 1500-1750 | Plastics |
| | | | Fiberglass |
| | | | Petroleum |
| | | 3 - 200-2400 nm | Mineral ID |

Referring now to FIGS. 15A-15C, as a further illustration of hyperspectral imaging concepts, tests were conducted in which spectral imaging was applied to a fried egg 952. An image of the fried egg 952 with a yellow egg yolk 954 and an egg white 956 surrounding the egg yolk 954 is shown in FIG. 15A. A graphical representation 950 of spectral signatures for the fried egg 952 are shown in FIG. 15B. Specifically, the graphical representation 950 shows absorption units versus wavelength (nm) for the egg yolk 954 and the egg white 956 of the fried egg 952. In FIG. 15C, a spectral image (in black-and-white) of the fried egg 952 is shown, in which the image is augmented to differentiate between the egg yolk portion and the egg white portion based on the hyperspectral signature data.

In various instances, hyperspectral imaging technology, as described herein for illustrative purposes with respect to terrestrial features and objects and a fried egg, can be employed to identify signatures in anatomical structures in order to differentiate a critical structure from obscurants. Hyperspectral imaging technology may provide a visualization system that can provide a way to identify critical structures such as ureters and/or blood vessels, for example, especially when those structures are obscured by fat, connective tissue, blood, or other organs, for example. The use of the difference in reflectance of different wavelengths in the infrared (IR) spectrum may be employed to determine the presence of key structures versus obscurants. Referring now to FIGS. 16-18, illustrative hyperspectral signatures for a ureter, an artery, and nerve tissue with respect to obscurants such as fat, lung tissue, and blood, for example, are depicted.

FIG. 16 is a graphical representation 1050 of an illustrative ureter signature versus obscurants. The plots represent reflectance as a function of wavelength (nm) for wavelengths for fat, lung tissue, blood, and a ureter. FIG. 17 is a graphical representation 1052 of an illustrative artery signature versus obscurants. The plots represent reflectance as a function of wavelength (nm) for fat, lung tissue, blood, and a vessel. FIG. 18 is a graphical representation 1054 of an illustrative nerve signature versus obscurants. The plots represent reflectance as a function of wavelength (nm) for fat, lung tissue, blood, and a nerve.

In various instances, select wavelengths for spectral imaging can be identified and utilized based on the anticipated critical structures and/or obscurants at a surgical site (i.e. "selective spectral" imaging). By utilizing selective spectral imaging, the amount of time required to obtain the spectral image can be minimized such that the information can be obtained in real-time, or near real-time, and utilized intraoperatively. In various instances, the wavelengths can be selected by a clinician or by a control circuit based on input by the clinician. In certain instances, the wavelengths can be selected based on machine learning and/or big data accessible to the control circuit via a cloud, for example.

The foregoing application of spectral imaging to tissue can be utilized intraoperatively to measure the distance between a waveform emitter and a critical structure that is obscured by tissue. In one aspect of the present disclosure, referring now to FIGS. 19 and 20, a time-of-flight sensor system 1104 utilizing waveforms 1124, 1125 is shown. The time-of-flight sensor system 1104 can be incorporated into the surgical visualization system 100 (FIG. 1) in certain instances. The time-of-flight sensor system 1104 includes a waveform emitter 1106 and a waveform receiver 1108 on the same surgical device 1102. The emitted wave 1124 extends to the critical structure 1101 from the emitter 1106 and the received wave 1125 is reflected back to by the receiver 1108 from the critical structure 1101. The surgical device 1102 is positioned through a trocar 1110 that extends into a cavity 1107 in a patient.

The waveforms 1124, 1125 are configured to penetrate obscuring tissue 1103. For example, the wavelengths of the waveforms 1124, 1125 can be in the NIR or SWIR spectrum of wavelengths. In one aspect, a spectral signal (e.g. hyperspectral, multispectral, or selective spectral) or a photoacoustic signal can be emitted from the emitter 1106 and can penetrate the tissue 1103 in which the critical structure 1101 is concealed. The emitted waveform 1124 can be reflected by the critical structure 1101. The received waveform 1125 can be delayed due to the distance d between the distal end of the surgical device 1102 and the critical structure 1101. In various instances, the waveforms 1124, 1125 can be selected to target the critical structure 1101 within the tissue 1103 based on the spectral signature of the critical structure 1101, as further described herein. In various instances, the emitter 1106 is configured to provide a binary signal on and off, as shown in FIG. 20, for example, which can be measured by the receiver 1108.

Based on the delay between the emitted wave 1124 and the received wave 1125, the time-of-flight sensor system 1104 is configured to determine the distance d (FIG. 19). A time-of-flight timing diagram 1130 for the emitter 1106 and the receiver 1108 of FIG. 19 is shown in FIG. 20. The delay is a function of the distance d and the distance d is given by:

$$d = \frac{ct}{2} \cdot \frac{q_2}{q_1 + q_2}$$

where:
c=the speed of light;
t=length of pulse;
$q_1$=accumulated charge while light is emitted; and
$q_2$=accumulated charge while light is not being emitted.

As provided herein, the time-of-flight of the waveforms 1124, 1125 corresponds to the distance din FIG. 19. In various instances, additional emitters/receivers and/or pulsing signals from the emitter 1106 can be configured to emit a non-penetrating signal. The non-penetrating tissue can be configured to determine the distance from the emitter to the surface 1105 of the obscuring tissue 1103. In various instances, the depth of the critical structure 1101 can be determined by:

$$d_A = d_w - d_t$$

where:
$d_A$=the depth of the critical structure 1101;
$d_w$=the distance from the emitter 1106 to the critical structure 1101 (d in FIG. 19); and $d_t$=the distance from the emitter 1106 (on the distal end of the surgical device 1102) to the surface 1105 of the obscuring tissue 1103.

In one aspect of the present disclosure, referring now to FIG. 21, a time-of-flight sensor system 1204 utilizing waves 1224a, 1224b, 1224c, 1225a, 1225b, 1225c is shown. The time-of-flight sensor system 1204 can be incorporated into the surgical visualization system 100 (FIG. 1) in certain instances. The time-of-flight sensor system 1204 includes a waveform emitter 1206 and a waveform receiver 1208. The waveform emitter 1206 is positioned on a first surgical device 1202a, and the waveform receiver 1208 is positioned on a second surgical device 1202b. The surgical devices 1202a, 1202b are positioned through their respective trocars 1210a, 1210b, respectively, which extend into a cavity 1207 in a patient. The emitted waves 1224a, 1224b, 1224c extend toward a surgical site from the emitter 1206 and the received waves 1225a, 1225b, 1225c are reflected back to the receiver 1208 from various structures and/or surfaces at the surgical site.

The different emitted waves 1224a, 1224b, 1224c are configured to target different types of material at the surgical site. For example, the wave 1224a targets the obscuring tissue 1203, the wave 1224b targets a first critical structure 1201a (e.g. a vessel), and the wave 1224c targets a second critical structure 1201b (e.g. a cancerous tumor). The wavelengths of the waves 1224a, 1224b, 1224c can be in the visible light, NIR, or SWIR spectrum of wavelengths. For example, visible light can be reflected off a surface 1205 of the tissue 1203 and NIR and/or SWIR waveforms can be configured to penetrate the surface 1205 of the tissue 1203. In various aspects, as described herein, a spectral signal (e.g. hyperspectral, multispectral, or selective spectral) or a photoacoustic signal can be emitted from the emitter 1206. In various instances, the waves 1224b, 1224c can be selected to target the critical structures 1201a, 1201b within the tissue 1203 based on the spectral signature of the critical structure 1201a, 1201b, as further described herein. Photoacoustic imaging is further described herein and in the aforementioned contemporaneously-filed U.S. Patent Applications, which are incorporated by reference herein in their respective entireties.

The emitted waves 1224a, 1224b, 1224c can be reflected off the targeted material (i.e. the surface 1205, the first critical structure 1201a, and the second structure 1201b, respectively). The received waveforms 1225a, 1225b, 1225c can be delayed due to the distances $d_{1a}, d_{2a}, d_{3a}, d_{1b}, d_{2b}, d_{2c}$ indicated in FIG. 21.

In the time-of-flight sensor system 1204, in which the emitter 1206 and the receiver 1208 are independently positionable (e.g., on separate surgical devices 1202a, 1202b and/or controlled by separate robotic arms), the various distances $d_{1a}, d_{2a}, d_{3a}, d_{1b}, d_{2b}, d_{2c}$ can be calculated from the known position of the emitter 1206 and the receiver 1208. For example, the positions can be known when the surgical devices 1202a, 1202b are robotically-controlled. Knowledge of the positions of the emitter 1206 and the receiver 1208, as well as the time of the photon stream to target a certain tissue and the information received by the receiver 1208 of that particular response can allow a determination of the distances $d_{1a}, d_{2a}, d_{3a}, d_{1b}, d_{2b}, d_{2c}$. In one aspect, the distance to the obscured critical structures 1201a, 1201b can be triangulated using penetrating wavelengths. Because the speed of light is constant for any wavelength of visible or invisible light, the time-of-flight sensor system 1204 can determine the various distances.

Referring still to FIG. 21, in various instances, in the view provided to the clinician, the receiver 1208 can be rotated such that the center of mass of the target structure in the resulting images remains constant, i.e., in a plane perpendicular to the axis of a select target structures 1203, 1201a, or 1201b. Such an orientation can quickly communicate one or more relevant distances and/or perspectives with respect to the critical structure. For example, as shown in FIG. 21, the surgical site is displayed from a viewpoint in which the critical structure 1201a is perpendicular to the viewing plane (i.e. the vessel is oriented in/out of the page). In various instances, such an orientation can be default setting; however, the view can be rotated or otherwise adjusted by a clinician. In certain instances, the clinician can toggle between different surfaces and/or target structures that define the viewpoint of the surgical site provided by the imaging system.

In various instances, the receiver 1208 can be mounted on a trocar or cannula, such as the trocar 1210b, for example, through which the surgical device 1202b is positioned. In other instances, the receiver 1208 can be mounted on a separate robotic arm for which the three-dimensional position is known. In various instances, the receiver 1208 can be mounted on a movable arm that is separate from the robot that controls the surgical device 1202a or can be mounted to an operating room (OR) table that is intraoperatively registerable to the robot coordinate plane. In such instances, the position of the emitter 1206 and the receiver 1208 can be registerable to the same coordinate plane such that the distances can be triangulated from outputs from the time-of-flight sensor system 1204.

Combining time-of-flight sensor systems and near-infrared spectroscopy (NIRS), termed TOF-NIRS, which is capable of measuring the time-resolved profiles of NIR light with nanosecond resolution can be found in the article titled TIME-OF-FLIGHT NEAR-INFRARED SPECTROSCOPY FOR NONDESTRUCTIVE MEASUREMENT OF INTERNAL QUALITY IN GRAPEFRUIT, in the Journal of the American Society for Horticultural Science, May 2013 vol. 138 no. 3 225-228, which is incorporated by reference herein in its entirety.

In various instances, time-of-flight spectral waveforms are configured to determine the depth of the critical structure and/or the proximity of a surgical device to the critical structure. Moreover, the various surgical visualization systems disclosed herein include surface mapping logic that is configured to create three-dimensional rendering of the surface of the visible tissue. In such instances, even when the visible tissue obstructs a critical structure, the clinician can be aware of the proximity (or lack thereof) of a surgical device to the critical structure. In one instances, the topography of the surgical site is provided on a monitor by the surface mapping logic. If the critical structure is close to the surface of the tissue, spectral imaging can convey the position of the critical structure to the clinician. For example, spectral imaging may detect structures within 5 or 10 mm of the surface. In other instances, spectral imaging may detect structures 10 or 20 mm below the surface of the tissue. Based on the known limits of the spectral imaging system, the system is configured to convey that a critical structure is out-of-range if it is simply not detected by the spectral imaging system. Therefore, the clinician can continue to move the surgical device and/or manipulate the tissue. When the critical structure moves into range of the spectral imaging system, the system can identify the structure and, thus, communicate that the structure is within range. In such instances, an alert can be provided when a structure is initially identified and/or moved further within a predefined proximity zone. In such instances, even non-identification of a critical structure by a spectral imaging system with known bounds/ranges can provide proximity information (i.e. the lack of proximity) to the clinician.

Various surgical visualization systems disclosed herein can be configured to identify intraoperatively the presence of and/or proximity to critical structure(s) and to alert a clinician prior to damaging the critical structure(s) by inadvertent dissection and/or transection. In various aspects, the surgical visualization systems are configured to identify one or more of the following critical structures: ureters, bowel, rectum, nerves (including the phrenic nerve, recurrent laryngeal nerve [RLN], promontory facial nerve, vagus nerve, and branches thereof), vessels (including the pulmonary and lobar arteries and veins, inferior mesenteric artery [IMA] and branches thereof, superior rectal artery, sigmoidal arteries, and left colic artery), superior mesenteric artery (SMA) and branches thereof (including middle colic artery, right colic artery, ilecolic artery), hepatic artery and branches thereof, portal vein and branches thereof, splenic artery/vein and branches thereof, external and internal (hypogastric) ileac vessels, short gastric arteries, uterine arteries, middle sacral vessels, and lymph nodes, for example. Moreover, the surgical visualization systems are configured to indicate proximity of surgical device(s) to the critical structure(s) and/or warn the clinician when surgical device(s) are getting close to the critical structure(s).

Various aspects of the present disclosure provide intraoperative critical structure identification (e.g., identification of ureters, nerves, and/or vessels) and instrument proximity monitoring. For example, various surgical visualization systems disclosed herein can include spectral imaging and surgical instrument tracking, which enable the visualization of critical structures below the surface of the tissue, such as 1.0-1.5 cm below the surface of the tissue, for example. In other instances, the surgical visualization system can identify structures less than 1.0 cm or more the 1.5 cm below the surface of the tissue. For example, even a surgical visualization system that can identify structures only within 0.2 mm of the surface, for example, can be valuable if the structure cannot otherwise be seen due to the depth. In various aspects, the surgical visualization system can augment the clinician's view with a virtual depiction of the critical structure as a visible white-light image overlay on the surface of visible tissue, for example. The surgical visualization system can provide real-time, three-dimensional spatial tracking of the distal tip of surgical instruments and can provide a proximity alert when the distal tip of a surgical instrument moves within a certain range of the critical structure, such as within 1.0 cm of the critical structure, for example.

Various surgical visualization systems disclosed herein can identify when dissection is too close to a critical structure. Dissection may be "too close" to a critical structure based on the temperature (i.e. too hot within a proximity of the critical structure that may risk damaging/heating/melting the critical structure) and/or based on tension (i.e. too much tension within a proximity of the critical structure that may risk damaging/tearing/pulling the critical structure). Such a surgical visualization system can facilitate dissection around vessels when skeletonizing the vessels prior to ligation, for example. In various instances, a thermal imaging camera can be utilized to read the heat at the surgical site and provide a warning to the clinician that is based on the detected heat and the distance from a tool to the structure. For example, if the temperature of the tool is over a predefined threshold (such as 120 degrees F., for example), an alert can be provided to the clinician at a first distance (such as 10 mm, for example), and if the temperature of the tool is less than or equal to the predefined threshold, the alert can be provided to the clinician at a second distance (such as 5 mm, for example). The predefined thresholds and/or warning distances can be default settings and/or programmable by the clinician. Additionally or alternatively, a proximity alert can be linked to thermal measurements made by the tool itself, such as a thermocouple that measures the heat in a distal jaw of a monopolar or bipolar dissector or vessel sealer, for example.

Various surgical visualization systems disclosed herein can provide adequate sensitivity with respect to a critical structure and specificity to enable a clinician to proceed with confidence in a quick but safe dissection based on the standard of care and/or device safety data. The system can function intraoperatively and in real-time during a surgical procedure with minimal ionizing radiation risk to a patient or a clinician and, in various instances, no risk of ionizing radiation risk to the patient or the clinician. Conversely, in a fluoroscopy procedure, the patient and clinician(s) may be exposed to ionizing radiation via an X-ray beam, for example, that is utilized to view the anatomical structures in real-time.

Various surgical visualization system disclosed herein can be configured to detect and identify one or more desired types of critical structures in a forward path of a surgical device, such as when the path of the surgical device is robotically controlled, for example. Additionally or alternatively, the surgical visualization system can be configured to detect and identify one or more types of critical structures in a surrounding area of the surgical device and/or in multiple planes/dimensions, for example.

Various surgical visualization systems disclosed herein can be easy to operate and/or interpret. Moreover, various surgical visualization systems can incorporate an "override" feature that allows the clinician to override a default setting and/or operation. For example, a clinician can selectively turn off alerts from the surgical visualization system and/or get closer to a critical structure than suggested by the surgical visualization system such as when the risk to the critical structure is less than risk of avoiding the area (e.g. when removing cancer around a critical structure the risk of leaving the cancerous tissue can be greater than the risk of damage to the critical structure).

Various surgical visualization systems disclosed herein can be incorporated into a surgical system and/or used during a surgical procedure with limited impact to the workflow. In other words, implementation of the surgical visualization system may not change the way the surgical procedure is implemented. Moreover, the surgical visualization system can be economical in comparison to the costs of an inadvertent transection. Data indicates the reduction in inadvertent damage to a critical structure can drive incremental reimbursement.

Various surgical visualization systems disclosed herein can operate in real-time, or near real-time, and far enough in advance to enable a clinician to anticipate critical structure (s). For example, a surgical visualization system can provide enough time to "slow down, evaluate, and avoid" in order to maximize efficiency of the surgical procedure.

Various surgical visualization systems disclosed herein may not require a contrast agent, or dye, that is injected into tissue. For example, spectral imaging is configured to visualize hidden structures intraoperatively without the use of a contrast agent or dye. In other instances, the contrast agent can be easier to inject into the proper layer(s) of tissue than other visualization systems. The time between injection of the contrast agent and visualization of the critical structure can be less than two hours, for example.

Various surgical visualization systems disclosed herein can be linked with clinical data and/or device data. For example, data can provide boundaries for how close energy-enabled surgical devices (or other potentially damaging devices) should be from tissue that the surgeon does not want to damage. Any data modules that interface with the surgical visualization systems disclosed herein can be provided integrally or separately from a robot to enable use with stand-alone surgical devices in open or laparoscopic procedures, for example. The surgical visualization systems can be compatible with robotic surgical systems in various instances. For example, the visualization images/information can be displayed in a robotic console.

FIG. 22 illustrates a force sensor system 5000 through structured light deflection detection, according to at least one aspect of the present disclosure. The force sensor system 5000 provides a method of determining shaft 5003 flex and provides a user awareness of haptics. For example, conveying to the surgeon properties of feel related to the tissue such as how heavy the tissue is when manipulating, how constrained it is, how hard, how stiff, or combinations thereof. A first straight line laser source 5002a (e.g., a straight line laser transmitter) is mounted on top of and at a proximal end 5024 of a shaft 5003 of a surgical device/tool 5004. In various aspects, a line laser is a laser modified to project a line rather than a point (e.g., laser pointer). This may be achieved by passing the beam through a cylindrical lens or a Powell lens. Using multiple lasers, it is possible to project multiple lines for use with image processing. Depending on the application, line lasers can generate lines, crosses or other patterns. The first straight line laser source 5002a projects a first laser line 5056a and establishes a first reference just above the top of a straight, un-flexed or unloaded, shaft 5003. In one aspect, a second straight line laser source 5002b is mounted on the bottom of and at a proximal end 5024 of the shaft 5003 of the surgical device/tool 5004. The second straight line laser source 5002b projects a second laser line 5006b that exits as a second straight line and establishes a second reference just below the bottom of a straight, un-flexed or unloaded, shaft 5003. It will be appreciated that multiple laser light transmitters/sources may be employed to measure deflection of the shaft 5003 as the surgical device/tool 5004 is rotated, for example.

In the unloaded position, the shaft 5003' is disposed in a straight line or "un-flexed" configuration and is shown in dashed line form. In the unloaded shaft 5003' configuration, the first laser line 5006a is projected along a straight line just above unloaded shaft 5003'. When the end effector 5018 portion of the surgical device/tool 5004 grasps tissue such as a section of the colon 5019, the shaft 5003 flexes. The deflection 5020 distance "d" is measured from the first laser line 5006a at the distal end 5026 of the shaft 5003 of the surgical device/tool 5004. The first laser line 5006a always remains straight relative to the shaft 5003. A camera 5010 located at the distal end 5026 of the shaft 5003 is positioned to capture images of the distal end 5026 of the shaft 5003 to detect the distance of the edge of the shaft 5003 from the first laser line 5006a, and thus to detect the change in distance "d" of the edge of the shaft 5003 from the first laser line 5006a as the shaft 5003 is deflected. The camera 5010 is configured to emit and receive structured light. The first laser line 5006a projected down the shaft 5003 is invisible to naked eye, but can be detected by the camera 5010. In one aspect, the camera 5010 is a NIR camera including a time-of-flight sensor system that includes an emitter 5012 to project NIR light in a pattern and a receiver 5104 that detects NIR light that bounces off the shaft 5003. In another aspect, the camera 5010 employs structured light 5016 to detect the deflection of the shaft 5003.

The camera 5010 is placed at a distal end 5026 of the shaft 5003 of the surgical device/tool 5004. The deflection 5020, measured as the distance "d", of the distal end 5026 of the shaft 5003 is a function force F and may be expressed as follows:

$$d=f(F)$$

The force sensor system 5000 is analogous to a deflecting beam-type torque wrench 5500 shown in FIG. 25 where a pointer beam 5052 is attached to a wrench head 5054. As the torque wrench 5500 itself is "twisted" (e.g., torqued, a twisting force), the pointer beam 5052 stays in place, and the scale 5056 beneath the pointer 5058 moves to indicate the amount of twist, or torque, being applied. It is important that the handle 5059, which "floats" is never locked against the sides of the torque wrench 5500. It should always be floating when held, for an accurate torque reading. With reference now back to FIG. 22, in the force sensor system 5000 the beam is represented by the straight laser light 5006a and the amount of deflection 5020, distance "d" indicates the amount of twist, or torque, being applied to the shaft 5003. The force F may be displayed on a video monitoring system 5030 described in connection with FIG. 23.

FIG. 23 is a video monitoring system 5030 configured to display a surgical scene and the measured force F applied to the shaft 5003 of the surgical device/tool 5004, according to at least one aspect of the present disclosure. The video monitoring system 5030 includes a screen 5032 with a main display portion 5034 to display the surgical scene including a visualization of the hidden critical structures of the anatomy 5019 as well as the shaft 5003 and end effector 5018 portions of the surgical device/tool 5004. The screen 5032 includes an additional display portion 5044 to display a menu 5036 and the force F applied on the shaft 5003 of the surgical device/tool 5004. The additional display portion 5044 displays the force (lbs.) 5038 units and a bar graph 5040 with a pointer 5042 to indicate the applied force F.

With reference now to FIGS. 22 and 23, in one aspect, the laser line 5006a is projected just above the surgical device/tool 5004. The shaft 5003 of the surgical device/tool 5004 bends or deflects under load with respect to the laser line 5006a, which remains straight. The camera 5010 determines the change in distance "d" of the edge of the shaft 5003 from the straight laser line 5006a (non-visible) down the shaft 5003. The image and the deflection may be pulsed by the camera 5010 in alternative frames that are displayed on the screen 5032 of the video monitor system 5030 for the surgeon to see. The image on the surgeon's video monitor system 5030 does not show the straight laser line 5006a. The straight laser line 5006a is detected by the camera 5010 and a measurement is made of the distance "d" to the edge of the shaft 5003. Shaft 5003 flex is determined and correlated to a known force F needed to bend the shaft 5003 by a predetermined distance "d". The force sensor system 5000 eliminates the need for a traditional force sensor. It will be appreciated that structured light can be nonvisible to the surgeon in several 2 ways. For example, in one technique, the structured light can be in the nonvisible light spectrum. In another technique, the structured light can be in the visible light spectrum that is pulsed in certain frames and those frames are excluded in the video stream provided to the surgeon. This is analogous to augmented reality with the structured light augmented out of view.

FIG. 24 illustrates a straight line laser source 5002a, 5002b, according to at least one aspect of the present disclosure. The straight line laser source 5002a, 5002b includes a laser aperture 5046a, 5046b where the straight laser line 5006a, 5006b is emitted from a cylindrical lens or a Powell lens, for example.

In various aspects, the force sensor system 5000, or the video monitoring system 5030, may be in communication with or formed integrally with the control system 133 or the control system 600 for a surgical visualization system as described in connection with FIGS. 2, 2A-2C, and 11, either of which can be utilized with the surgical visualization system 100. Accordingly, the first and second straight line laser transmitters/sources 5002a, 5002b, the camera 5010, or the video monitoring system 5030, or a combination thereof, may be controlled by the control circuit 132 or the conversion logic circuit 648. In other aspects, the force sensor system 5000 may be controlled by any one of the control circuit 400, combinational logic circuit 410, or sequential logic circuit 420, or any combination thereof. Accordingly, in various aspects, the first and second straight line laser transmitters/sources 5002a, 5002b, the camera 5010, or the video monitoring system 5030, or combinations thereof, may be controlled by the control circuit 132, or the conversion logic circuit 648, or combinations thereof.

FIG. 26 illustrates a logic flow diagram 5060 of a process depicting a control program or a logic configuration to determine a force applied to a surgical instrument or tool using force sensor through structured light deflection detection, in accordance with at least one aspect of the present disclosure. A process in accordance with the logic flow diagram 5060 may be executed by the control system 133 shown in FIG. 2 and can be utilized with the surgical visualization system 100. The control system 133 includes a control circuit 132 in signal communication with a memory 134 to implement the force sensor system 5000 through structured light deflection detection as described in connection with FIGS. 22-25, for example. Wth reference now to FIGS. 2 and 22-26, the memory 134 of the control circuit 132 stores instructions executable by the control circuit 132 to determine the force F applied to the shaft 5003 of the surgical device/tool 5004. According to the logic flow diagram 5060, the control circuit 132 controls one or both straight line laser transmitters/sources 5002a, 50002b to project 5062 a straight laser line 5006a, 5006b reference. As discussed above, the straight laser line 5006a, 5006b reference is detected by a camera 5010, which may be incorporated into the camera 144 of the imaging system 142 comprising an image sensor 135. The control circuit 132 uses the image information generated by the camera 5010 to determine 5064 a distance or change in distance "d" of the edge of the shaft 5003 from the projected the straight laser line 5006a, 5006b reference (non-visible) down the shaft 5003. Once the distance "d" is determined, the control circuit 132 determines 5066 the force "F" applied to the shaft based on the distance "d". The control circuit 132 is in communication with the video monitoring system 5030 configured to provide image data to the display 5068 a surgical scene and the measured force "F" applied to the shaft 5003 of the surgical device/tool 5004. The control circuit 132 is configured to pulse the image data in alternative frames that are displayed on the main display portion 5034 of the screen 5032 of the video monitoring system 5030. The control circuit 132 provides the force "F" to a robotic control system to control the state of the surgical device/tool 5004.

FIGS. 27A-27C illustrate a jaw centering and homing indication system 5070 through structured light, according to at least one aspect of the present disclosure. The system 5070 provides a method for determining jaw 5074 position and confirmation of robotic correctness.

FIG. 27A illustrates a surgical device/tool 5072 with a centered jaw 5074 in the open position, according to at least one aspect of the present disclosure. The jaw 5074 includes first and second jaws 5074a, 5074b that are movable relative to each other. A straight line laser source 5075 is positioned in the center and proximal end of a shaft 5076 of the surgical device/tool 5072. The straight line laser source 5075 is configured to project a straight laser line 5077 reference that is projected through the center of the shaft 5076. A camera 5078 is positioned beyond the distal end of the shaft 5076 to capture images of the first and second jaws 5074a, 5074b to monitor the position of the first and second jaws 5074a, 5074b relative to the straight laser line 5077 reference generated by the straight line laser source 5075. The camera 5078 is configured to emit and receive structured light. The camera 5978 includes an emitter 5080 to generate NIR light and a receiver 5082 that detects NIR light that bounces off the distal ends of the first and second jaws 5074a, 5074b. The camera 5078 visualization system is able to measure the distances $d_1$ and $d_2$ from the straight laser line 5077 reference to the tips of the first and second jaws 5074a, 5074b. When the first and second jaws 5074a, 5074b are in the centered configuration, as shown in FIG. 27A, the distances $d_1$ and $d_2$ are equal ($d_1=d_2$).

FIG. 27B illustrates the surgical device/tool 5072 shown in FIG. 27A with an off-center jaw 5074 in the closed position, according to at least one aspect of the present disclosure. In the off-center configuration with the first and second jaws 5074a, 5074b in the closed position, the distance $d_1$ is less than the distance $d_2$ ($d_1<d_2$).

FIG. 27C illustrates the surgical device/tool 5072 shown in FIG. 27A with a centered jaw 5074 in the closed position, according to at least one aspect of the present disclosure. In the centered configuration with the first and second jaws 5074a, 5074b in the closed position, the distances $d_1$ and $d_2$ are equal ($d_1=d_2$).

Wth reference to FIGS. 27A-27C, in one aspect the straight laser line 5077 is projected on top of the surgical device/tool 5072 just above the shaft 5076. Measurements of the position of the first and second jaws 5074a, 5074b are made with respect to the straight laser line 5077 reference. The camera 5078 can be pulsed in alternative frames that are shown to a surgeon on a video display screen such as, for example, the screen 5032 of the video monitoring system 5030 shown in FIG. 23. The image shown on the surgeon monitor does not have a visible laser light. The straight laser line 5077 is detected by the camera 5078 system and a measurement is made to the edge of the shaft 5076. The jaw centering and homing indication system 5070 may be used to compare or confirm the position of the first and second jaws 5074a, 5074b relative to the position of the first and second jaws 5074a, 5074b determined by a robotic system.

In various aspects, the jaw centering and homing indication system 5070 through structured light, or the video monitoring system 5030 (FIG. 23), may be in communication with or formed integrally with the control system 133 or the control system 600 for a surgical visualization system as described in connection with FIGS. 2, 2A-2C, and 11, either of which can be utilized with the surgical visualization system 100. Accordingly, the straight line laser source 5075, the camera 5078, or the video monitoring system 5030, or a combination thereof, may be controlled by the control circuit 132 or the conversion logic circuit 648. In other aspects, the jaw centering and homing indication system 5070 may be controlled by any one of the control circuit 400, combinational logic circuit 410, or sequential logic circuit 420, or any combination thereof. Accordingly, in various aspects, the straight line laser source 5075, the camera 5078, or the video monitoring system 5030, or combinations thereof, may be controlled by the control circuit 132, or the conversion logic circuit 648, or combinations thereof.

FIG. 28 illustrates a logic flow diagram 5090 of a process depicting a control program or a logic configuration to determine a jaw 5074 centering and homing indication of the surgical instrument or tool 5072 through structured light, in accordance with at least one aspect of the present disclosure. A process in accordance with the logic flow diagram 5090 may be executed by the control system 133 shown in FIG. 2 and can be utilized with the surgical visualization system 100. The control system 133 includes a control circuit 132 in signal communication with a memory 134 to implement the jaw 5074 centering and homing indication of the surgical instrument or tool 5072 through structured light as described in connection with FIGS. 27A-27C, for example. Wth reference now to FIGS. 2 and 27A-27C, the memory 134 of the control circuit 132 stores instructions executable by the control circuit 132 to determine the position of the first and second jaws 5074a, 5074b of the surgical instrument or tool 5072 relative to a laser straight line 5077. The control circuit 132 controls the straight line laser source 5075 to transmit 5092 the straight laser line 5077 reference. The camera 5078 use structured light to generate images of the position of the position of the first and second jaws 5074a, 5074b. The projected straight laser line 5077 reference is detected by the camera 5078, which may be incorporated into the camera 144 of the imaging system 142 comprising an image sensor 135. The control circuit 132 uses the image information generated by the camera 5078 to determine 5094 the distances "$d_1$" and "$d_2$" measured from the distal ends of the first and second jaws 5074a, 5074b to the projected straight laser line 5077 reference. Once the distances "$d_1$" and "$d_2$" are determined, the control circuit 132 determines 5096 the state of the first and second jaws 5074a, 5074b. The state of the first and second jaws 5074a, 5074b may include, for example, centered, off-centered, or closed, or combinations thereof. The control circuit 132 provides 5098 commands or signals to a robotic control system to center or home the first and second jaws 5074a, 5074b based on the state of the first and second jaws 5074a, 5074b. The control circuit 132 is in communication with the video monitoring system 5030 configured to display 5099 image data provided by the control circuit 132 of a surgical scene and the measured position of the first and second jaws 5074a, 5074b of the surgical device/tool 5072. The control circuit 132 is configured to pulse the image data in alternative frames that are displayed on the main display portion 5034 of the screen 5032 of the video monitoring system 5030.

In various aspects, the systems described in connection with FIGS. 22-28 may be generalized to detect a movable element of a surgical tool by employing a straight laser line reference and a camera to detect the movable element. Accordingly, turning now to FIG. 29, there is shown a logic flow diagram 5100 of a process depicting a control program or a logic configuration to determine a position of a movable element of a surgical instrument or tool through structured light, in accordance with at least one aspect of the present disclosure. A process in accordance with the logic flow diagram 5100 may be executed by the control system 133 shown in FIG. 2 and can be utilized with the surgical visualization system 100. The control system 133 includes a control circuit 132 in signal communication with a memory 134 to detect the position of a movable element of a surgical instrument or tool through structured light. Wth reference now to FIGS. 2 and 27A-27C, the memory 134 of the control circuit 132 stores instructions executable by the control circuit 132 to determine the position of a movable element of a surgical instrument or tool relative to a laser straight line. The control circuit 132 controls a straight line laser source to project 5102 a straight laser line reference. A camera positioned in a manner to capture images of the movable element to enable the processor to detect the positon of the movable element relative to the projected straight laser line reference is detected by the camera, which may be incorporated into the camera 144 of the imaging system 142 comprising an image sensor 135. The control circuit 132 uses the image information generated by the camera to determine 5104 the position of the movable element relative to the projected straight laser line reference. Once the position of the movable element is determined, the control circuit 132 determines 5106 the state of the movable element. The state of the movable element may include, for example, centered, off-centered, closed, open, flexed, unflexed, twisted, untwisted, bent, unbent, or combinations thereof. The control circuit 132 provides 5108 commands or signals to a robotic control system to position or reposition the movable element. The control circuit 132 is in communication with the video monitoring system 5030 and is configured to display 5109 image data provided by the control circuit 132 of a surgical scene and the measured position of the movable element of the surgical device/tool. The control circuit 132 is configured to pulse the image data in alternative frames that are displayed on the main display portion 5034 of the screen 5032 of the video monitoring system 5030.

Example Clinical Applications

Various surgical visualization systems disclosed herein may be employed in one or more of the following clinical applications. The following clinical applications are non-exhaustive and merely illustrative applications for one or more of the various surgical visualization systems disclosed herein.

A surgical visualization system, as disclosed herein, can be employed in a number of different types of procedures for different medical specialties, such as urology, gynecology, oncology, colorectal, thoracic, bariatric/gastric, and hepato-pancreato-biliary (HPB), for example. In urological procedures, such as a prostatectomy, for example, the ureter may be detected in fat or connective tissue and/or nerves may be detected in fat, for example. In gynecological oncology procedures, such as a hysterectomy, for example, and in colorectal procedures, such as a low anterior resection (LAR) procedure, for example, the ureter may be detected in fat and/or in connective tissue, for example. In thoracic procedures, such as a lobectomy, for example, a vessel may be detected in the lung or in connective tissue and/or a nerve may be detected in connective tissue (e.g., an esophagostomy). In bariatric procedures, a vessel may be detected in fat. In HPB procedures, such as a hepatectomy or pancreatectomy, for example, a vessel may be detected in fat (extrahepatic), in connective tissue (extrahepatic), and the bile duct may be detected in parenchyma (liver or pancreas) tissue.

In one example, a clinician may want to remove an endometrial myoma. From a preoperative magnetic resonance imaging (MRI) scan, the clinician may know that the endometrial myoma is located on the surface of the bowel. Therefore, the clinician may want to know, intraoperatively, what tissue constitute a portion of the bowel and what tissue constitutes a portion of the rectum. In such instances, a surgical visualization system, as disclosed herein, can indicate the different types of tissue (bowel versus rectum) and convey that information to a clinician via an imaging system. Moreover, the imaging system can determine and communicate the proximity of a surgical device to the select tissue. In such instances, the surgical visualization system can provide increased procedural efficiency without critical complications.

In another example, a clinician (e.g. a gynecologist) may stay away from certain anatomic regions to avoid getting too close to critical structures and, thus, the clinician may not remove all of the endometriosis, for example. A surgical visualization system, as disclosed herein, can enable the gynecologist to mitigate the risk of getting too close to the critical structure such that the gynecologist can get close enough with the surgical device to remove all the endometriosis, which can improve the patient outcomes (democratizing surgery). Such a system can enable the surgeon to "keep moving" during the surgical procedure instead of repeatedly stopping and restarting in order to identify areas to avoid, especially during the application of therapeutic energy such as ultrasonic or electrosurgical energy, for example. In gynecological applications, uterine arteries and ureters are important critical structures and the system may be particularly useful for hysterectomy and endometriosis procedures given the presentation and/or thickness of tissue involved.

In another example, a clinician may risk dissection of a vessel at a location that is too proximal and, thus, which can affect blood supply to a lobe other than the target lobe. Moreover, anatomic differences from patient to patient may lead to dissection of a vessel (e.g. a branch) that affects a different lobe based on the particular patient. A surgical visualization system, as disclosed herein, can enable the identification of the correct vessel at the desired location, which enables the clinician to dissect with appropriate anatomic certainty. For example, the system can confirm that the correct vessel is in the correct place and then the clinician can safely divide the vessel.

In another example, a clinician may make multiple dissections before dissecting at the best location due to uncertainty about the anatomy of the vessel. However, it is desirable to dissect in the best location in the first instance because more dissection can increase the risk of bleeding. A surgical visualization system, as disclosed herein, can minimize the number of dissections by indicating the correct vessel and the best location for dissection. Ureters and cardinal ligaments, for example, are dense and provide unique challenges during dissection. In such instances, it can be especially desirable to minimize the number of dissections.

In another example, a clinician (e.g. a surgical oncologist) removing cancerous tissue may want to know the identification of critical structures, localization of the cancer, staging of the cancer, and/or an evaluation of tissue health. Such information is beyond what a clinician sees with the "naked eye". A surgical visualization system, as disclosed herein, can determine and/or convey such information to the clinician intraoperatively to enhance intraoperative decision making and improve surgical outcomes. In certain instances, the surgical visualization system can be compatible with minimally invasive surgery (MIS), open surgery, and/or robotic approaches using either an endoscope or exoscope, for example.

In another example, a clinician (e.g. a surgical oncologist) may want to turn off one or more alerts regarding the proximity of a surgical tool to one or more critical structure to avoid being overly conservative during a surgical procedure. In other instances, the clinician may want to receive certain types of alerts, such as haptic feedback (e.g. vibrations/buzzing) to indicate proximity and/or or "no fly zones" to stay sufficiently far away from one or more critical structures. A surgical visualization system, as disclosed herein, can provide flexibility based on the experience of the clinician and/or desired aggressiveness of the procedure, for example. In such instances, the system provides a balance between "knowing too much" and "knowing enough" to anticipate and avoid critical structures. The surgical visualization system can assist in planning the next step(s) during a surgical procedure.

EXAMPLES

Various aspects of the subject matter described herein are set out in the following numbered examples.

Example 1. A surgical visualization system, comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of an element of a surgical device; control the image sensor to detect the projected straight laser line and structured light reflected from the surface of the element of the surgical device; and determine a position of the element of the surgical device relative to the projected straight laser line reference.

Example 2. The surgical visualization system of Example 1, wherein the element of the surgical device is a movable element and the memory stores instructions executable by the control circuit to determine the state of the movable element.

Example 3. The surgical visualization system of Examples 1 or 2, wherein the memory stores instructions executable by the control circuit to provide commands or signals to a robotic control system.

Example 4. The surgical visualization system of Example 3, wherein the commands or signals to the robotic control system are configured by the control circuit to adjust a position of the element of the surgical device based on the detected projected straight laser line and the structured light reflected form the surface of the element of the surgical device.

Example 5. The surgical visualization system of any one of Examples 1-4, wherein the memory stores instructions executable by the control circuit to provide image data associated with a surgical scene and the measured position of the element to a display of a video monitoring system.

Example 6. The surgical visualization system of Example 5, wherein the memory stores instructions executable by the control circuit to pulse the image data in alternative frames displayed on the display of the video monitoring system.

Example 7. A surgical visualization system, comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of distal end of a shaft of a surgical device; control the image sensor to detect the projected straight laser line and structured light reflected from the surface of the distal end of the shaft of the surgical device; and determine a distance "d" from the projected straight laser line reference to the distal end of the shaft of the surgical device.

Example 8. The surgical visualization system of Example 7, wherein the memory stores instructions executable by the control circuit to determine a force "F" applied to the shaft based on the distance "d."

Example 9. The surgical visualization system of Example 7 or 8, wherein the memory stores instructions executable by the control circuit to provide commands or signals to a robotic control system.

Example 10. The surgical visualization system of Example 9, wherein the commands or signals to the robotic control system are configured by the control circuit to control a state of the surgical device.

Example 11. The surgical visualization system of any one of Examples 7-10, wherein the memory stores instructions executable by the control circuit to provide image data associated with a surgical scene and the distance "d" from the projected straight laser line reference to the distal end of the shaft of the surgical device to a display of a video monitoring system.

Example 12. The surgical visualization system of Example 11, wherein the memory stores instructions executable by the control circuit to pulse the image data in alternative frames displayed on the display of the video monitoring system.

Example 13. A surgical visualization system, comprising: a control circuit communicatively coupled to a straight line laser source, a structured light emitter, and an image sensor; and a memory communicatively coupled to the control circuit, wherein the memory stores instructions which, when executed, cause the control circuit to: control the straight line laser source to project a straight laser line reference; control the structured light source to emit a structured light pattern onto a surface of distal end of a first and second jaw of a surgical device; control the image sensor to detect the projected straight laser line and structured light reflected from the surface of the distal end of the shaft of the surgical device; and determine a first distance "$d_1$" from the projected straight laser line reference to the of the distal end of the first jaw; and determine a second distance "$d_2$" from the projected straight laser line reference to the of the distal end of the second jaw.

Example 14. The surgical visualization system of Example 13, wherein the memory stores instructions executable by the control circuit to determine a state of the first and second jaws based on the respective first and second distances "$d_1$" and "$d_2$."

Example 15. The surgical visualization system of Example 13 or 14, wherein the memory stores instructions executable by the control circuit to provide commands or signals to a robotic control system.

Example 16. The surgical visualization system of Example 15, wherein the commands or signals to the robotic control system are configured to center the first and second jaws.

Example 17. The surgical visualization system of Examples 15 or 16, wherein the commands or signals to the robotic control system are configured to home the first and second jaws Example 18. The surgical visualization system of any one of Examples 13-17, wherein the memory stores instructions executable by the control circuit to provide image data associated with a surgical scene and the first and second distances "$d_1$" and "$d_2$" from the projected straight laser line reference to the of the distal end of the respective first and second jaws to a display of a video monitoring system.

Example 19. The surgical visualization system of Example 18, wherein the memory stores instructions executable by the control circuit to pulse the image data in alternative frames displayed on the display of the video monitoring system.

While several forms have been illustrated and described, it is not the intention of Applicant to restrict or limit the scope of the appended claims to such detail. Numerous modifications, variations, changes, substitutions, combinations, and equivalents to those forms may be implemented and will occur to those skilled in the art without departing from the scope of the present disclosure. Moreover, the structure of each element associated with the described forms can be alternatively described as a means for providing the function performed by the element. Also, where materials are disclosed for certain components, other materials may be used. It is therefore to be understood that the foregoing description and the appended claims are intended to cover all such modifications, combinations, and variations as falling within the scope of the disclosed forms. The appended claims are intended to cover all such modifications, variations, changes, substitutions, modifications, and equivalents.

The foregoing detailed description has set forth various forms of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, and/or examples can be implemented, individually and/or collectively, by a wide range of hardware, software, firmware, or virtually any combination thereof. Those skilled in the art will recognize that some aspects of the forms disclosed herein, in whole or in part, can be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and or firmware would be well within the skill of one of skill in the art in light of this disclosure. In addition, those skilled in the art will appreciate that the mechanisms of the subject matter described herein are capable of being distributed as one or more program products in a variety of forms, and that an illustrative form of the subject matter described herein applies regardless of the particular type of signal bearing medium used to actually carry out the distribution.

Instructions used to program logic to perform various disclosed aspects can be stored within a memory in the system, such as dynamic random access memory (DRAM), cache, flash memory, or other storage. Furthermore, the instructions can be distributed via a network or by way of other computer readable media. Thus a machine-readable medium may include any mechanism for storing or transmitting information in a form readable by a machine (e.g., a computer), but is not limited to, floppy diskettes, optical disks, compact disc, read-only memory (CD-ROMs), and magneto-optical disks, read-only memory (ROMs), random access memory (RAM), erasable programmable read-only memory (EPROM), electrically erasable programmable read-only memory (EEPROM), magnetic or optical cards, flash memory, or a tangible, machine-readable storage used in the transmission of information over the Internet via electrical, optical, acoustical or other forms of propagated signals (e.g., carrier waves, infrared signals, digital signals, etc.). Accordingly, the non-transitory computer-readable medium includes any type of tangible machine-readable medium suitable for storing or transmitting electronic instructions or information in a form readable by a machine (e.g., a computer).

As used in any aspect herein, the term "control circuit" may refer to, for example, hardwired circuitry, programmable circuitry (e.g., a computer processor including one or more individual instruction processing cores, processing unit, processor, microcontroller, microcontroller unit, controller, digital signal processor (DSP), programmable logic device (PLD), programmable logic array (PLA), or field programmable gate array (FPGA)), state machine circuitry, firmware that stores instructions executed by programmable circuitry, and any combination thereof. The control circuit may, collectively or individually, be embodied as circuitry that forms part of a larger system, for example, an integrated circuit (IC), an application-specific integrated circuit (ASIC), a system on-chip (SoC), desktop computers, laptop computers, tablet computers, servers, smart phones, etc. Accordingly, as used herein "control circuit" includes, but is not limited to, electrical circuitry having at least one discrete electrical circuit, electrical circuitry having at least one integrated circuit, electrical circuitry having at least one application specific integrated circuit, electrical circuitry forming a general purpose computing device configured by a computer program (e.g., a general purpose computer configured by a computer program which at least partially carries out processes and/or devices described herein, or a microprocessor configured by a computer program which at least partially carries out processes and/or devices described herein), electrical circuitry forming a memory device (e.g., forms of random access memory), and/or electrical circuitry forming a communications device (e.g., a modem, communications switch, or optical-electrical equipment). Those having skill in the art will recognize that the subject matter described herein may be implemented in an analog or digital fashion or some combination thereof.

As used in any aspect herein, the term "logic" may refer to an app, software, firmware and/or circuitry configured to perform any of the aforementioned operations. Software may be embodied as a software package, code, instructions, instruction sets and/or data recorded on non-transitory computer readable storage medium. Firmware may be embodied as code, instructions or instruction sets and/or data that are hard-coded (e.g., nonvolatile) in memory devices.

As used in any aspect herein, the terms "component," "system," "module" and the like can refer to a computer-related entity, either hardware, a combination of hardware and software, software, or software in execution.

As used in any aspect herein, an "algorithm" refers to a self-consistent sequence of steps leading to a desired result, where a "step" refers to a manipulation of physical quantities and/or logic states which may, though need not necessarily, take the form of electrical or magnetic signals capable of being stored, transferred, combined, compared, and otherwise manipulated. It is common usage to refer to these signals as bits, values, elements, symbols, characters, terms, numbers, or the like. These and similar terms may be associated with the appropriate physical quantities and are merely convenient labels applied to these quantities and/or states.

A network may include a packet switched network. The communication devices may be capable of communicating with each other using a selected packet switched network communications protocol. One example communications protocol may include an Ethernet communications protocol which may be capable permitting communication using a Transmission Control Protocol/Internet Protocol (TCP/IP). The Ethernet protocol may comply or be compatible with the Ethernet standard published by the Institute of Electrical and Electronics Engineers (IEEE) titled "IEEE 802.3 Standard", published in December, 2008 and/or later versions of this standard. Alternatively or additionally, the communication devices may be capable of communicating with each other using an X.25 communications protocol. The X.25 communications protocol may comply or be compatible with a standard promulgated by the International Telecommunication Union-Telecommunication Standardization Sector (ITU-T). Alternatively or additionally, the communication devices may be capable of communicating with each other using a frame relay communications protocol. The frame relay communications protocol may comply or be compatible with a standard promulgated by Consultative Committee for International Telegraph and Telephone (CCITT) and/or the American National Standards Institute (ANSI). Alternatively or additionally, the transceivers may be capable of communicating with each other using an Asynchronous Transfer Mode (ATM) communications protocol. The ATM communications protocol may comply or be compatible with an ATM standard published by the ATM Forum titled "ATM-MPLS Network Interworking 2.0" published August 2001, and/or later versions of this standard. Of course, different and/or after-developed connection-oriented network communication protocols are equally contemplated herein.

Unless specifically stated otherwise as apparent from the foregoing disclosure, it is appreciated that, throughout the foregoing disclosure, discussions using terms such as "processing," "computing," "calculating," "determining," "displaying," or the like, refer to the action and processes of a computer system, or similar electronic computing device, that manipulates and transforms data represented as physical (electronic) quantities within the computer system's registers and memories into other data similarly represented as physical quantities within the computer system memories or registers or other such information storage, transmission or display devices.

One or more components may be referred to herein as "configured to," "configurable to," "operable/operative to," "adapted/adaptable," "able to," "conformable/conformed to," etc. Those skilled in the art will recognize that "configured to" can generally encompass active-state components and/or inactive-state components and/or standby-state components, unless context requires otherwise.

The terms "proximal" and "distal" are used herein with reference to a clinician manipulating the handle portion of the surgical instrument. The term "proximal" refers to the portion closest to the clinician and the term "distal" refers to the portion located away from the clinician. It will be further appreciated that, for convenience and clarity, spatial terms such as "vertical", "horizontal", "up", and "down" may be used herein with respect to the drawings. However, surgical instruments are used in many orientations and positions, and these terms are not intended to be limiting and/or absolute.

Those skilled in the art will recognize that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to claims containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations.

In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that typically a disjunctive word and/or phrase presenting two or more alternative terms, whether in the description, claims, or drawings, should be understood to contemplate the possibilities of including one of the terms, either of the terms, or both terms unless context dictates otherwise. For example, the phrase "A or B" will be typically understood to include the possibilities of "A" or "B" or "A and B."

Wth respect to the appended claims, those skilled in the art will appreciate that recited operations therein may generally be performed in any order. Also, although various operational flow diagrams are presented in a sequence(s), it should be understood that the various operations may be performed in other orders than those which are illustrated, or may be performed concurrently. Examples of such alternate orderings may include overlapping, interleaved, interrupted, reordered, incremental, preparatory, supplemental, simultaneous, reverse, or other variant orderings, unless context dictates otherwise. Furthermore, terms like "responsive to," "related to," or other past-tense adjectives are generally not intended to exclude such variants, unless context dictates otherwise.

It is worthy to note that any reference to "one aspect," "an aspect," "an exemplification," "one exemplification," and the like means that a particular feature, structure, or characteristic described in connection with the aspect is included in at least one aspect. Thus, appearances of the phrases "in one aspect," "in an aspect," "in an exemplification," and "in one exemplification" in various places throughout the specification are not necessarily all referring to the same aspect. Furthermore, the particular features, structures or characteristics may be combined in any suitable manner in one or more aspects.

Any patent application, patent, non-patent publication, or other disclosure material referred to in this specification and/or listed in any Application Data Sheet is incorporated by reference herein, to the extent that the incorporated materials is not inconsistent herewith. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

In summary, numerous benefits have been described which result from employing the concepts described herein. The foregoing description of the one or more forms has been presented for purposes of illustration and description. It is not intended to be exhaustive or limiting to the precise form disclosed. Modifications or variations are possible in light of the above teachings. The one or more forms were chosen and described in order to illustrate principles and practical application to thereby enable one of ordinary skill in the art to utilize the various forms and with various modifications as are suited to the particular use contemplated. It is intended that the claims submitted herewith define the overall scope.

The invention claimed is:

1. A surgical visualization system, comprising:
   a control circuit communicatively coupled to a straight line laser source, a structured light emitter, and an image sensor; and
   a memory communicatively coupled to the control circuit, wherein the memory stores instructions which, when executed, cause the control circuit to:
      control the straight line laser source to project a straight laser line reference;
      control the structured light emitter to emit a structured light pattern onto a surface of an element of a surgical device;
      control the image sensor to detect the projected straight laser line reference and structured light reflected from the surface of the element of the surgical device; and
      determine a position of the element of the surgical device relative to the projected straight laser line reference to measure a deflection of the element of the surgical device, wherein the position is determined based on a shortest distance between the element of the surgical device and the projected straight laser line reference,
wherein the straight laser line reference extends in parallel along at least a portion of the element when the element of the surgical device is in an undeflected position.

2. The surgical visualization system of claim 1, wherein the element of the surgical device is a movable element and the memory stores instructions executable by the control circuit to determine the state of the movable element.

3. The surgical visualization system of claim 1, wherein the memory stores instructions executable by the control circuit to provide commands or signals to a robotic control system.

4. The surgical visualization system of claim 3, wherein the commands or signals to the robotic control system are configured by the control circuit to adjust a position of the element of the surgical device based on the detected projected straight laser line reference and the structured light reflected from the surface of the element of the surgical device.

5. The surgical visualization system of claim 1, wherein the memory stores instructions executable by the control circuit to provide image data associated with a surgical scene and the determined position of the element to a display of a video monitoring system.

6. The surgical visualization system of claim 5, wherein the memory stores instructions executable by the control circuit to pulse the image data in alternative frames displayed on the display of the video monitoring system.

7. A surgical visualization system, comprising:
a control circuit communicatively coupled to a straight line laser source, a structured light emitter, and an image sensor; and
a memory communicatively coupled to the control circuit, wherein the memory stores instructions which, when executed, cause the control circuit to:
control the straight line laser source to project a straight laser line reference;
control the structured light emitter to emit a structured light pattern onto a surface of a distal end of a shaft of a surgical device;
control the image sensor to detect the projected straight laser line reference and structured light reflected from the surface of the distal end of the shaft of the surgical device; and
determine a distance "d" from the projected straight laser line reference to the distal end of the shaft of the surgical device to measure a deflection of the shaft of the surgical device, wherein the distance "d" is a shortest distance between the projected straight laser line reference and the distal end of the shaft of the surgical device,
wherein the straight laser line reference extends in parallel along at least a portion of the shaft when the shaft of the surgical device is in an undeflected position.

8. The surgical visualization system of claim 7, wherein the memory stores instructions executable by the control circuit to determine a force "F" applied to the shaft based on the distance "d."

9. The surgical visualization system of claim 7, wherein the memory stores instructions executable by the control circuit to provide commands or signals to a robotic control system.

10. The surgical visualization system of claim 9, wherein the commands or signals to the robotic control system are configured by the control circuit to control a state of the surgical device.

11. The surgical visualization system of claim 7, wherein the memory stores instructions executable by the control circuit to provide image data associated with a surgical scene and the distance "d" from the projected straight laser line reference to the distal end of the shaft of the surgical device to a display of a video monitoring system.

12. The surgical visualization system of claim 11, wherein the memory stores instructions executable by the control circuit to pulse the image data in alternative frames displayed on the display of the video monitoring system.

13. A surgical visualization system, comprising:
a control circuit communicatively coupled to a straight line laser source, a structured light emitter, and an image sensor; and
a memory communicatively coupled to the control circuit, wherein the memory stores instructions which, when executed, cause the control circuit to:
control the straight line laser source to project a straight laser line reference;
control the structured light emitter to emit a structured light pattern onto a surface of a distal end of a first jaw and onto a surface of a distal end of a second jaw of a surgical device;
control the image sensor to detect the projected straight laser line reference and structured light reflected from the surfaces of the distal ends of the first and second jaws of the surgical device; and
determine a first distance "$d_1$" from the projected straight laser line reference to a tip of the distal end of the first jaw to measure a change in a position of the first jaw, wherein the first distance "$d_1$" is a shortest distance between the projected straight laser line reference and the tip of the distal end of the first jaw; and
determine a second distance "$d_2$" from the projected straight laser line reference to a tip of the distal end of the second jaw to measure a change in a position of the second jaw, wherein the second distance "$d_2$" is a shortest distance between the projected straight laser line reference and the tip of the distal end of the second jaw, and
wherein the straight laser line reference extends in parallel along at least a portion of the first jaw and at least a portion of the second jaw when the first jaw and the second jaw are in a first position.

14. The surgical visualization system of claim 13, wherein the memory stores instructions executable by the control circuit to determine a state of the first and second jaws based on the respective first and second distances "$d_1$" and "$d_2$."

15. The surgical visualization system of claim 13, wherein the memory stores instructions executable by the control circuit to provide commands or signals to a robotic control system.

16. The surgical visualization system of claim 15, wherein the commands or signals to the robotic control system are configured to center the first and second jaws.

17. The surgical visualization system of claim 15, wherein the commands or signals to the robotic control system are configured to home the first and second jaws.

18. The surgical visualization system of claim 13, wherein the memory stores instructions executable by the control circuit to provide image data associated with a surgical scene and the first and second distances "$d_1$" and "$d_2$" from the projected straight laser line reference to the tips of the distal ends of the respective first and second jaws to a display of a video monitoring system.

19. The surgical visualization system of claim 18, wherein the memory stores instructions executable by the control circuit to pulse the image data in alternative frames displayed on the display of the video monitoring system.

20. The surgical visualization system of claim 13, wherein the first position of the first jaw and the second jaw is a centered position of the first jaw and the second jaw.

21. A surgical system, comprising:
   a straight line laser source;
   a structured light emitter;
   an image sensor;
   a control circuit communicatively coupled to the straight line laser source, the structured light emitter, and the image sensor; and
   a memory communicatively coupled to the control circuit, wherein the memory stores instructions which, when executed, cause the control circuit to:
      control the straight line laser source to project a straight laser line reference;
      control the structured light emitter to emit a structured light pattern onto a surface of an element of a surgical device;
      control the image sensor to detect the projected straight laser line reference and structured light reflected from the surface of the element of the surgical device;
      determine a deflection distance between the element of the surgical device and the projected straight laser line reference;
      cause an adjustment of a position of the element of the surgical device based on the deflection distance; and
      wherein the straight laser line reference extends in parallel along at least a portion of the element when the element of the surgical device is in an undeflected position.

* * * * *